(12) United States Patent
Panitch et al.

(10) Patent No.: US 9,217,016 B2
(45) Date of Patent: Dec. 22, 2015

(54) HYALURONIC ACID-BINDING SYNTHETIC PEPTIDOGLYCANS, PREPARATION, AND METHODS OF USE

(75) Inventors: Alyssa Panitch, West Lafayette, IN (US); Jonathan C. Bernhard, South Bend, IN (US); John E. Paderi, San Francisco, CA (US); Shaili Sharma, Lafayette, IN (US)

(73) Assignee: SYMIC IP, LLC, San Francisco, CA (US)

( * ) Notice: Subject to any disclaimer, the term of this patent is extended or adjusted under 35 U.S.C. 154(b) by 0 days.

(21) Appl. No.: 14/119,341

(22) PCT Filed: May 24, 2012

(86) PCT No.: PCT/US2012/039404
§ 371 (c)(1),
(2), (4) Date: Nov. 21, 2013

(87) PCT Pub. No.: WO2012/162534
PCT Pub. Date: Nov. 29, 2012

(65) Prior Publication Data
US 2014/0301983 A1    Oct. 9, 2014

Related U.S. Application Data

(60) Provisional application No. 61/489,602, filed on May 24, 2011, provisional application No. 61/550,621, filed on Oct. 24, 2011.

(51) Int. Cl.
| | |
|---|---|
| C07K 9/00 | (2006.01) |
| C07K 14/78 | (2006.01) |
| C07K 14/47 | (2006.01) |
| A61K 38/17 | (2006.01) |
| A61K 38/39 | (2006.01) |
| C08B 37/08 | (2006.01) |
| A61L 27/36 | (2006.01) |
| A61L 27/48 | (2006.01) |
| A61L 27/54 | (2006.01) |

(52) U.S. Cl.
CPC .............. *C07K 9/00* (2013.01); *A61K 38/1709* (2013.01); *A61K 38/39* (2013.01); *A61L 27/3654* (2013.01); *A61L 27/48* (2013.01); *A61L 27/54* (2013.01); *C07K 14/4725* (2013.01); *C07K 14/78* (2013.01); *C08B 37/0072* (2013.01)

(58) Field of Classification Search
CPC ................................. C07K 9/00; C07K 14/78
See application file for complete search history.

(56) References Cited

U.S. PATENT DOCUMENTS

| | | | |
|---|---|---|---|
| 4,683,298 A | 7/1987 | Yalpani | |
| 5,271,929 A | 12/1993 | Hashiguchi et al. | |
| 5,547,936 A | 8/1996 | Ruoslahti et al. | |
| 5,693,625 A | 12/1997 | Barritault et al. | |
| 5,852,004 A | 12/1998 | Barritault et al. | |
| 5,955,578 A | 9/1999 | Pierschbacher et al. | |
| 5,997,895 A | 12/1999 | Narotam et al. | |
| 6,703,491 B1 | 3/2004 | Homburger et al. | |
| 6,822,071 B1 | 11/2004 | Stephens et al. | |
| 6,864,235 B1 | 3/2005 | Turley et al. | |
| 6,932,973 B2 | 8/2005 | Barritault et al. | |
| 7,098,194 B2 | 8/2006 | Chenite et al. | |
| 7,534,436 B2 | 5/2009 | Courty et al. | |
| 7,592,009 B2 | 9/2009 | Hubbell et al. | |
| 7,671,018 B2 | 3/2010 | Carson et al. | |
| 7,709,439 B2 | 5/2010 | Helmus et al. | |
| 7,732,427 B2 | 6/2010 | Kiick et al. | |
| 7,737,131 B2 | 6/2010 | Kiick et al. | |
| 7,803,905 B2 | 9/2010 | Farach-Carson et al. | |
| 7,842,667 B2 | 11/2010 | Seliktar et al. | |
| 7,851,445 B2 | 12/2010 | Stupp et al. | |
| 7,855,187 B1 | 12/2010 | Prestwich et al. | |
| 7,862,831 B2 | 1/2011 | Wang et al. | |
| 7,897,165 B2 | 3/2011 | Elisseeff et al. | |
| 7,919,111 B2 | 4/2011 | Chudzik et al. | |
| 8,007,774 B2 | 8/2011 | Seliktar et al. | |
| 8,114,834 B2 | 2/2012 | Hsu et al. | |
| 8,188,220 B2 | 5/2012 | Ruoslahti et al. | |
| 8,268,950 B2 | 9/2012 | Elisseeff | |
| 8,283,414 B2 | 10/2012 | Yu et al. | |
| 8,304,388 B2 | 11/2012 | Chettibi et al. | |
| 8,314,195 B2 | 11/2012 | Elisseeff | |
| 8,329,673 B2 | 12/2012 | Prestwich et al. | |
| 8,338,390 B2 | 12/2012 | Kiick et al. | |
| 8,343,764 B2 | 1/2013 | Abad et al. | |
| 8,343,942 B2 | 1/2013 | Oottamasathien et al. | |
| 8,367,639 B2 | 2/2013 | Kilck et al. | |
| 8,389,467 B2 | 3/2013 | Chaput et al. | |

(Continued)

FOREIGN PATENT DOCUMENTS

| | | |
|---|---|---|
| CA | 2299687 C | 10/2009 |
| EP | 0462194 | 6/1994 |

(Continued)

OTHER PUBLICATIONS

Mummert, 2005, Immunological Roles of Hyaluronan, Immunologic Research, 31(3): 189-205.*
Mummert et al., 2000, J Exp Med, 192(6): 769-779.*
U.S. Appl. No. 14/474,832, filed Sep. 2, 2014, John E. Paderi et al.
U.S. Appl. No. 14/497,189, filed Sep. 25, 2014, Alyssa Panitch et al.
U.S. Appl. No. 14/466,889, filed Aug. 22, 2014, Alyssa Panitch et al.
Adiquzel, et al., "Collagens in the progression and complications of atherosclerosis" Vascular Medicine. 14, 73-89. (2009).
Allaire, et al., "Endothelial Cell Injury in Cardiovascular Surgery: The Intimal Hyperplastic Response" National Center for Biotechnology Information Ann Thorac Surg, 63(2). 582-91, (1997).

(Continued)

*Primary Examiner* — Amber D Steele
(74) *Attorney, Agent, or Firm* — Sheppard Mullin Richter & Hampton LLP

(57) ABSTRACT

This invention pertains to the field of hyaluronic acid-binding synthetic peptidoglycans and methods of forming and using the same.

17 Claims, 26 Drawing Sheets

(56) References Cited

U.S. PATENT DOCUMENTS

| | | |
|---|---|---|
| 8,415,325 B2 | 4/2013 | Kiick et al. |
| 8,431,146 B2 | 4/2013 | Harley et al. |
| 8,450,271 B2 | 5/2013 | Shah et al. |
| 8,470,780 B2 | 6/2013 | Ruoslahti et al. |
| 8,476,220 B2 | 7/2013 | Barritault et al. |
| 8,557,774 B2 | 10/2013 | Vandroux et al. |
| 8,703,740 B2 | 4/2014 | Cho et al. |
| 8,790,631 B2 | 7/2014 | Barritault et al. |
| 8,846,003 B2 | 9/2014 | Panitch et al. |
| 2002/0098153 A1 | 7/2002 | Allen et al. |
| 2002/0183282 A1 | 12/2002 | Dahricorreia et al. |
| 2003/0087255 A1 | 5/2003 | Barritault et al. |
| 2003/0149173 A1 | 8/2003 | Rhee et al. |
| 2003/0199615 A1 | 10/2003 | Chaput et al. |
| 2004/0091540 A1 | 5/2004 | DesRosiers et al. |
| 2004/0127416 A1 | 7/2004 | Massia et al. |
| 2004/0214272 A1 | 10/2004 | La Rosa et al. |
| 2004/0236092 A1 | 11/2004 | Dziarski et al. |
| 2005/0043221 A1 | 2/2005 | Fallon et al. |
| 2005/0108791 A1 | 5/2005 | Edgerton |
| 2005/0113297 A1 | 5/2005 | Francois et al. |
| 2005/0147679 A1 | 7/2005 | Petito et al. |
| 2005/0187146 A1 | 8/2005 | Helmus et al. |
| 2005/0196377 A1 | 9/2005 | Ratcliffe et al. |
| 2006/0024696 A1 | 2/2006 | Kapur et al. |
| 2006/0075522 A1 | 4/2006 | Cleveland et al. |
| 2006/0123505 A1 | 6/2006 | Kikuchi et al. |
| 2006/0241022 A1 | 10/2006 | Bowen et al. |
| 2006/0252692 A1 | 11/2006 | Lasser et al. |
| 2007/0098675 A1 | 5/2007 | Elisseeff et al. |
| 2007/0124833 A1 | 5/2007 | Abad et al. |
| 2007/0141020 A1 | 6/2007 | Barritault et al. |
| 2007/0167441 A1 | 7/2007 | Halbrook et al. |
| 2007/0218102 A1 | 9/2007 | Chudzik et al. |
| 2007/0224247 A1 | 9/2007 | Chudzik et al. |
| 2007/0298071 A1 | 12/2007 | Harley et al. |
| 2008/0069774 A1 | 3/2008 | Liotta et al. |
| 2008/0090998 A1 | 4/2008 | Abad et al. |
| 2008/0131466 A1 | 6/2008 | Reed et al. |
| 2008/0247995 A1 | 10/2008 | Decarlo et al. |
| 2008/0248569 A1 | 10/2008 | Mata et al. |
| 2009/0022771 A1 | 1/2009 | Lynn et al. |
| 2009/0030525 A1 | 1/2009 | Desrosiers et al. |
| 2009/0075281 A1 | 3/2009 | Hristova et al. |
| 2009/0092674 A1 | 4/2009 | Ingram et al. |
| 2009/0100536 A1 | 4/2009 | Adams et al. |
| 2009/0158452 A1 | 6/2009 | Johnson et al. |
| 2009/0162436 A1 | 6/2009 | Carson et al. |
| 2009/0183270 A1 | 7/2009 | Adams et al. |
| 2009/0202616 A1 | 8/2009 | Chong et al. |
| 2009/0324722 A1 | 12/2009 | Elisseeff et al. |
| 2010/0003329 A1 | 1/2010 | Elisseeff et al. |
| 2010/0004196 A1 | 1/2010 | De Agostini et al. |
| 2010/0017904 A1 | 1/2010 | Abad et al. |
| 2010/0021545 A1 | 1/2010 | Chaput et al. |
| 2010/0029549 A1 | 2/2010 | Chaput et al. |
| 2010/0111842 A1 | 5/2010 | Boyden et al. |
| 2010/0119577 A1 | 5/2010 | Min |
| 2010/0137510 A1 | 6/2010 | Seliktar et al. |
| 2010/0166830 A1 | 7/2010 | Harley et al. |
| 2010/0210509 A1 | 8/2010 | Oh et al. |
| 2010/0227836 A1 | 9/2010 | Elisseeff et al. |
| 2011/0038828 A1 | 2/2011 | Seliktar et al. |
| 2011/0087152 A1 | 4/2011 | David et al. |
| 2011/0207669 A1 | 8/2011 | Vandroux et al. |
| 2011/0214206 A1 | 9/2011 | La Rosa et al. |
| 2011/0238000 A1 | 9/2011 | Seliktar et al. |
| 2011/0258734 A1 | 10/2011 | Adams et al. |
| 2011/0269208 A1 | 11/2011 | Burdick et al. |
| 2012/0020911 A1 | 1/2012 | Seliktar et al. |
| 2012/0034164 A1 | 2/2012 | Ruoslahti et al. |
| 2012/0058943 A1 | 3/2012 | Werner et al. |
| 2012/0100106 A1 | 4/2012 | Panitch et al. |
| 2012/0227131 A1 | 9/2012 | Abad et al. |
| 2012/0246748 A1 | 9/2012 | Guo et al. |
| 2012/0258068 A1 | 10/2012 | Seliktar et al. |
| 2012/0294925 A1 | 11/2012 | Lynn et al. |
| 2013/0035307 A1 | 2/2013 | Prestwich et al. |
| 2013/0045926 A1 | 2/2013 | DeVore et al. |
| 2013/0052155 A1 | 2/2013 | Marcolongo et al. |
| 2013/0074202 A1 | 3/2013 | Adams et al. |
| 2013/0101628 A1 | 4/2013 | Webber et al. |
| 2013/0109808 A1 | 5/2013 | Elisseeff |
| 2013/0116405 A1 | 5/2013 | Yu et al. |
| 2013/0152224 A1 | 6/2013 | Abad et al. |
| 2013/0190246 A1 | 7/2013 | Paderi et al. |
| 2013/0196896 A1 | 8/2013 | Komatsu et al. |
| 2013/0323311 A1 | 12/2013 | Paderi et al. |
| 2013/0333061 A1 | 12/2013 | Wu et al. |
| 2014/0288002 A1 | 9/2014 | Panitch et al. |
| 2014/0301972 A1 | 10/2014 | Barritault et al. |

FOREIGN PATENT DOCUMENTS

| | | | |
|---|---|---|---|
| EP | 1586652 | 10/2005 | |
| EP | 1677807 | 7/2006 | |
| EP | 2292773 | 3/2011 | |
| EP | 2295582 | 3/2011 | |
| JP | 2000-109500 | 4/2000 | |
| JP | 2005185101 | 7/2005 | |
| WO | WO-92/12175 | 7/1992 | |
| WO | WO 9927105 | 6/1999 | |
| WO | WO-01/19386 | 3/2001 | |
| WO | WO-2005/055800 | 6/2005 | |
| WO | WO-2005/061018 | 7/2005 | |
| WO | WO-2005/082430 | 9/2005 | |
| WO | WO-2005/116066 | 12/2005 | |
| WO | WO-2006/047758 | 5/2006 | |
| WO | WO 2006/130974 | * 12/2006 | ............. A61K 38/10 |
| WO | WO-2006/130974 | 12/2006 | |
| WO | WO 2007/044026 | 4/2007 | |
| WO | WO 2008034648 | 3/2008 | |
| WO | WO 2008/066816 | 6/2008 | |
| WO | WO 2008070179 | 6/2008 | |
| WO | WO-2008/126092 | 10/2008 | |
| WO | WO-2008/152639 | 12/2008 | |
| WO | WO 2009/120995 | 10/2009 | |
| WO | WO 2009120995 | 10/2009 | |
| WO | WO 2010033564 | 3/2010 | |
| WO | WO-2010/122232 | 10/2010 | |
| WO | WO 2010115156 | 10/2010 | |
| WO | WO-2010/139953 | 12/2010 | |
| WO | WO-2011/057286 | 5/2011 | |
| WO | WO-2011/094149 | 8/2011 | |
| WO | WO-2011/156445 | 12/2011 | |
| WO | WO 2011163492 | 12/2011 | |
| WO | WO 2012/112767 | 8/2012 | |
| WO | WO 2012/162534 | 11/2012 | |
| WO | WO-2013/110056 | 7/2013 | |
| WO | WO-2014/028209 | 2/2014 | |
| WO | WO-2014/038866 | 3/2014 | |
| WO | WO-2014/040591 | 5/2014 | |
| WO | WO 2014/071132 | 5/2014 | |
| WO | WO 2014099997 | 6/2014 | |

OTHER PUBLICATIONS

Ando, "Opinion Statement of the Effect of Mechanical Stress on Carilage Tissue Engineering" The Open Bone Journal, 2, 32-37 (2010).

Armstrong, David G. et al., "The Role of Matrix Metalloproteinases in Wound Healing" J Am Podiatr Med Assoc, 92(1), 12-18 (2002).

Ashcroft et al.; "Aging alters the inflammatory and endothelial cell adhesion molecule profiles during human cutaneous wound healing" Laboratory Investigation 78(1). 47 -58, (1998).

Bernhard et al,. "Synthesis and characterization of an aggrecan mimic" Acta Biomaterialia 8(4).1543-1550, (2012).

Bhide et al., "Collagen Phagocytosis by Fibroblasts Is Regulated by Decorin" J. Biol. Chem., 280(24), 23103-23113 (2005).

Bierbaum et al., "Collageneous Matrix Coatings on Titanium Implants Modified with Decorin and Chondroitin Sulfate: Characterization and Influence on Osteoblastic Cells" Journal of Biomedical Materials Research, 77A, 551-562. (2006).

(56) References Cited

OTHER PUBLICATIONS

Birch, Mary et al., "Animal Models for Adult Dermal Wound Healing" Methods in Molecular Medicine, 117, 223-235 (2005).
Braunwald et al., "The Problem of Persistent Platelet Activation in Acute Coronary Syndromes and Following Percutaneous Coronary Intervention" Clinical Cardiology. 31-3 (Suppl. 1), 117-120.( 2008).
Brem, Harold et al., "Cellular and molecular basis of wound healing in diabetes," The Journal of Clinical Investigation, 117(5), 1219-22 (2007).
Broughton et al; "The basic science of wound healing." Plastic and Reconstructive Surgery 117(7S), 12S-34S (2006).
Business Wire "ZymoGenetics Reports New Findings on Antithrombotic Activities of CTRP1; Novel Protein Prevents Platelet Thrombosis without Causing Bleeding", www.thefreelibrary.com/ZymoGenetics+Reports+New+Findings+on+Antithrombotic+Activities+of+a0105542135, pp. 1-3 (2003).
Chiang et al., "Cloning, Characterization, and Functional Studies of a 47-kDa Platelet Receptor for Type III Collagen" The Journal of Biological Chemistry, 277( 38), 34896-34901 (2002).
Chiang et al., "Peptides Derived From Platelet Non-Integrin Collagen-Receptors or Types I and III Collagen Inhibit Collagen-Platelet Interaction" Cardiovascular & Haematological Disorders-Drug Targets, 7(1), 71-75 (2007).
Chiang, Thomas M., et al., "A Synthetic Peptide Derived from the Sequence of a Type I Collagen Receptor Inhibits Type I Collagen-Mediated Platelet Aggregation" The Journal of Clinical Investigation, 100(8), 2079-2084 (1997).
Chung C. et al., "Influence of gel properties on neocatilage formation by auricular chondrocytes photoencapsulated in hyaluronic acid networks" Journal of Biomedical Materials Research Part A, 77(3), 518-25 (2006).
Chung, C. et al. "The influence of degradation characteristics of hyaluronic acid hydrogels on in vitro neocartilage formation by mesenchymal stem cells" Biomaterials, 30(26), 4287-96 (2009).
Chupa, Janeen M., et al., "Vascular Cell Responses to Polysaccharide Materials: In Vitro and In Vivo Evaluations" Biomaterials, 21, 2315-2322 (2000).
Danielson, Keith G. et al., "Targeted Disruption of Decorin Leads to Abnormal Collagen Fibril Morphology and Skin Fragility" The Journal of Cell Biology, 136, 729-743 (1997).
Demling, Robert H. et al., "Small Intestinal Submucosa Wound Matric and Full-thickness Venous Ulcers: Preliminary Results" Wounds Research, 16(1), 18-22 (2004).
Di Mario, et al. "The "Dark Side" of Percutaneous Coronary Interventions" Journal of the American College of Cardiology Interventions,1(3):277-278 (2008).
Drachman, et al., "Inflammation as a Mechanism and Therapeutic Target for In-stent Restenosis" Current Atherosclerosis Reports; 7(1), 44-49 (2005).
Extended European Search Report for EP11798931, completed Dec. 4, 2013.
Falanga, Vincent "Wound healing and its impairment in the diabetic foot," Lancet, 366, 1736-43 (2005).
Farb, et al. "Pathology of Acute and Chronic Coronary Stenting in Humans" Circulation, 99, 44-52 (1999).
FDA, "Guidance for Industry Chronic Cutaneous Ulcer and Burn Wounds Developing Products for Treatment" (Jun. 2006).
Flaumenhaft, Robert et al., "Extracellular Matrix Regulation of Growth Factor and Protease Activity" 1991, Current Opinion in Cell Biology, 3, 817-23 (1991).
Fransson, Lars-Åke et al., "Periodate Oxidation and Alkaline Degradation of Heparin-Related Glycans" Carbohydrate Research, 80, 131-145 (1980).
Fulzele, et al., "Study of the Biodegradation and In Vivo Biocompatibility of Novel Biomaterials" European Journal of Pharmaceutical Sciences, 20, 53-61(2003).V.
Gallant, Corrie L. et al., "Cytokine and Growth Factor mRNA Expression Patterns Associated with the Hypercontracted, Hyperpigmented Healing Phenotype of Red Duroc Pigs: A Model of Abnormal Human Scar Development?" J Cutan Med Surg, 9(4), 165-177 (2005).
Gallant, Corrie L. et al., "Molecular, histologic, and gross phenotype of skin wound healing in red Duroc pigs reveals an abnormal healing phenotype of hypercontracted, hyperpigmented scarring" Wound Rep Reg, 12, 305-319 (2004).
Geng, Yeqing et al., "SLRP interaction can protect collagen fibrils from cleavage by collagenases" Matrix Biology, 25, 484-491 (2006).
Gercken, et al. "Results of the Jostent Coronary Stent Graft Implantation in Various Clinical Settings: Procedural and Follow-Up Results" Catheterization and Cardiovascular Interventions.; 56 (3), 353-360 (2002).
Goldoni, Silvia et al; "Biologically active decorin is a monomer in solution." J. Bio. Chem. 279(8), 6606-6612 (2004).
Grassl, E. D., et al., "Fibrin as an Alternative Biopolymer to Type-1 Collagen for the Fabrication of a Media Equivalent" Journal of Biomedical Materials Research, 60(4), 607-612, (2002).
Griese, Daniel P., et al., "Isolation and Transplantation of Autologous Circulating Endothelial Cells Into Denuded Vessels and Prosthetic Grafts: Implications for Cell-Based Vascular Therapy" Circulation, 108, 2710-2715 (2003).
Griffey, et al., "Particulate Dermal Matrix as an Injectable Soft Tissue Replacement Material" J. Biomed. Mater. Res., 58, 10-15 (2001).
Gutman, et al., "Liposomal alendronate for the treatment of restenosis" Journal of Controlled Release, 161, 619-627 (2012).
Hantgan, et al; "Platelets interact with fibrin only after activation." Blood, 65(6) 1299-1311 (1985).
Helms, Brett A. et al. "High affinity peptide based collagen targeting using synthetic phage mimics: from phage display to dendrimerdisplay." J. Am. Chem. Soc. 131, 11683-11685 (2009).
Hemmer, Bernhard et al; "Minimal peptide length requirements for cd4+ t cell clones—implications for molecular mimicry and t cell survival." Int. Immunol., 12(3) 375-383 (2000).
Henn, et al; "CD40 lignd on activated platelets triggers an inflammatory reaction of endothelial cells." Nature, 391, 591-594 (1998).
Hermanson, "Zero-Length Cross-Linkers" Academic Press, 169-186 (1996).
Huizinga et al., "Crystal Structure of the A3 Domain of Human Von Willebrand Factor: Implications for Collagen Binding" Structure, 5 (9), 1147-1156 (1997).
Hunt et al., "Respiratory Gas Tensions and pH in Healing Wounds" American Journal of Surgery, 114, 302-307, (1967).
International Search Report/Written Opinion for PCT/US2009/038624 mailed Dec. 7, 2009.
International Search Report/Written Opinion for PCT/US2010/033543 issued Oct. 8, 2010.
International Preliminary Examination Report along with Written Opinion of the International Searching Authority issued in International PCT application No. PCT/US2012/039404 issued Nov. 26, 2013.
International Preliminary Examination Report issued in International PCT application No. PCT/US2009/038624 issued Sep. 28, 2010.
International Search Report for PCT/US2014/029596, dated Jul. 28, 2014.
International Search Report issued in International Application No. PCT/US2012/039404 mailed Nov. 29, 2012.
Järveläinen, Hannu et al., "A role for decorin in cutaneous wound healing and angiogenesis" Wound Rep Reg, 14, 443-452 (2006).
Järvinen, Tero A. H. et al., "Target-seeking antifibrotic compound enhances wound healing and suppresses scar formation in mice" PNAS, 107(50), 21671-21676 (2010).
Kalamajski et al., "The Decorin Sequence SYIRIADTNIT Binds Collagen Type 1" Journal of Biological Chemistry, 282(22), 16062-16067 (2007).
Kalamajski, "The role of small leucine-rich proteoglycans in collagen fibrillogenesis" Matrix Biology, 29(4), 248-253 (2010).
Khorramizadeh, M.R. et al., "Aging differentially modulates the expression of collagen and collagenase in dermal fibroblasts" Molecular and Cellular Biochemistry, 194, 99-108 (1999).
Kipshidze et al., "Role of the Endothelium in Modulating Neointimal Formation" Journal of the American College of Cardiology, 44(4), 733-739 (2004).

(56) References Cited

OTHER PUBLICATIONS

Kitov, Pavel I. and Bundle, David R., "On the nature of the multivalency effect: a thermodynamic model." J. Am. Chem. Soc., 125, 16271-16284 (2003).
Kraut et al; "Challenges in enzyme mechanism and energetics." Annu. Rev. Biochem., 72, 517-571 (2003).
Lasser, Blood, 2006, 107, 423-430.
Lazic, Tamara et al., "Bioengineered Skin Constructs and Their Use in Wound Healing" 2010, Plastic and Reconstructive Surgery, 127(1S), 75S-90S (2010).
Lemon, Stanley M. et al; "Immunoprecipitation and virus neutralization assays demonstrate qualitative differences between protective antibody responses to inactivated hepatitis a vaccine and passive immunization with immune globulin." J. Infect. Disease 179, 9-19 (1997).
Libby et al. "A Cascade Model for Restenosis—A Special Case of Atherosclerosis Progression" Circulation., 86(6), III-47-III-52 (1992).
Mammen, Mathai, et al., "Polyvalent Interactions in Biological Systems: Implications for Design and Use of Multivalent Ligands and Inhibitors" Angew. Chem. Int. Ed., 37, 2754-2794 (1998).
Martin, Paul "Wound Healing—Aiming for Perfect Skin Regeneration" Science, 276, 75-81, (1997).
Moustafa, M. et al., "A new autologous keratinocyte dressing treatment for non-healing diabetic neuropathic foot ulcers" Diabetic Medicine, 21, 786-789 (2004).
Mummert, "Immunological Roles of Hyaluronan" Immunologic Research, 31 (3), 189-205 (2005).
Oyama et al; "Isolation of lung tumor specific peptides from a random peptide library: generation of diagnostic and cell targeting reagents." Cancer Letters, 202, 219-230 (2003).
Paderi et al., "Design of a Synthetic Collagen-Binding Peptidoglycan that Modulates Collagen" Fibrillogenesis. Biomacromolecules 9, 2562-2566 (2008).
Paderi, John E. et al., "Collagen-Binding Peptidoglycans: A Biomimetic Approach to Modulate Collagen Fibrillogenesis for Tissue Engineering Applications" Tissue Engineering: Part A, 15(10), 2991-2999 (2009).
International Search Report and Written Opinion for PCT/US2011/041654, completed Oct. 26, 2011.
Penc, Stanley F. et al., "Dermatan Sulfate Released after Injury Is a Potent Promoter of Fibroblast Growth Factor-2 Function" The Journal of Biological Chemistry, 273(43), 28116-28121 (1998).
Pentikainen, Markku O. et al; "The proteoglycan decorin links low density lipoproteins with collagen type I." J. Bio. Chem. 272(12), 7633-7638 (1997).
Pignatelli et al; "Hydrogen peroxide is involved in collagen induced platelet activation" Blood, 91 (2) 484-490 (1998).
Pizzo et al., "Extracellular Matrix (ECM) Microstructural Composition Regulates Local Cell-ECM Biomechanics and Fundamental Fibroblast Behavior: A Multidimensional Perspective" Journal Appl. Physiol, 98, 1909-1921 (2005).
Puig, A. et al., "A new decorin-like tetrapeptide for optimal organization of collagen fibres" International Journal of Cosmetic Science, 30, 97-104 (2008).
Radek, Katherine A. et al., "FGF-10 and specific structural elements of dermatan sulfate size and sulfation promote maximal keratinocyte migration and cellular proliferation" Wound Rep Reg, 17, 118-126 (2009).
Ratcliffe, Anthony, "Tissue Engineering of Vascular Grafts" Matrix Biology, 19, 353-357 (2000).
Reed, Charles C. et al., "The role of decorin in collagen fibrillogenesis and skin homeostasis" Glycoconjugate Journal, 19, 249-255 (2003).
Roeder et al., "Tensile Mechanical Properties of Three-Dimensional Type I Collagen Extracellular Matrices With Varied Microstructure" Transactions of the ASME, 124, 214-222 (2002).
Romijn et al., "Mapping the Collagen-Binding Site in the Von Willebrand Factor-A3 Domain" The Journal of Biological Chemistry, 278(17), 15035-15039 (2003).
Roseborough et al; "Prevention and treatment of excessive dermal scarring." J. Natl. Med. Assoc., 96,108-116 (2004).
Rosenblum et al., "Diminished Benefits of Drug-Eluting Stents versus Bare Metal Stents in Patients with Severe Renal Insufficiency" Nephron Clinical Practice, 113, c198-c202, (2009).
Rossi, Francois et al; "Decontamination of surfaces by low pressure plasma discharges" Plasma Process. Polym. 3, 431-442 (2006).
Roy-Chaudhury et al. "Hemodialysis Vascular Access Dysfunction: A Cellular and Molecular Viewpoint" J AM Sco Nephrol, 17(4),1112-1127 (2006).
Rudbach, J. A. et al; "Physical aspects of reversible inactivation of endotoxin." Ann. New York Acad Sci. 133, 629-643 (1966).
Schilling et al., "Wound Healing: A Comparative Study of the Histochemical Changes in Granulation Tissue Contained in Stainless Steel Wire Mesh and Polyvinyl Sponge Cylinders" Surgery, 46(4), 702-710 1959.
Schonherr et al., "Decorin Core Protein Fragment LEU 155-Va1260 Interacts with TGF-Beta but Does Not Compete for Decorin Binding to Type I Collagen" Arch. Biochem. Biophys., 355(2), 241-248 (1998). Abstract Only.
Schultz, Gregory S. et al., "Interactions between extracellular matrix and growth factors in wound healing" Wound Rep Reg, 17, 153-62 (2009).
Scott et al., "Chemical characterization and quantification of proteoglycans in human post-burn hypertrophic and mature scars" Clinical Science, 90(5), 417-25 (1996).
Scott, et al., Decorin mimic inhibits vascular smooth muscle proliferation and migration; PLOS One, 8(11 ): e82456. (2013).
Scott, John E. et al., "Dermatan sulphate-rich proteoglycan associates with rat tail-tendon collagen at the d band in the gap region" Biochem. J., 197(1), 213-216 (1981).
Scott, John E. et al., "Proteoglycan-fibrillar collagen interactions" Biochem. J, 252, 313-323 (1988).
Scott, Paul G. et al., "Molecular and Cellular Aspects of Fibrosis Following Thermal Injury" Thermal Injuries, 16(2), 271-287 (2000).
Shin, Min Kyoung et al, "A novel collagen-binding peptide promotes osteogenic differentiation via $Ca^{2}+$/calmodulin-dependent protein kinase II/ERK/AP-1 signaling pathway in human bone marrow-derived mesenchymal stem cells", Cellular Signaling 20, 613-624 (2008).
Singer, Adam et al., "Cutaneous Wound Healing" The New England Journal of Medicine, 341(10), 738-46 (1999).
Sini et al; "Role of decorin on in vitro fibrillogenesis of type 1 collagen." Glycoconj. J. 14, 871 -874 (1997).
Stuart, et al., "Collagen-Binding peptidoglycans inhibit MMP mediated collagen degradation and reduce dermal scarring" PLOS One, 6(7), e22139 2011.
Suki, Bela et al., "Biomechanis of the lung parenchyma: critical roles of collagen and mechanical forces" J. Appl. Physiol. 98, 1892-1899 (2005).
Svensson et al., "Decorin-binding sites for collagen type I are mainly located in leucine-rich repeats 4-5" J. Biol. Chem., 270(35), 20712-20716 (1995).
Taylor, Kristen R. et al., "Structural and Sequence Motifs in Dermatan Sulfate for Promoting Fibroblast Growth Factor-2 (FGF-2) and FGF-7 Activity" The Journal of Biological Chemistry, 280(7), 5300-5306 (2005).
Tenni et al., "Interaction of Decorin with CNBr Peptides from Collagens I and II Evidence for Multiple Binding Sites and Essential Lysyl Residues in Collagen" Eur. J. Biochem., 269, 1428-1437 (2002).
The USRDS Coordinating, "Incidence, prevalence, patient characteristics, and treatment modality" Center United States Renal Data System, 2, 215-228 (2013).
Tollefsen, "Vascular Dermatan Sulfate and Heparin Cofactor II" Progress in Molecular Biology and Translational Science, 93, 351-372 (2010).
Trengove, Naomi J. et al., "Analysis of the acute and chronic wound environments: the role of proteases and their inhibitors" Wound Rep Reg, 7(6), 442-452 (1999).
Trowbridge, Janet M. et al., "Derman sulfate: new functions from an old glycosaminoglycan" Glycobiology, 12(9), 117R-125R (2002).

(56) References Cited

OTHER PUBLICATIONS

Trowbridge, Janet M. et al., "Dermatan Sulfate Binds and Potentiates Activity of Keratinocyte Growth Factor (FGF-7)" The Journal of Biological Chemistry, 277(45), 42815-42820 (2002).
U.S. Appl. No. 13/318,710 Final Rejection dated Mar. 27, 2014.
U.S. Appl. No. 13/318,710 Non-Final Rejection dated Aug. 21, 2013.
U.S. Appl. No. 12/934,551 Non-Final Rejection dated Jun. 6, 2013.
U.S. Appl. No. 12/934,551 Final Rejection dated Jan. 17, 2014.
U.S. Appl. No. 13/806,438 Non-Final Rejection dated Mar. 3, 2014.
Uniprot/Trembl Q7Z4J1, "Nonintegrin Platelet Receptor for Type I Collagen", Last Modified Feb. 10, 2009, Available on the Internet <URL: http://www.uniprot.org/uniprot/Q7Z4J1 &format=html.
Uniprotkb, "Decorin Precursor—Bas Taurus (Bovine)", Last Modified Sep. 1, 2009, Available on the Internet <URL: http://www.uniprot.org/uniprot/P21793>.
Velander, Patrik et al., "Impaired wound healing in an acute diabetic pig model and the effects of local hyperglycemia" Wound Rep Reg, 16, 288-93 (2008).
Vogel, Kathryn G. et al., "Specific. inhibition of type I and type II collagen fibrillogenesis by the small proteoglycan of tendon" Biochem J, 223, 587-597 (1984).
Wang, et al., "Venous stenosis in a pig arteriovenous fistula model—anatomy, mechanisms and cellular phenotypes" Nephrol Dial Transplace, 23:525-533 (2008).
Wang, JianFei et al., "Deep dermal fibroblasts contribute to hypertrophic scarring" Laboratory Investigation, 88, 1278-1290 (2008).
Wang, Kai, et al., "Platelet, Not Endothelial, P-Selectin Is Required for Neointimal Formation After Vascular Injury", Arterioscler Thromb. Vase. Biol., No. 25, pp. 1584-1589 (2005).
Widgerow, Alan D. et al., "Multimodality Scar Management Program" Aesth Plast Surg, 33, 533-543 (2009).
Williams, et al; "Collagen fibril formation." J. Biol. Chem., 253(18), 6578-6585 (1978).
Wysocki, Annette B. et al., "Wound Fluid from Chronic Leg Ulcers Contains Elevated Levels of Metalloproteinases MMP-2 and MMP-9" The Society for Investigative Dematology, Inc., 101(1), 64-68 (1993).
Zhu, Kathy Q. et al, "Further similarities between cutaneous scarring in the female, red Duroc pig and human hypertrophic scarring" Burns, 30, 518-530 (2004).
Zhu, Kathy Q. et al., "Review of the female Duroc/Yorkshire pig model of human fibroproliferative scarring" Wound Rep. Reg., 15, S32-S39 (2007).
Zhu, Kathy Q. et al., "The female, red Duroc pig as an animal model of hypertrophic scarring and the potential role of the cones of skin" Burns, 29, 649-664 (2003).
Zustiak, S. P. et al. Influence of cell-adhesive peptide ligands on poly(ethylene glycol) hydrogel physical, mechanical and transport properties. Acta Biomaterialia, 6(9), 3404-14 (2010).
Basser, Peter J. et al., "Mechanical Properties of the Collagen Network in Human Articular Cartilage as Measured by Osmotic Stress Technique" Archives of Biochemistry and Biophysics, 351(2), 207-219 (1998).
Maroudas, A, "Balance between Swelling pressure and collagen tension in normal and degenerate cartilage" Nature, 260, 808-809 (1976).
Christner, J.E. "Studies on the properties of the inextricable proteoglycans from bovine nasal cartilage" J. Biol. Chem. 258, 14335-14341 (1983).
Hollander, Anthony P. et al., "Increased Damage to Type II Collagen in Osteoarthritic Articular Cartilage Detected by a New Immunassay" J. Clin. Invest., 93, 1722-1732 (1994).
Knudson, Cheryl B. et al., "Cartilage Proteoglycans" Cell & Developmental Biology, 12, 69-78 (2001).
Pratta, Michael A. et al., "Glycobiology and Extracellular Matrices: Aggrecan Protects Cartilage Collagens from Proteolytic Cleavage" J. Biol. Chem., 278(46), 45539-45545 (2003).
Madsen, Suzi Hoegh et al., "Aggrecanase- and matrix metalloproteinase-mediated aggrecan degradation is associated with different molecular characteristics of aggrecan and separated in time ex vivo" Biomarkers, 15(3) 266-276 (2010).
Sharma, Shaili et al., "Biomimetic Aggrecan Reduces Cartilage Extracellular Matrix From Degradation and Lowers Catabolic Activity in Ex Vivo and In Vivo Modelsa" Macromolecular Bioscience, DOI 10.1002, 1-10 (2013).
Schmitz, Ian et al., "Hyaluronan oligosaccharide treatment of chondrocytes stimulates expression of both HAS-2 and MMP-3, but by different signaling pathways" Osteoarthritis Cartilage 18(3) 447-454 (2010).
Klatt, Andreas R. et al., "A Critical Role for Collagen II in Cartilage Matrix Degradation: Collagen II Induces Pro-Inflammatory Cytokines and MMPs in Primary Human Chondrocytes" J. Orthop Res (27) 65-70 (2009).
Kapoor, Mohit et al., "role of proinflammatory cytokines in the pathophysiology of osteoarthritis" Nat. Rev. Rheumatol, 7, 33-42 (2011).
Lee, Seulki et al., "Dark Quenched Matrix Metalloproteinase Fluorogenic Probe for Imaging Osteoarthritis Development in Vivo" Bioconjugate Chemistry, 19(9), 1743-1747 (2008).
Lee, Seulki et al., "Polymeric Nanoparticle-Based Activatable Near-Infrared Nanosensor for Protease Determination In Vivo" Nano Lett., 9(12), 4412-4416 (2009).
Gerwin, Nicole "Intraarticular drug delivery in osteoarthritis" Advanced Drug Delivery Reviews, 58, 226-242 (2006).
Rutjes, Anne et al., "Viscosupplementation for Osteoarthritis of the Knee: A Systematic Review and Meta-analysis" Ann Intern Med., (157), 180-191 (2012).
Masuko, Kayo et al., "Anti-inflammatory effects of hyaluronan in arthritis therapy: Not just for viscosity" International Journal of General Medicine, 2, 77-81 (2009).
Ghosh, Peter et al., "The Effects of Intraarticular Administration of Hyaluronan in a Model of Early Osteoarthritis in Sheep I. Gait Analysis and Radiological and Morphological Studies" Seminarsin Arthritisand Rheumatism, 22(6), 18-30 (1993).
Smith Jr., Gerald N. et al., "Effect of Intraarticular Hyaluronan Injection in Experimental Canine Osteoarthritis" Arthritis & Rheumatism, 41(6), 976-985 (1998).
Fraser, J. R. E. et al., "Hyaluronan: its nature, distribution, functions and turnover" Journal of Internal Medicine, 242, 27-33 (1997).
Kraus, Virgina B. et al., "The OARSI Histopathology Initiative—Recommendations for Histological Assessments of Osteoarthritis in the Guinea Pig" Osteoarthritis Cartilage, 18(Suppl 3), S35-S52 (2010).
A National Public Health Agenda for Osteoarthritis 2010, www.cdc.gov/arthritis/docs/OAagenda.pdf (2010).
Madry, Henning et al., "Biological aspects of early osteoarthritis" Knee Surg Sports Traumator Arthrosc, 20, 407-422 (2012).
Huang, K. et al., "Aggrecanase and Aggrecan Degradation in Osteoarthritis: a Review" The Journal of International Medical Research, 36, 1149-1160 (2008).
Nagase, Hideaki et al., "Review: Aggrecanases and cartilage matrix degradation" Arthritis Research & Therapy, 5(2) 94-103 (2003).
Umlauf, Daniel et al., "Cartilage biology, pathology, and repair" Cell. Mol. Life Sci., 67, 4197-4211 (2010).
Nia, Hadi Tavakoli et al., "High-Bandwidth AFM-Based Rheology Reveals that Cartilage is Most Sensitive to High Loading Rates at Early Stages of Impairment" Biophysical Journal, 104, 1529-1537 (2013).
Lee, Young Ho et al., "Effect of glucosamine or chondroitin sulfate on the osteoarthritis progression: a meta-analysis" Rheumatol Int., 30, 357-363 (2010).
Henrotin, Yves et al., "Intra-articular use of a medical device composed of hyaluronic acid and chondroitin sulfate (Structovial CS): effects on clinical, ultrasonographic and biological parameters" BMC Research Notes, 5(407), 1-7 (2012).
Mummert, Mark E. et al., "Development of a Peptide Inhibitor of Hyaluronan-mediated Leukocyte Trafficking" J. Exp. Med., 192(6), 769-779 (2000).
Martel-Pelletier, Johanne et al., "Review: Future therapeutics for osteoarthritis" Bone, 51, 297-311 (2012).
Carney, S.L. et al., "The Structure and Function of Cartilage Proteoglycans" Physiological Reviews, 68(3), 858-910 (1988).

(56) References Cited

OTHER PUBLICATIONS

Cremer, Michael A. et al., "The cartilage collagens: a review of their structure, organization, and role in the pathogenesis of experimental arthritis in animals and in human rheumatic disease" J Mol Med, 76, 275-288 (1998).

Nili, Nafiseh et al., "Decorin inhibition of PDGF-stimulated vascular smooth muscle cell function: potential mechanism for inhibition of intimal hyperplasia after balloon angioplasty," The American Journal of Pathology, (2003), 869-878.

Zhang Q, Filas BA, Roth R, et al., "Preservation of the structure of enzymatically-degraded bovine vitreous using synthetic proteoglycan mimics," Invest Ophthalmol Vis Sci. 2014;55:8153-8162. DOI:10.1167/iovs.14-14366.

Kirker, et al., "Glycosaminoglycan hydrogel films as bio-interactive dressings for wound healing" Biomaterials. Sep. 2002;23(17):3661-71.

Written Opinion of the International Searching Authority for PCT Application No. PCT/US2005/005244 dated Aug. 20, 2006.

Place, et al., "Synthesis and characterization of proteoglycan-mimetic graft copolymers with tunable glycosaminoglycan density" Biomacromolecules. Oct. 13, 2014;15(10):3772-80. doi: 10.1021/bm501045k. Epub Sep. 15, 2014.

Lee, H. J. et al. "Enhanced chondrogenesis of mesenchymal stem cells in collagen mimetic peptide-mediated microenvironment" Tissue Engineering Part A, 14(11) 1843-51 (2008).

Kiani, Chris et al., "Review: Structure and function of aggrecan" Cell Research 12(1), 19-32 (2002).

Ogden, David A., "Clinical responses to new and reprocessed hemodialyzers." Guide to Reprocessing of Hemodialyzers 87-97 (1986).

Paderi, "Design of collagen binding proteoglycan mimics." Thesis (Aug. 2008).

Paderi, John E., et al., "The Inhibition of Platelet Adhesion and Activation on Collagen During Balloon Angioplasty by Collagen-Binding Peptidoglycans" Biomaterials, 32, 2516-2523 (2011).

Pieper, J.S., et al., Development of tailor-made collagen-giycosaminoglycan matrices: EDC/NHS crosslinking, and ultrastructural aspects Biomaterials, 21, 581-593 (2000).

Pierce Biotechnology catalog (2005/2006), 3 pages.

Roth, Gerald J. et al; "Localization of binding sites within human von willebrand factor for monomeric type III collagen." Biochemistry 25, 8357-8361 (1986).

Santa Cruz Biotechnology listing for phosphate buffered saline (http://www.scbt.com/datasheet-362182.html, downloaded Feb. 10, 2014).

Saxena, Anil K. et al; "Enhancing the survival of tunneled haemodialysis catheters using an antibiotic lock in the elderly: a randomized, double blind clinical trial." Nephrology 11, 299-305 (2006).

Orbusneich, (2013), "About the Combo Dual Therapy Stent™ Design and Mechanism of Action The COMBO Dual Therapy Stent is coated abluminally with a drug elution matrix," G-70/0175 Rev 02, 2 pages, http://www.orbusneich.com/.

Van Neck, et al., (Mar. 30, 2012), "Heparan Sulfate Proteoglycan Mimetics Promote Tissue Regeneration: An Overview," Chapter 4 in J Davies (Ed.), Tissue Regeneration—From Basic Biology to Clinical Application, 69-92, InTech—Open Access Publisher, ISBN 978-953-51-0387-5, 520 pages.

\* cited by examiner

A

B

A

B

HYALURONIC ACID-BINDING SYNTHETIC PEPTIDOGLYCANS, PREPARATION, AND METHODS OF USE

CROSS-REFERENCE TO RELATED APPLICATIONS

This application is a U.S. national counterpart application of International Application Serial No. PCT/US2012/039404 filed May 24, 2012, which claims priority under 35 U.S.C. §119(e) to U.S. Provisional Application Ser. No. 61/489,602 filed May 24, 2011 and U.S. Provisional Application Ser. No. 61/550,621 filed Oct. 24, 2011. The disclosures of all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 17, 2014, is named 3220-227761_SL.txt and is 15,945 bytes in size.

TECHNICAL FIELD

This invention pertains to the field of hyaluronic acid-binding synthetic peptidoglycans and methods of forming and using the same.

BACKGROUND AND SUMMARY OF THE INVENTION

Articular cartilage is an important component for the protection of bones in the body. In particular, articular cartilage functions to protect articulating bones from damage by providing a near-frictionless surface for bone movement and also providing compressive strength to joints. Articular cartilage broadly includes an extracellular matrix (ECM) derived from three main components: a collagen scaffold, hyaluronic acid (HA), and aggrecan. The material composition of articular cartilage dictates the tissue's biological, chemical and mechanical properties. The extracellular matrix (ECM) of healthy cartilage is primarily composed of a network of collagen fibrils (15-22% wet weight type II collagen), proteoglycans (4-7% wet weight), glycoproteins, water (60-85%) and electrolytes, giving rise to a viscoelastic tissue with depth-dependent structural and mechanical anisotropy.

Cartilage degradation and wear is a hallmark of osteoarthritis (OA). During the initial stages of OA, aggrecan, a major proteoglycan in cartilage, is an early component to be degraded. The aggrecan monomer is a protein core with covalently attached glycosaminoglycan (GAG) side chains that bind to filamentous hyaluronic acid via globular domains and a link protein. Proteases, such as aggrecanases, cleave aggrecan at specific sites creating protein fragments and free GAG chains that are unable to rebind to HA. Instead, these free GAG chains are extruded from the matrix, which not only reduces compressive strength, but also initiates an increase in pro-inflammatory cytokines and matrix metalloproteases. The presence of aggrecan has been shown to reduce diffusion of proteases protecting underlying collagen fibers from proteolytic cleavage. Loss of aggrecan occurs even in normal cartilage and is not immediately correlated to OA. However, loss of type II collagen is considered an irreversible process, leading to precocious wear.

Osteoarthritis is the most common form of arthritis, affecting 27 million people in the US alone. The most prevalent symptoms of osteoarthritis include immense pain, stiffening in the joints, and tender and inflamed joints. Advanced stages of osteoarthritis can lead to complete degradation of the articular cartilage, causing immobility of joints and damage to the underlying bone. The direct costs of arthritis in the United States are estimated to be approximately $185.5 billion each year.

Although lifestyle changes and multiple medications are often used for the treatment of osteoarthritis, there has been little success in regeneration of defective cartilage and relieving the symptoms caused by the loss of cartilage. This inability to halt the progression of osteoarthritis and repair the existing damage typically leads to an invasive, end stage cartilage replacement procedure. Thus, an alternative treatment option for osteoarthritis is highly desired.

The present disclosure describes improved biomaterials for cartilage regeneration, including hyaluronic acid-binding synthetic peptidoglycans that can be utilized to restore damaged cartilage in an affected patient, along with methods of forming and using the synthetic peptidoglycans. Furthermore, the hyaluronic acid-binding synthetic peptidoglycans are designed to functionally mimic aggrecan, resist aggrecanase degradation, and limit proteolytic degradation. The absence of the native amino acid sequence seen in aggrecan makes these molecules less susceptible to proteolytic cleavage.

The following numbered embodiments are contemplated and are non-limiting:

1. A hyaluronic acid-binding synthetic peptidoglycan comprising a synthetic peptide conjugated to a glycan wherein the synthetic peptide comprises a hyaluronic acid-binding sequence.
2. The synthetic peptidoglycan of clause 1 wherein the synthetic peptide comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.
3. The synthetic peptidoglycan of clause 1 or clause 2 wherein the synthetic peptide comprises an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |

-continued

| | |
|---|---|
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

4. The synthetic peptidoglycan of any one of clauses 1 to 3 wherein the glycan is selected from the group consisting of dextran, chondroitin, chondroitin sulfate, dermatan, dermatan sulfate, heparan, heparin, keratin, keratan sulfate, and hyaluronic acid.

5. The synthetic peptidoglycan of any one of clauses 1 to 4 wherein the glycan is selected from the group consisting of chondroitin sulfate and keratan sulfate.

6. The synthetic peptidoglycan of any one of clauses 1 to 5 wherein the synthetic peptidoglycan is resistant to aggrecanase.

7. The synthetic peptidoglycan of any one of clauses 1 to 6 wherein the synthetic peptidoglycan is lyophilized.

8. A compound of formula $P_nG_x$ wherein n is 1 to 20;
   wherein x is 1 to 20;
   wherein P is a synthetic peptide of about 5 to about 40 amino acids comprising a hyaluronic acid binding sequence; and
   wherein G is a glycan.

9. A compound of formula $(P_nL)_xG$ wherein n is 1 to 20;
   wherein x is 1 to 20;
   wherein P is a synthetic peptide of about 5 to about 40 amino acids comprising a hyaluronic acid binding sequence;
   wherein L is a linker; and wherein G is a glycan.

10. A compound of formula $P(LG_n)_x$ wherein n is 1 to 20;
    wherein x is 1 to 20;
    wherein P is a synthetic peptide of about 5 to about 40 amino acids comprising a hyaluronic acid binding sequence;
    wherein L is a linker; and
    wherein G is a glycan.

11. A compound of formula $P_nG_x$ wherein n is MWG/1000;
    wherein MWG is the molecular weight of G rounded to the nearest 1 kDa;
    wherein x is 1 to 20;
    wherein P is a synthetic peptide of about 5 to about 40 amino acids comprising a hyaluronic acid binding sequence; and
    wherein G is a glycan.

12. A compound of formula $(P_nL)_xG$ wherein n is MWG/1000;
    wherein MWG is the molecular weight of G rounded to the nearest 1 kDa;
    wherein x is 1 to 20;
    wherein P is a synthetic peptide of about 5 to about 40 amino acids comprising a hyaluronic acid binding sequence;
    wherein L is a linker; and wherein G is a glycan.

13. The compound of any one of clauses 8 to 12 wherein the synthetic peptide comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.

14. The compound of any one of clauses 8 to 13 wherein the synthetic peptide comprises an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |

-continued

| | |
|---|---|
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

15. The compound of any one of clauses 8 to 14 wherein the glycan is selected from the group consisting of dextran, chondroitin, chondroitin sulfate, dermatan, dermatan sulfate, heparan, heparin, keratin, keratan sulfate, and hyaluronic acid.

16. The compound of any one of clauses 8 to 15 wherein the glycan is selected from the group consisting of chondroitin sulfate and keratan sulfate.

17. The compound of any one of clauses 8 to 16 wherein the synthetic peptidoglycan is resistant to aggrecanase.

18. An engineered collagen matrix comprising polymerized collagen, hyaluronic acid, and a hyaluronic acid-binding synthetic peptidoglycan.

19. The engineered collagen matrix of clause 18 wherein the collagen is selected from the group consisting of type I collagen, type II collagen, type III collagen, type IV collagen, type IX collagen, type XI collagen, and combinations thereof 20. The engineered collagen matrix of clause 18 or 19 wherein the peptide component of the synthetic peptidoglycan comprises an amino acid sequence of the formula B1-X1-X2-X3-X4-X5-X6-X7-X8-B2 (SEQ ID NO: 1),
wherein X8 is present or is not present,
wherein B1 is a basic amino acid,
wherein B2 is a basic amino acid, and
wherein X1-X8 are non-acidic amino acids.

21. The engineered collagen matrix of any one of clauses 18 or 20 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |

-continued

| | |
|---|---|
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

22. The engineered collagen matrix of any one of clauses 18 to 21 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.

23. The engineered collagen matrix of any one of clauses 18 to 22 wherein the glycan component of the synthetic peptidoglycan is selected from the group consisting of chondroitin sulfate and keratan sulfate.

24. The engineered collagen matrix of any one of clauses 18 to 23 wherein the synthetic peptidoglycan is resistant to aggrecanase.

25. The engineered collagen matrix of any one of clauses 18 to 24 wherein the matrix is effective as a tissue graft.

26. The engineered collagen matrix of clause 25 wherein the tissue graft is implanted into a patient.

27. The engineered collagen matrix of any one of clauses 18 to 24 wherein the matrix is in the form of a gel.
28. The engineered collagen matrix of clause 27 wherein the gel is administered to a patient by injection.
29. The engineered collagen matrix of any one of clauses 18 to 24 wherein the matrix is effective as a composition for in vitro culture of cells.
30. The engineered collagen matrix of clause 29 wherein the matrix further comprises an exogenous population of cells.
31. The engineered collagen matrix of clause 30 wherein the cells are selected from the group consisting of chondrocytes and stem cells.
32. The engineered collagen matrix of clause 31 wherein the stem cells are selected from the group consisting of osteoblasts, osteogenic cells, and mesenchymal stem cells.
33. The engineered collagen matrix of any one of clauses 18 to 32 further comprising one or more nutrients.
34. The engineered collagen matrix of any one of clauses 18 to 33 further comprising one or more growth factors.
35. The engineered collagen matrix of any one of clauses 18 to 34 wherein the matrix is sterilized.
36. A composition for in vitro culture of chondrocytes or stem cells comprising a hyaluronic acid-binding synthetic peptidoglycan.
37. The composition of clause 36 wherein the peptide component of the synthetic peptidoglycan comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.
38. The composition of clause 36 or clause 37 wherein the peptide component of the synthetic peptidoglycan comprises an amino acid sequence selected from the group consisting of:

```
GAHWQFNALTVRGG;              (SEQ ID NO: 2)
GDRRRRRMWHRQ;                (SEQ ID NO: 3)
GKHLGGKHRRSR;                (SEQ ID NO: 4)
RGTHHAQKRRS;                 (SEQ ID NO: 5)
RRHKSGHIQGSK;                (SEQ ID NO: 6)
SRMHGRVRGRHE;                (SEQ ID NO: 7)
RRRAGLTAGRPR;                (SEQ ID NO: 8)
RYGGHRTSRKWV;                (SEQ ID NO: 9)
RSARYGHRRGVG;                (SEQ ID NO: 10)
GLRGNRRVFARP;                (SEQ ID NO: 11)
SRGQRGRLGKTR;                (SEQ ID NO: 12)
DRRGRSSLPKLAGPVEFPDRKIKGRR;  (SEQ ID NO: 13)
RMRRKGRVKHWG;                (SEQ ID NO: 14)
RGGARGRHKTGR;                (SEQ ID NO: 15)
TGARQRGLQGGWGPRHLRGKDQPPGR;  (SEQ ID NO: 16)
RQRRRDLTRVEG;                (SEQ ID NO: 17)
STKDHNRGRRNVGPVSRSTLRDPIRR;  (SEQ ID NO: 18)
RRIGHQVGGRRN;                (SEQ ID NO: 19)
RLESRAAGQRRA;                (SEQ ID NO: 20)
GGPRRHLGRRGH;                (SEQ ID NO: 21)
VSKRGHRRTAHE;                (SEQ ID NO: 22)
RGTRSGSTR;                   (SEQ ID NO: 23)
RRRKKIQGRSKR;                (SEQ ID NO: 24)
RKSYGKYQGR;                  (SEQ ID NO: 25)
KNGRYSISR;                   (SEQ ID NO: 26)
RRRCGQKKK;                   (SEQ ID NO: 27)
KQKIKHVVKLK;                 (SEQ ID NO: 28)
KLKSQLVKRK;                  (SEQ ID NO: 29)
RYPISRPRKR;                  (SEQ ID NO: 30)
KVGKSPPVR;                   (SEQ ID NO: 31)
KTFGKMKPR;                   (SEQ ID NO: 32)
RIKWSRVSK;                   (SEQ ID NO: 33)
and
KRTMRPTRR.                   (SEQ ID NO: 34)
```

In each of the above peptide embodiments, the peptide may have a glycine-cysteine (GC) attached to the C-terminus of the peptide, or a glycine-cysteine-glycine (GCG) attached to the N-terminus.

39. The composition of any one of clauses 36 to 38 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
40. The composition of any one of clauses 36 to 39 wherein the glycan component of the synthetic peptidoglycan is selected from the group consisting of chondroitin sulfate and keratan sulfate.
41. The composition of any one of clauses 36 to 40 wherein the synthetic peptidoglycan is resistant to aggrecanase.
42. The composition of any one of clauses 36 to 41 wherein the stem cells are selected from the group consisting of osteoblasts, osteogenic cells, and mesenchymal stem cells.
43. The composition of any one of clauses 36 to 42 further comprising one or more nutrients.
44. The composition of any one of clauses 36 to 43 further comprising one or more growth factors.
45. The composition of any one of clauses 36 to 44 wherein the composition is sterilized.
46. An additive for a biomaterial cartilage or bone replacement composition comprising a hyaluronic acid-binding synthetic peptidoglycan for addition to an existing biomaterial cartilage or bone replacement material.
47. The additive of clause 46 wherein the peptide component of the synthetic peptidoglycan comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.

48. The additive of clause 46 or clause 47 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK;<br>and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

49. The additive of any one of clauses 46 to 48 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.

50. The additive of any one of clauses 46 to 49 wherein the glycan is selected from the group consisting of chondroitin sulfate and keratan sulfate.

51. The additive of any one of clauses 46 to 50 wherein the synthetic peptidoglycan is resistant to aggrecanase.

52. A method of treatment for arthritis in a patient, said method comprising the step of administering to the patient a hyaluronic acid-binding synthetic peptidoglycan, wherein the synthetic peptidoglycan reduces a symptom associated with the arthritis.

53. The method of clause 52 wherein the peptide component of the synthetic peptidoglycan comprises an amino acid sequence of the formula B1-X1-X2-X3-X4-X5-X6-X7-X8-B2 (SEQ ID NO: 1),
wherein X8 is present or is not present,
wherein B1 is a basic amino acid,
wherein B2 is a basic amino acid, and
wherein X1-X8 are non-acidic amino acids.

54. The method of clause 52 or clause 53 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |

| | |
|---|---|
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

55. The method of any one of clauses 52 to 54 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
56. The method of any one of clauses 52 to 55 wherein the glycan is selected from the group consisting of chondroitin sulfate and keratan sulfate.
57. The method of any one of clauses 52 to 56 wherein the synthetic peptidoglycan is resistant to aggrecanase.
58. The method of any one of clauses 52 to 57 wherein the arthritis is osteoarthritis.
59. The method of any one of clauses 52 to 57 wherein the arthritis is rheumatoid arthritis.
60. The method of any one of clauses 52 to 59 wherein the synthetic peptidoglycan is administered to the patient by injection.
61. The method of clause 60 wherein the injection is an intraarticular injection.
62. The method of clause 60 wherein the injection is into a joint capsule of the patient.
63. The method of any one of clauses 52 to 62 wherein the synthetic peptidoglycan is administered using a needle or a device for infusion.
64. The method of any one of clauses 52 to 63 wherein the synthetic peptidoglycan acts as a lubricant.
65. The method of any one of clauses 52 to 64 wherein the synthetic peptidoglycan prevents bone on bone articulation or prevents cartilage loss.
66. A method of preparing a biomaterial or bone cartilage replacement, said method comprising the step of combining the synthetic peptidoglycan and an existing biomaterial or bone cartilage replacement material.
67. The method of clause 66 wherein the peptide component of the synthetic peptidoglycan comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.
68. The method of clause 66 or clause 67 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

69. The method of any one of clauses 66 to 68 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
70. The method of any one of clauses 66 to 69 wherein the glycan is selected from the group consisting of chondroitin sulfate and keratan sulfate.

71. The method of any one of clauses 66 to 70 wherein the synthetic peptidoglycan is resistant to aggrecanase.
72. A method of reducing or preventing hyaluronic acid degradation in a patient, said method comprising administering to the patient a hyaluronic acid-binding synthetic peptidoglycan.
73. The method of clause 72 wherein the peptide component of the synthetic peptidoglycan comprises an amino acid sequence of the formula B1-X1-X2-X3-X4-X5-X6-X7-X8-B2 (SEQ ID NO: 1),
wherein X8 is present or is not present,
wherein B1 is a basic amino acid,
wherein B2 is a basic amino acid, and
wherein X1-X8 are non-acidic amino acids.
74. The method of clause 72 or clause 73 wherein the peptide component of the synthetic peptidoglycan comprises an amino acid sequence selected from the group consisting of:

```
GAHWQFNALTVRGG;              (SEQ ID NO: 2)
GDRRRRRMWHRQ;                (SEQ ID NO: 3)
GKHLGGKHRRSR;                (SEQ ID NO: 4)
RGTHHAQKRRS;                 (SEQ ID NO: 5)
RRHKSGHIQGSK;                (SEQ ID NO: 6)
SRMHGRVRGRHE;                (SEQ ID NO: 7)
RRRAGLTAGRPR;                (SEQ ID NO: 8)
RYGGHRTSRKWV;                (SEQ ID NO: 9)
RSARYGHRRGVG;                (SEQ ID NO: 10)
GLRGNRRVFARP;                (SEQ ID NO: 11)
SRGQRGRLGKTR;                (SEQ ID NO: 12)
DRRGRSSLPKLAGPVEFPDRKIKGRR;  (SEQ ID NO: 13)
RMRRKGRVKHWG;                (SEQ ID NO: 14)
RGGARGRHKTGR;                (SEQ ID NO: 15)
TGARQRGLQGGWGPRHLRGKDQPPGR;  (SEQ ID NO: 16)
RQRRRDLTRVEG;                (SEQ ID NO: 17)
STKDHNRGRRNVGPVSRSTLRDPIRR;  (SEQ ID NO: 18)
RRIGHQVGGRRN;                (SEQ ID NO: 19)
RLESRAAGQRRA;                (SEQ ID NO: 20)
GGPRRHLGRRGH;                (SEQ ID NO: 21)
VSKRGHRRTAHE;                (SEQ ID NO: 22)
RGTRSGSTR;                   (SEQ ID NO: 23)
RRRKKIQGRSKR;                (SEQ ID NO: 24)
RKSYGKYQGR;                  (SEQ ID NO: 25)
KNGRYSISR;                   (SEQ ID NO: 26)
RRRCGQKKK;                   (SEQ ID NO: 27)
KQKIKHVVKLK;                 (SEQ ID NO: 28)
KLKSQLVKRK;                  (SEQ ID NO: 29)
RYPISRPRKR;                  (SEQ ID NO: 30)
KVGKSPPVR;                   (SEQ ID NO: 31)
KTFGKMKPR;                   (SEQ ID NO: 32)
RIKWSRVSK;                   (SEQ ID NO: 33)
and
KRTMRPTRR.                   (SEQ ID NO: 34)
```

In each of the above peptide embodiments, the peptide may have a glycine-cysteine (GC) attached to the C-terminus of the peptide, or a glycine-cysteine-glycine (GCG) attached to the N-terminus 75. The method of any one of clauses 72 to 74 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
76. The method of any one of clauses 72 to 75 wherein the glycan is selected from the group consisting of chondroitin sulfate and keratan sulfate.
77. The method of any one of clauses 72 to 76 wherein the synthetic peptidoglycan is resistant to aggrecanase.
78. The method of any one of clauses 72 to 77 wherein the synthetic peptidoglycan is administered to the patient by injection.
79. The method of clause 78 wherein the injection is an intraarticular injection.
80. The method of clause 78 wherein the injection is into a joint capsule of the patient.
81. The method of any one of clauses 72 to 80 wherein the rate of hyaluronic acid degradation is reduced.
82. A method for correcting or modifying a tissue defect in a patient comprising
administering into the tissue defect a hyaluronic acid-binding synthetic peptidoglycan wherein the defect is corrected or modified.
83. The method of clause 82 wherein the peptide component of the synthetic peptidoglycan comprises an amino acid sequence of the formula B1-X1-X2-X3-X4-X5-X6-X7-X8-B2 (SEQ ID NO: 1),
wherein X8 is present or is not present,
wherein B1 is a basic amino acid,
wherein B2 is a basic amino acid, and
wherein X1-X8 are non-acidic amino acids.
84. The method of clause 82 or clause 83 wherein the peptide component of the synthetic peptidoglycan comprises an amino acid sequence selected from the group consisting of:

```
GAHWQFNALTVRGG;              (SEQ ID NO: 2)
GDRRRRRMWHRQ;                (SEQ ID NO: 3)
GKHLGGKHRRSR;                (SEQ ID NO: 4)
RGTHHAQKRRS;                 (SEQ ID NO: 5)
RRHKSGHIQGSK;                (SEQ ID NO: 6)
SRMHGRVRGRHE;                (SEQ ID NO: 7)
RRRAGLTAGRPR;                (SEQ ID NO: 8)
RYGGHRTSRKWV;                (SEQ ID NO: 9)
RSARYGHRRGVG;                (SEQ ID NO: 10)
```

-continued

| | |
|---|---|
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

85. The method of any one of clauses 82 to 84 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.

86. The method of any one of clauses 82 to 85 wherein the glycan is selected from the group consisting of chondroitin sulfate and keratan sulfate.

87. The method of any one of clauses 82 to 86 wherein the synthetic peptidoglycan is resistant to aggrecanase.

88. The method of any one of clauses 82 to 87 wherein the synthetic peptidoglycan is administered to the patient by injection.

89. The method of clause 88 wherein the injection is subcutaneous.

90. The method of any one of clauses 82 to 89 wherein the defect is a cosmetic defect.

91. A dermal filler comprising a hyaluronic acid-binding synthetic peptidoglycan.

92. The dermal filler of clause 91 wherein the peptide component of the synthetic peptidoglycan comprises an amino acid sequence of the formula B1-X1-X2-X3-X4-X5-X6-X7-X8-B2, wherein X8 is present or is not present, wherein B1 is a basic amino acid, wherein B2 is a basic amino acid, and wherein X1-X8 are non-acidic amino acids.

93. The dermal filler of clause 91 or clause 92 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine (GC) attached to the C-terminus of the peptide, or a glycine-cysteine-glycine (GCG) attached to the N-terminus.

94. The dermal filler of any one of clauses 91 to 93 further comprising hyaluronic acid.
95. A method of reducing or preventing collagen degradation, said method comprising the steps of
    contacting a hyaluronic acid-binding synthetic peptidoglycan with hyaluronic acid in the presence of collagen, and
    reducing or preventing collagen degradation.
96. The method of clause 95 wherein the peptide component of the synthetic peptidoglycan comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.
97. The method of clause 95 or clause 96 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |

-continued

| | |
|---|---|
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

98. The method of any one of clauses 95 to 97 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
99. The method of any one of clauses 95 to 98 wherein the glycan is selected from the group consisting of chondroitin sulfate and keratan sulfate.
100. The method of any one of clauses 95 to 99 wherein the synthetic peptidoglycan is resistant to aggrecanase.
101. The method of any one of clauses 95 to 100 wherein the rate of hyaluronic acid degradation is reduced.
102. A method of increasing pore size in an engineered collagen matrix, said method comprising the steps of
    combining collagen, hyaluronic acid, and a hyaluronic acid-binding synthetic peptidoglycan, and
    increasing the pore size in the matrix.
103. The method of clause 102 wherein the peptide component of the synthetic peptidoglycan comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.
104. The method of clause 102 or clause 103 wherein the peptide component of the synthetic peptidoglycan comprises an amino acid sequence selected from the group consisting of:

| | |
|---|---|
| GAHWQFNALTVRGG; | (SEQ ID NO: 2) |
| GDRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |

```
RMRRKGRVKHWG;                   (SEQ ID NO: 14)
RGGARGRHKTGR;                   (SEQ ID NO: 15)
TGARQRGLQGGWGPRHLRGKDQPPGR;     (SEQ ID NO: 16)
RQRRRDLTRVEG;                   (SEQ ID NO: 17)
STKDHNRGRRNVGPVSRSTLRDPIRR;     (SEQ ID NO: 18)
RRIGHQVGGRRN;                   (SEQ ID NO: 19)
RLESRAAGQRRA;                   (SEQ ID NO: 20)
GGPRRHLGRRGH;                   (SEQ ID NO: 21)
VSKRGHRRTAHE;                   (SEQ ID NO: 22)
RGTRSGSTR;                      (SEQ ID NO: 23)
RRRKKIQGRSKR;                   (SEQ ID NO: 24)
RKSYGKYQGR;                     (SEQ ID NO: 25)
KNGRYSISR;                      (SEQ ID NO: 26)
RRRCGQKKK;                      (SEQ ID NO: 27)
KQKIKHVVKLK;                    (SEQ ID NO: 28)
KLKSQLVKRK;                     (SEQ ID NO: 29)
RYPISRPRKR;                     (SEQ ID NO: 30)
KVGKSPPVR;                      (SEQ ID NO: 31)
KTFGKMKPR;                      (SEQ ID NO: 32)
RIKWSRVSK;                      (SEQ ID NO: 33)
and
KRTMRPTRR.                      (SEQ ID NO: 34)
```

105. The method of any one of clauses 102 to 104 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
106. The method of any one of clauses 102 to 105 wherein the glycan is selected from the group consisting of chondroitin sulfate and keratan sulfate.
107. The method of any one of clauses 102 to 106 wherein the synthetic peptidoglycan is resistant to aggrecanase.
108. The method of any one of clauses 102 to 107 wherein the matrix is sterilized.
109. The method of any one of clauses 102 to 108 wherein the matrix further comprises chondrocytes or stem cells.
110. The method of clause 109 wherein the stem cells are selected from the group consisting of osteoblasts, osteogenic cells, and mesenchymal stem cells.
111. The method of any one of clauses 102 to 110 wherein the matrix further comprises one or more nutrients.
112. The method of any one of clauses 102 to 111 wherein the matrix further comprises one or more growth factors.
113. A method of reducing or preventing chondroitin sulfate degradation, said method comprising the steps of contacting a hyaluronic acid-binding synthetic peptidoglycan with hyaluronic acid in the presence of collagen, and
reducing or preventing chondroitin sulfate degradation.
114. The method of clause 113 wherein the peptide component of the synthetic peptidoglycan comprises an amino acid sequence of the formula B1-X1-X2-X3-X4-X5-X6-X7-X8-B2 (SEQ ID NO: 1),
wherein X8 is present or is not present,
wherein B1 is a basic amino acid,
wherein B2 is a basic amino acid, and
wherein X1-X8 are non-acidic amino acids.
115. The method of clause 113 or clause 114 wherein the peptide component of the synthetic peptidoglycan comprises an amino acid sequence selected from the group consisting of:

```
GAHWQFNALTVRGG;                 (SEQ ID NO: 2)
GDRRRRRMWHRQ;                   (SEQ ID NO: 3)
GKHLGGKHRRSR;                   (SEQ ID NO: 4)
RGTHHAQKRRS;                    (SEQ ID NO: 5)
RRHKSGHIQGSK;                   (SEQ ID NO: 6)
SRMHGRVRGRHE;                   (SEQ ID NO: 7)
RRRAGLTAGRPR;                   (SEQ ID NO: 8)
RYGGHRTSRKWV;                   (SEQ ID NO: 9)
RSARYGHRRGVG;                   (SEQ ID NO: 10)
GLRGNRRVFARP;                   (SEQ ID NO: 11)
SRGQRGRLGKTR;                   (SEQ ID NO: 12)
DRRGRSSLPKLAGPVEFPDRKIKGRR;     (SEQ ID NO: 13)
RMRRKGRVKHWG;                   (SEQ ID NO: 14)
RGGARGRHKTGR;                   (SEQ ID NO: 15)
TGARQRGLQGGWGPRHLRGKDQPPGR;     (SEQ ID NO: 16)
RQRRRDLTRVEG;                   (SEQ ID NO: 17)
STKDHNRGRRNVGPVSRSTLRDPIRR;     (SEQ ID NO: 18)
RRIGHQVGGRRN;                   (SEQ ID NO: 19)
RLESRAAGQRRA;                   (SEQ ID NO: 20)
GGPRRHLGRRGH;                   (SEQ ID NO: 21)
VSKRGHRRTAHE;                   (SEQ ID NO: 22)
RGTRSGSTR;                      (SEQ ID NO: 23)
RRRKKIQGRSKR;                   (SEQ ID NO: 24)
RKSYGKYQGR;                     (SEQ ID NO: 25)
KNGRYSISR;                      (SEQ ID NO: 26)
RRRCGQKKK;                      (SEQ ID NO: 27)
KQKIKHVVKLK;                    (SEQ ID NO: 28)
KLKSQLVKRK;                     (SEQ ID NO: 29)
RYPISRPRKR;                     (SEQ ID NO: 30)
KVGKSPPVR;                      (SEQ ID NO: 31)
KTFGKMKPR;                      (SEQ ID NO: 32)
RIKWSRVSK;                      (SEQ ID NO: 33)
and
KRTMRPTRR.                      (SEQ ID NO: 34)
```

116. The method of any one of clauses 113 to 115 wherein the glycan component of the synthetic peptidoglycan is selected from the group consisting of dextran, chondroitin, chondroitin sulfate, dermatan, dermatan sulfate, heparan, heparin, keratin, keratan sulfate, and hyaluronic acid.
117. The method of any one of clauses 113 to 116 wherein the glycan is selected from the group consisting of chondroitin sulfate and keratan sulfate.
118. The method of any one of clauses 113 to 117 wherein the synthetic peptidoglycan is resistant to aggrecanase.
119. The method of any one of clauses 113 to 118 wherein the rate of chondroitin sulfate degradation is reduced.
120. The synthetic peptidoglycan, compound, engineered collagen matrix, composition, additive, method, or dermal filler of any of the preceding clauses wherein the peptide component of the synthetic peptidoglycan has a glycine-cysteine (GC) attached to the C-terminus of the peptide.
121. The synthetic peptidoglycan, compound, engineered collagen matrix, composition, additive, method, or dermal filler of any of the preceding clauses wherein the peptide component of the synthetic peptidoglycan has a glycine-cysteine-glycine (GCG) attached to the N-terminus of the peptide.
122. The synthetic peptidoglycan, compound, engineered collagen matrix, composition, additive, method, or dermal filler of any of the preceding clauses wherein the synthetic peptidoglycan is resistant to matrix metallo proteases.
123. The synthetic peptidoglycan, compound, engineered collagen matrix, composition, additive, method, or dermal filler of clause 122 wherein the matrix metallo protease is aggrecanase.
124. The synthetic peptidoglycan, compound, engineered collagen matrix, composition, additive, method, or dermal filler of any of the preceding clauses wherein the dosage of the synthetic peptidoglycan is in a concentration ranging from about 0.01 uM to about 100 uM.
125. The synthetic peptidoglycan, compound, engineered collagen matrix, composition, additive, method, or dermal filler of any of the preceding clauses wherein the dosage of the synthetic peptidoglycan is in a concentration ranging from about 0.1 uM to about 10 uM.

DETAILED DESCRIPTION OF THE ILLUSTRATIVE EMBODIMENTS

Figure 1:
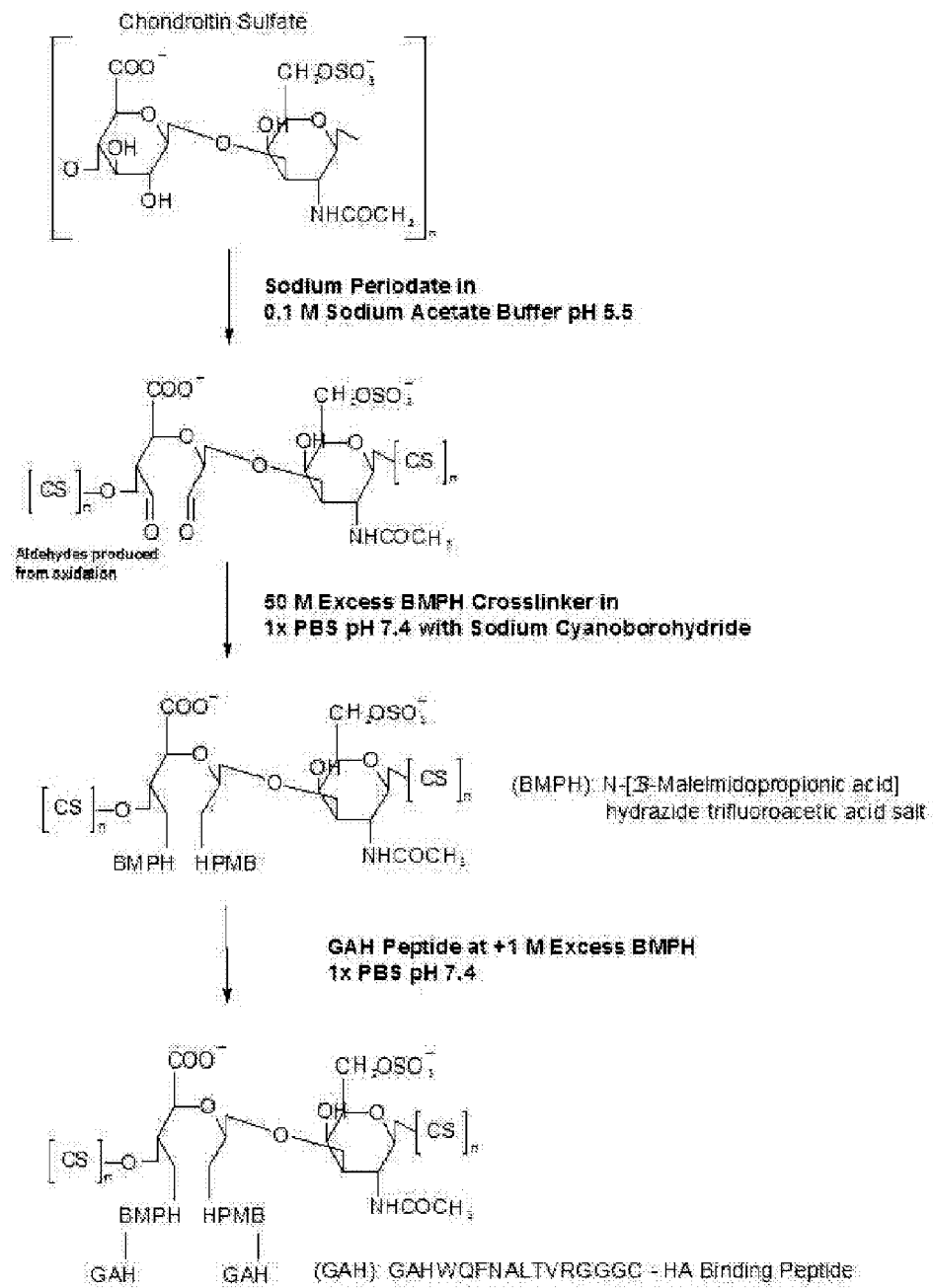
FIG. 1 shows a reaction schematic for the production of an embodiment of the hyaluronic acid-binding synthetic peptidoglycan. Reaction steps are detailed in bold font.

As used herein, a "hyaluronic acid-binding synthetic peptidoglycan" means a synthetic peptide conjugated to a glycan where the peptide comprises a hyaluronic acid-binding sequence.

Various embodiments of the invention are described herein as follows. In one embodiment described herein, a hyaluronic acid-binding synthetic peptidoglycan is provided. The hyaluronic acid-binding synthetic peptidoglycan comprises a synthetic peptide conjugated to a glycan wherein the synthetic peptide comprises a hyaluronic acid-binding sequence.

In another embodiment, a compound of the formula $P_nG_x$ is described wherein n is 1 to 20; wherein x is 1 to 20; wherein P is a synthetic peptide of about 5 to about 40 amino acids comprising a hyaluronic acid binding sequence; and wherein G is a glycan.

In yet another embodiment, a compound of the formula $(P_nL)_xG$ is described
 wherein n is 1 to 20;
 wherein x is 1 to 20;
 wherein P is a synthetic peptide of about 5 to about 40 amino acids comprising a hyaluronic acid binding sequence;
 wherein L is a linker; and
 wherein G is a glycan.

In another embodiment, a compound of the formula $P(LG_n)_x$ is described
    wherein n is 1 to 20;
    wherein x is 1 to 20;
    wherein P is a synthetic peptide of about 5 to about 40 amino acids comprising a hyaluronic acid binding sequence;
    wherein L is a linker; and wherein G is a glycan.

In yet another embodiment, a compound of the formula $P_nG_x$ is described
    wherein n is MWG/1000;
    wherein MWG is the molecular weight of G rounded to the nearest 1 kDa;
    wherein x is 1 to 20;
    wherein P is a synthetic peptide of about 5 to about 40 amino acids comprising a hyaluronic acid binding sequence; and
    wherein G is a glycan.

In another embodiment, a compound of the formula $(P_nL)_xG$ is described
    wherein n is MWG/1000;
    wherein MWG is the molecular weight of G rounded to the nearest 1 kDa;
    wherein x is 1 to 20;
    wherein P is a synthetic peptide of about 5 to about 40 amino acids comprising a hyaluronic acid binding sequence;
    wherein L is a linker; and
    wherein G is a glycan.

For purposes of this disclosure, the hyaluronic acid-binding synthetic peptidoglycans and compounds described in the preceding paragraphs are collectively referred to as "hyaluronic acid-binding synthetic peptidoglycans" or "synthetic peptidoglycans."

In each of the above peptide embodiments, the synthetic peptidoglycan may comprise 5-15 peptide molecules (n is 5-15), 5-20 peptide molecules (n is 5-20), 1-20 peptide molecules (n is 1-20), or 1-25 peptide molecules (n is 1-25). In one embodiment, n is selected from the group consisting of 1, 2, 3, 4, 5, 6, 7, 8, 9, 10, 11, 12, 13, 14, 15, 16, 17, 18, 19, 20, 21, 22, 23, 24, and 25 peptide molecules.

In another illustrative embodiment described herein, an engineered collagen matrix is provided. The matrix comprises polymerized collagen, hyaluronic acid, and a hyaluronic acid-binding synthetic peptidoglycan. In another embodiment, a composition for in vitro culture of chondrocytes or stem cells is provided. The composition comprises any of the hyaluronic acid-binding synthetic peptidoglycans described in this disclosure.

In another embodiment described herein, a method of increasing pore size in an engineered collagen matrix is provided. The method comprises the steps of combining collagen, hyaluronic acid, and a hyaluronic acid-binding synthetic peptidoglycan and increasing the pore size in the matrix.

In yet another illustrative embodiment, a method of decreasing cartilage wear or erosion in a patient is provided. The method comprises the step of administering to the patient a hyaluronic acid-binding synthetic peptidoglycan, wherein the synthetic peptidoglycan decreases wear or erosion of the cartilage. In one embodiment, the cartilage erosion or wear may be caused by arthritis. In one embodiment, the cartilage erosion or wear may be caused by aging, obesity, trauma or injury, an anatomic abnormality, genetic diseases, metabolic imbalances, inflammation, or the like.

In yet another illustrative embodiment, a method of treatment for arthritis in a patient is provided. The method comprises the step of administering to the patient a hyaluronic acid-binding synthetic peptidoglycan, wherein the synthetic peptidoglycan reduces a symptom associated with the arthritis.

In another illustrative embodiment, a method of reducing or preventing hyaluronic acid degradation in a patient is provided. The method comprises administering to the patient a hyaluronic acid-binding synthetic peptidoglycan.

In another illustrative embodiment, a method of reducing or preventing collagen degradation is provided. The method comprises the steps of contacting a hyaluronic acid-binding synthetic peptidoglycan with hyaluronic acid in the presence of collagen, and reducing or preventing collagen degradation.

In yet another illustrative embodiment, a method for correcting or modifying a tissue defect in a patient is provided. The method comprises administering into the tissue defect a hyaluronic acid-binding synthetic peptidoglycan wherein the defect is corrected or modified. In another illustrative embodiment described herein, a dermal filler is provided. The filler comprises a hyaluronic acid-binding synthetic peptidoglycan. In one embodiment, the filler further comprises hyaluronic acid.

In yet another embodiment, an additive for a biomaterial cartilage or bone replacement composition is provided. The additive comprises a hyaluronic acid-binding synthetic peptidoglycan for addition to an existing biomaterial cartilage or bone replacement material. In another embodiment described herein, a method of preparing a biomaterial or bone cartilage replacement is provided. The method comprises the step of combining the synthetic peptidoglycan and an existing biomaterial or bone cartilage replacement material.

In the various embodiments, the peptide component of the synthetic peptidoglycan comprises an amino acid sequence of the formula B1-X1-X2-X3-X4-X5-X6-X7-X8-B2 (SEQ ID NO: 1),
    wherein X8 is present or is not present,
    wherein B1 is a basic amino acid,
    wherein B2 is a basic amino acid, and
    wherein X1-X8 are non-acidic amino acids.

In another embodiment, the peptide component of the synthetic peptidoglycan can comprise or can be an amino acid sequence of the formula B1-X1-B2-X2-X3-X4-X5-X6-X7-X8-X9-B3,
    wherein X9 is present or is not present,
    wherein B1 is a basic amino acid,
    wherein B2 is a basic amino acid,
    wherein B3 is a basic amino acid, and
    wherein X1-X9 are non-acidic amino acids.

In another embodiment, the synthetic peptide can comprise or can be an amino acid sequence of the formula B1-X1-X2-X3-X4-X5-X6-X7-X8-B2-X9-B3,
    wherein X8 is present or is not present,
    wherein B1 is a basic amino acid,
    wherein B2 is a basic amino acid,
    wherein B3 is a basic amino acid, and
    wherein X1-X9 are non-acidic amino acids.

As used herein, a "basic amino acid" is selected from the group consisting of lysine, arginine, or histidine. As used herein, a "non-acidic amino acid" is selected from the group consisting of alanine, arginine, asparagine, cysteine, glutamine, glycine, histidine, isoleucine, leucine, lysine, methionine, phenylalanine, proline, serine, threonine, tryptophan, tyrosine, and valine.

In the various illustrative embodiments described herein, the peptide component of the synthetic peptidoglycan can comprise an amino acid sequence selected from the group consisting of:

| | |
|---|---|
| GAHWQFNALTVRGG; | (SEQ ID NO: 2) |
| GDRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR. | (SEQ ID NO: 34) |

In each of the above peptide embodiments, the peptide may have a glycine-cysteine attached to the C-terminus of the peptide, and/or a glycine-cysteine-glycine (GCG) attached to the N-terminus of the peptide. In various embodiments described herein, the peptide component of the synthetic peptidoglycan comprises any amino acid sequence described in the preceding paragraph or an amino acid sequence with 80%, 85%, 90%, 95%, 98%, or 100% homology to any of these amino acid sequences.

Additional peptides that can be included as the peptide component of the hyaluronic acid-binding synthetic peptidoglycans include peptides described in Amemiya et al., Biochem. Biophys. Acta, vol. 1724, pp. 94-99 (2005), incorporated herein by reference. These peptides have an Arg-Arg motif and include peptides selected from the group consisting of:

| | |
|---|---|
| RRASRSRGQVGL; | (SEQ ID NO: 37) |
| GRGTHHAQKRRS; | (SEQ ID NO: 38) |
| QPVRRLGTPVVG; | (SEQ ID NO: 39) |
| ARRAEGKTRMLQ; | (SEQ ID NO: 40) |
| PKVRGRRHQASG; | (SEQ ID NO: 41) |
| SDRHRRRREADG; | (SEQ ID NO: 42) |
| NQRVRRVKHPPG; | (SEQ ID NO: 43) |
| RERRERHAVARHGPGLERDARNLARR; | (SEQ ID NO: 44) |
| TVRPGGKRGGQVGPPAGVLHGRRARS; | (SEQ ID NO: 45) |
| NVRSRRGHRMNS; | (SEQ ID NO: 46) |
| DRRRGRTRNIGN; | (SEQ ID NO: 47) |
| KTAGHGRRWSRN; | (SEQ ID NO: 48) |
| AKRGEGRREWPR; | (SEQ ID NO: 49) |
| GGDRRKAHKLQA; | (SEQ ID NO: 50) |
| RRGGRKWGSFEG; and | (SEQ ID NO: 51) |
| RQRRRDLTRVEG. | (SEQ ID NO: 17) |

In each of the above peptide embodiments, the peptide may have a glycine-cysteine attached to the C-terminus of the peptide. In each of the above peptide embodiments, the peptide may have a glycine-cysteine-glycine (GCG) attached to the N-terminus of the peptide. In various embodiments described herein, the peptide component of the synthetic peptidoglycan comprises any amino acid sequence described in the preceding paragraph or an amino acid sequence with 80%, 85%, 90%, 95%, 98%, or 100% homology to any of these amino acid sequences.

In other embodiments, peptides described in Yang et al., EMBO Journal, vol. 13, pp. 286-296 (1994), incorporated herein by reference, and Goetinck et al., J. Cell. Biol., vol. 105, pp. 2403-2408 (1987), incorporated herein by reference, can be used in the hyaluronic acid-binding synthetic peptidoglycans described herein including peptides selected from the group consisting of RDGTRYVQKGEYR (SEQ ID NO: 52), HREARSGKYK (SEQ ID NO: 53), PDKKHKLYGV (SEQ ID NO: 54), and WDKERSRYDV (SEQ ID NO: 55). In each of these embodiments, the peptide may have a glycine-cysteine attached to the C-terminus of the peptide. In each of these embodiments, the peptide may have a glycine-cysteine-glycine (GCG) attached to the N-terminus of the peptide. In other embodiments, the peptide component of the synthetic peptidoglycan comprises an amino acid sequence with 80%, 85%, 90%, 95%, 98%, or 100% homology to any of these amino acid sequences.

In various embodiments, the peptide component of the synthetic peptidoglycan described herein can be modified by the inclusion of one or more conservative amino acid substitutions. As is well-known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions are possible provided that these do not excessively affect the hyaluronic acid binding activity of the peptide.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in TABLE 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S—Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S—Me-Cys, Ile, D-Ile, Leu, D-Leu,Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In one embodiment, the conservative amino acid substitutions applicable to the molecules described herein do not alter the motifs that consist of the B1-X1-X2-X3-X4-X5-X6-X7-X8-B2 formula, the B1-X1-B2-X2-X3-X4-X5-X6-X7-X8-X9-B3 formula, the B1-X1-X2-X3-X4-X5-X6-X7-X8-B2-X9-B3 formula, or the Arg-Arg motif.

In various embodiments described herein, the glycan (e.g. glycosaminoglycan, abbreviated GAG, or polysaccharide) component of the synthetic peptidoglycan described herein can be selected from the group consisting of dextran, chondroitin, chondroitin sulfate, dermatan, dermatan sulfate, heparan, heparin, keratin, keratan sulfate, and hyaluronic acid. In one embodiment, the glycan is selected from the group consisting of chondroitin sulfate and keratan sulfate. In another illustrative embodiment, the glycan is chondroitin sulfate.

In one embodiment described herein, the hyaluronic acid-binding synthetic peptidoglycan comprises (GAHWQFNALTVRGG (SEQ ID NO: 2))$_{10}$ conjugated to chondroitin sulfate wherein each peptide in the peptidoglycan molecule is linked separately to chondroitin sulfate. In another embodiment described herein, the hyaluronic acid-binding synthetic peptidoglycan comprises (GAHWQFNALTVRGGGC (SEQ ID NO: 35))$_{11}$ conjugated to chondroitin sulfate wherein each peptide in the peptidoglycan molecule is linked separately to chondroitin sulfate. In each of the above peptide embodiments, the peptide number may be selected from the group consisting of 1, 2, 3, 4, 5, 6, 7, 8, 9, 10, 11, 12, 13, 14, 15, 16, 17, 18, 19, 20, 21, 22, 23, 24, and 25 peptide molecules.

In various embodiments described herein, the synthetic peptidoglycan is resistant to aggrecanase. An aggrecanase is characterized in the art as any enzyme known to cleave aggrecan.

In one illustrative aspect, the hyaluronic acid-binding synthetic peptidoglycan may be sterilized. As used herein "sterilization" or "sterilize" or "sterilized" means disinfecting the hyaluronic acid-binding synthetic peptidoglycans by removing unwanted contaminants including, but not limited to, endotoxins and infectious agents.

In various illustrative embodiments, the hyaluronic acid-binding synthetic peptidoglycan can be disinfected and/or sterilized using conventional sterilization techniques including propylene oxide or ethylene oxide treatment, gas plasma sterilization, gamma radiation (e.g., 1-4 Mrads gamma irradiation or 1-2.5 Mrads of gamma irradiation), electron beam, and/or sterilization with a peracid, such as peracetic acid. Sterilization techniques which do not adversely affect the structure and biotropic properties of the hyaluronic acid-binding synthetic peptidoglycan can be used. In one embodiment, the hyaluronic acid-binding synthetic peptidoglycan can be subjected to one or more sterilization processes. In another illustrative embodiment, the hyaluronic acid-binding synthetic peptidoglycan is subjected to sterile filtration. The hyaluronic acid-binding synthetic peptidoglycan may be wrapped in any type of container including a plastic wrap or a foil wrap, and may be further sterilized. The hyaluronic acid-binding synthetic peptidoglycan may be prepared under sterile conditions, for example, by lyophilisation, which may readily be accomplished using standard techniques well-known to those skilled in the art.

In various embodiments described herein, the hyaluronic acid-binding synthetic peptidoglycans can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

In various embodiments described herein, the peptide component of the synthetic peptidoglycan is synthesized according to solid phase peptide synthesis protocols that are well-known by persons of skill in the art. In one embodiment a peptide precursor is synthesized on a solid support according to the well-known Fmoc protocol, cleaved from the support with trifluoroacetic acid and purified by chromatography according to methods known to persons skilled in the art.

In various embodiments described herein, the peptide component of the synthetic peptidoglycan is synthesized utilizing the methods of biotechnology that are well-known to persons skilled in the art. In one embodiment a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium according to methods known by persons skilled in the art (e.g., by affinity purification). Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

In various embodiments described herein, the peptide component of the hyaluronic acid-binding synthetic peptidoglycan is conjugated to a glycan by reacting a free amino group of the peptide with an aldehyde function of the glycan in the presence of a reducing agent, utilizing methods known to persons skilled in the art, to yield the peptide glycan conjugate. In one embodiment an aldehyde function of the glycan (e.g. polysaccharide or glycosaminoglycan) is formed by reacting the glycan with sodium metaperiodate according to methods known to persons skilled in the art.

In one embodiment, the peptide component of the synthetic peptidoglycan is conjugated to a glycan by reacting an aldehyde function of the glycan with 3-(2-pyridyldithio)propionyl hydrazide (PDPH) to form an intermediate glycan and further reacting the intermediate glycan with a peptide containing a free thiol group to yield the peptide glycan conjugate. In yet another embodiment, the sequence of the peptide component of the synthetic peptidoglycan may be modified to include a glycine-cysteine segment to provide an attachment point for a glycan or a glycan-linker conjugate. In any of the embodiments described herein, the crosslinker can be N-[β-Maleimidopropionic acid]hydrazide (BMPH).

Although specific embodiments have been described in the preceding paragraphs, the hyaluronic acid-binding synthetic peptidoglycans described herein can be made by using any art-recognized method for conjugation of the peptide to the glycan (e.g. polysaccharide or glycosaminoglycan). This can include covalent, ionic, or hydrogen bonding, either directly or indirectly via a linking group such as a divalent linker. The conjugate is typically formed by covalent bonding of the peptide to the glycan through the formation of amide, ester or imino bonds between acid, aldehyde, hydroxy, amino, or hydrazo groups on the respective components of the conjugate. All of these methods are known in the art or are further described in the Examples section of this application or in Hermanson G. T., Bioconjugate Techniques, Academic Press, pp. 169-186 (1996), incorporated herein by reference. The linker typically comprises about 1 to about 30 carbon atoms, more typically about 2 to about 20 carbon atoms. Lower molecular weight linkers (i.e., those having an approximate molecular weight of about 20 to about 500) are typically employed.

In addition, structural modifications of the linker portion of the conjugates are contemplated herein. For example, amino acids may be included in the linker and a number of amino acid substitutions may be made to the linker portion of the conjugate, including but not limited to naturally occurring amino acids, as well as those available from conventional synthetic methods. In another aspect, beta, gamma, and longer chain amino acids may be used in place of one or more alpha amino acids. In another aspect, the linker may be shortened or lengthened, either by changing the number of amino acids included therein, or by including more or fewer beta, gamma, or longer chain amino acids. Similarly, the length and shape of other chemical fragments of the linkers described herein may be modified.

In various embodiments described herein, the linker may include one or more bivalent fragments selected independently in each instance from the group consisting of alkylene, heteroalkylene, cycloalkylene, cycloheteroalkylene, arylene, and heteroarylene each of which is optionally substituted. As used herein heteroalkylene represents a group resulting from the replacement of one or more carbon atoms in a linear or branched alkylene group with an atom independently selected in each instance from the group consisting of oxygen, nitrogen, phosphorus and sulfur. In an alternative embodiment, a linker is not present.

In one embodiment described herein, an engineered collagen matrix is provided. The previously described embodiments of the hyaluronic acid-binding synthetic peptidoglycan are applicable to the engineered collagen matrix described herein. In one embodiment, the engineered collagen matrix comprises polymerized collagen, hyaluronic acid, and a hyaluronic acid-binding synthetic peptidoglycan. In one embodiment, the engineered collagen matrix comprises polymerized collagen and a hyaluronic-binding synthetic peptidoglycan. In various illustrative embodiments, crosslinking agents, such as carbodiimides, aldehydes, lysl-oxidase, N-hydroxysuccinimide esters, imidoesters, hydrazides, and maleimides, as well as various natural crosslinking agents, including genipin, and the like, can be added before, during, or after polymerization of the collagen in solution.

In various illustrative embodiments, the collagen used herein to prepare an engineered collagen matrix may be any type of collagen, including collagen types I to XXVIII, alone or in any combination, for example, collagen types I, II, III, and/or IV may be used. In some embodiments, the collagen used to prepare an engineered collagen matrix is selected from the group consisting of type I collagen, type II collagen, type III collagen, type IV collagen, type IX collagen, type XI collagen, and combinations thereof. In one embodiment, the engineered collagen matrix is formed using commercially available collagen (e.g., Sigma, St. Louis, Mo.). In an alternative embodiment, the collagen can be purified from submucosa-containing tissue material such as intestinal, urinary bladder, or stomach tissue. In a further embodiment, the collagen can be purified from tail tendon. In an additional embodiment, the collagen can be purified from skin. In various aspects, the collagen can also contain endogenous or exogenously added non-collagenous proteins in addition to the collagen-binding synthetic peptidoglycans, such as fibronectin or silk proteins, glycoproteins, and polysaccharides, or the like. The engineered collagen matrices prepared by the methods described herein can be in the form of a tissue graft (e.g., in the form of a gel) which can assume the characterizing features of the tissue(s) with which they are associated at the site of implantation or injection. In one embodiment, the engineered collagen matrix is a tissue graft that can be implanted into a patient. In another embodiment, the engineered collagen matrix can be administered to a patient by injection. In either embodiment, the matrix can be in the form of a gel or a powder, for example.

In one embodiment, the collagen in the engineered collagen matrix comprises about 40 to about 90 dry weight (wt) % of the matrix, about 40 to about 80 dry wt % of the matrix, about 40 to about 70 dry wt % of the matrix, about 40 to about 60 dry wt % of the matrix, about 50 to about 90 dry wt % of the matrix, about 50 to about 80 dry wt % of the matrix, about 50 to about 75 dry wt % of the matrix, about 50 to about 70 dry wt % of the matrix, or about 60 to about 75 dry wt % of the matrix. In another embodiment, the collagen in the engineered collagen matrix comprises about 90 dry wt %, about 85 dry wt %, about 80 dry wt %, about 75 dry wt %, about 70 dry wt %, about 65 dry wt %, about 60 dry wt %, about 50 dry wt %, about 45 dry wt %, about 40 dry wt %, or about 30 dry wt % of the matrix.

In one embodiment, the final collagen concentration of the matrix in gel form is about 0.5 to about 6 mg per mL, about 0.5 to about 5 mg per mL, about 0.5 to about 4 mg per mL, about 1 to about 6 mg per mL, about 1 to about 5 mg per mL, or about 1 to about 4 mg per mL. In one embodiment, the final collagen concentration of the matrix is about 0.5 mg per mL, about 1 mg per mL, about 2 mg per mL, about 3 mg per mL, about 4 mg per mL, or about 5 mg per mL.

In one embodiment, the hyaluronic acid-binding synthetic peptidoglycan in the engineered collagen matrix comprises about 2 to about 60 dry weight (wt) % of the matrix, about 2 to about 50 dry wt % of the matrix, about 5 to about 50 dry wt % of the matrix, about 10 to about 50 dry wt % of the matrix, about 10 to about 20 dry wt % of the matrix, about 10 to about 30 dry wt % of the matrix, about 10 to about 25 dry wt % of the matrix, about 15 to about 30 dry wt % of the matrix, or about 15 to about 45 dry wt % of the matrix. In another embodiment, the hyaluronic acid-binding synthetic peptidoglycan in the engineered collagen matrix comprises about 2 dry wt %, about 5 dry wt %, about 10 dry wt %, about 15 dry wt %, about 20 dry wt %, about 25 dry wt %, about 30 dry wt %, about 35 dry wt %, about 40 dry wt %, about 45 dry wt %, or about 50 dry wt % of the matrix In another embodiment, the engineered collagen matrix comprises hyaluronic acid and the hyaluronic acid in the engineered collagen matrix comprises about 2 to about 60 dry weight (wt) % of the matrix, about 2 to about 50 dry wt % of the matrix, about 5 to about 50 dry wt % of the matrix, about 10 to about 50 dry wt % of the matrix, about 10 to about 20 dry wt % of the matrix, about 10 to about 30 dry wt % of the matrix, about 10 to about 25 dry wt % of the matrix, about 15 to about 30 dry wt % of the matrix, or about 15 to about 45 dry wt % of the matrix. In another embodiment, the hyaluronic acid in the engineered collagen matrix comprises about 2 dry wt %, about 5 dry wt %, about 10 dry wt %, about 15 dry wt %, about 20 dry wt %, about 25 dry wt %, about 30 dry wt %, about 35 dry wt %, about 40 dry wt %, about 45 dry wt %, or about 50 dry wt % of the matrix.

In one embodiment, the engineered collagen matrix comprises hyaluronic acid and a hyaluronic acid-binding synthetic peptidoglycan. The hyaluronic acid and hyaluronic acid-binding synthetic peptidoglycan in the engineered collagen matrix comprise about 10 to about 60 dry weight (wt) % of the matrix, about 20 to about 60 dry wt % of the matrix, about 30 to about 60 dry wt % of the matrix, about 40 to about 60 dry wt % of the matrix, about 10 to about 50 dry wt % of the matrix, about 20 to about 50 dry wt % of the matrix, about 25 to about 50 dry wt % of the matrix, about 30 to about 50 dry wt % of the matrix, or about 25 to about 40 dry wt % of the matrix. In another embodiment, the hyaluronic acid and hyaluronic acid-binding synthetic peptidoglycan in the engineered collagen matrix comprises about 10 dry wt %, about 15 dry wt %, about 20 dry wt %, about 25 dry wt %, about 30 dry wt %, about 35 dry wt %, about 40 dry wt %, about 50 dry wt %, about 55 dry wt %, about 60 dry wt %, or about 70 dry wt % of the matrix.

In one illustrative aspect, the engineered collagen matrix may be sterilized. As used herein "sterilization" or "sterilize" or "sterilized" means disinfecting the matrix by removing unwanted contaminants including, but not limited to, endotoxins, nucleic acid contaminants, and infectious agents.

In various illustrative embodiments, the engineered collagen matrix can be disinfected and/or sterilized using conventional sterilization techniques including glutaraldehyde tanning, formaldehyde tanning at acidic pH, propylene oxide or ethylene oxide treatment, gas plasma sterilization, gamma radiation (e.g., 1-4 Mrads gamma irradiation or 1-2.5 Mrads of gamma irradiation), electron beam, and/or sterilization with a peracid, such as peracetic acid. Sterilization techniques which do not adversely affect the structure and biotropic properties of the matrix can be used. In one embodiment, the engineered collagen matrix can be subjected to one or more sterilization processes. In illustrative embodiments, the collagen in solution, prior to polymerization, can also be sterilized or disinfected. The engineered collagen matrix may be wrapped in any type of container including a plastic wrap or a foil wrap, and may be further sterilized.

In any of these embodiments the engineered collagen matrix may further comprise an exogenous population of cells. The added population of cells may comprise one or more cell populations. In various embodiments, the cell populations comprise a population of non-keratinized or keratinized epithelial cells or a population of cells selected from the group consisting of endothelial cells, mesodermally derived cells, mesothelial cells, synoviocytes, neural cells, glial cells, osteoblasts, fibroblasts, chondrocytes, tenocytes, smooth muscle cells, skeletal muscle cells, cardiac muscle cells, multi-potential progenitor cells (e.g., stem cells, including bone marrow progenitor cells), and osteogenic cells. In some embodiments, the population of cells is selected from the group consisting of chondrocytes and stem cells. In some embodiments, the stem cells are selected from the group consisting of osteoblasts, osteogenic cells, and mesenchymal stem cells. In various embodiments, the engineered collagen matrix can be seeded with one or more cell types in combination.

In various aspects, the engineered collagen matrices or engineered graft constructs of the present invention can be combined with nutrients, including minerals, amino acids, sugars, peptides, proteins, vitamins (such as ascorbic acid), or laminin, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic. In other illustrative embodiments, cross-linking agents, such as carbodiimides, aldehydes, lysl-oxidase, N-hydroxysuccinimide esters, imidoesters, hydrazides, and maleimides, as well as natural crosslinking agents, including genipin, and the like can be added before, concurrent with, or after the addition of cells.

As discussed above, in accordance with one embodiment, cells can be added to the engineered collagen matrices or the engineered graft constructs after polymerization of the collagen or during collagen polymerization. The engineered collagen matrices comprising the cells can be subsequently injected or implanted in a host for use as engineered graft constructs. In another embodiment, the cells on or within the engineered collagen matrices can be cultured in vitro, for a predetermined length of time, to increase the cell number or to induce desired remodeling prior to implantation or injection into a patient.

In one embodiment described herein, a composition for in vitro culture of chondrocytes or stem cells is provided (i.e., for in vitro culture of cells without subsequent implantation or injection into a patient). The composition for in vitro culture comprises a hyaluronic acid-binding synthetic peptidoglycan. The previously described embodiments of the hyaluronic acid-binding synthetic peptidoglycan are applicable to the composition for in vitro culture described herein.

In various aspects, the composition for in vitro culture of the present invention can be combined with nutrients, including minerals, amino acids, sugars, peptides, proteins, vitamins (such as ascorbic acid), or laminin, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone.

In some embodiments, the composition for in vitro culture includes stem cells selected from the group consisting of osteoblasts, osteogenic cells, and mesenchymal stem cells. In various embodiments, the composition for in vitro culture can be seeded with one or more cell types in combination.

In one illustrative aspect, the composition for in vitro culture may be sterilized. As used herein "sterilization" or "sterilize" or "sterilized" means disinfecting the composition by removing unwanted contaminants including, but not limited to, endotoxins, nucleic acid contaminants, and infectious agents. The sterilization procedures, methods and embodiments provided in the preceding paragraphs are also applicable to the composition for in vitro culture described herein. The in vitro culture composition may be used to expand populations of cells for implantation or injection into a patient.

In one embodiment described herein, an additive for a biomaterial cartilage replacement composition is provided. The additive comprises a hyaluronic acid-binding synthetic peptidoglycan for addition to an existing biomaterial cartilage replacement material. The previously described embodiments of the hyaluronic acid-binding synthetic peptidoglycan are applicable to the additive described herein.

As used herein, the phrase "existing biomaterial cartilage replacement material" means a biologically compatible composition that can be utilized for replacement of damaged, defective, or missing cartilage in the body. Various types of existing biomaterial cartilage replacement compositions are well-known in the art and are contemplated. For example, existing biomaterial cartilage or bone replacement compositions include the DeNovo® NT Natural Tissue Graft (Zimmer), MaioRegen™ (JRI Limited), or the collection of cryopreserved osteoarticular tissues produced by Biomet.

In one embodiment, a method of preparing a biomaterial or bone cartilage replacement is provided. The method comprises the step of combining the synthetic peptidoglycan and an existing biomaterial or bone cartilage replacement material. The previously described embodiments of the hyaluronic acid-binding synthetic peptidoglycan are applicable to the method described herein.

In one embodiment, a method of treatment for arthritis in a patient is provided. The method comprises the step of administering to the patient a hyaluronic acid-binding synthetic peptidoglycan, wherein the synthetic peptidoglycan reduces one or more symptoms associated with arthritis. The previously described embodiments of the hyaluronic acid-binding synthetic peptidoglycan are applicable to the method described herein.

In various embodiments, the synthetic peptidoglycan used in the method of treatment for arthritis reduces one or more symptoms associated with arthritis. Various symptoms are known in the art to be associated with arthritis, including but not limited to pain, stiffness, tenderness, inflammation, swelling, redness, warmth, and decreased mobility. The symptoms of arthritis may be present in a joint, a tendon, or other parts of the body. As used herein, "reducing" means preventing or completely or partially alleviating a symptom of arthritis.

In various embodiments, the arthritis is osteoarthritis or rheumatoid arthritis. The pathogenesis and clinical symptoms of osteoarthritis and rheumatoid arthritis are well-known in the art. In one embodiment of this method, the synthetic peptidoglycan acts as a lubricant following administration or prevents loss of cartilage. In another embodiment, the synthetic peptidoglycan prevents articulation of bones in the patient. For example, the synthetic peptidoglycan inhibits bone on bone articulation in a patient with reduced or damaged cartilage.

In one embodiment, a method of reducing or preventing degradation of ECM components in a patient is provided. For example, a method of reducing or preventing degradation of ECM components in the cartilage of a patient is provided. The method comprises administering to the patient a hyaluronic acid-binding synthetic peptidoglycan. The previously described embodiments of the hyaluronic acid-binding synthetic peptidoglycan are applicable to the method described herein. In one embodiment, the synthetic peptidoglycan is resistant to matrix metallo proteases, e.g., an aggrecanase.

In another embodiment, a method of reducing or preventing hyaluronic acid degradation in a patient is provided. The method comprises administering to the patient a hyaluronic acid-binding synthetic peptidoglycan. The previously described embodiments of the hyaluronic acid-binding synthetic peptidoglycan are applicable to the method described herein.

In another embodiment, a method of reducing or preventing collagen degradation is provided. The method comprises the steps of contacting a hyaluronic acid-binding synthetic peptidoglycan with hyaluronic acid in the presence of collagen, and reducing or preventing collagen degradation. The previously described embodiments of the hyaluronic acid-binding synthetic peptidoglycan are applicable to the method described herein.

In another embodiment, a method of reducing or preventing chondroitin sulfate degradation is provided. The method comprises the steps of contacting a hyaluronic acid-binding synthetic peptidoglycan with hyaluronic acid in the presence of collagen, and reducing or preventing chondroitin sulfate degradation. The previously described embodiments of the hyaluronic acid-binding synthetic peptidoglycan are applicable to the method described herein.

"Reducing" ECM component degradation, e.g., hyaluronic acid, collagen, or chondroitin sulfate degradation, means completely or partially reducing degradation of hyaluronic acid, collagen, or chondroitin sulfate, respectively.

In one embodiment, reducing hyaluronic acid degradation in a patient means reducing the rate of hyaluronic acid degradation. For example, FIG. 8 described in the Examples section of the application shows that the rate of hyaluronic acid degradation in a mixture of hyaluronic acid and a hyaluronic acid-binding synthetic peptidoglycan is significantly reduced upon addition of the synthetic peptidoglycan.

In one embodiment, reducing collagen degradation means reducing the rate of collagen degradation. For example, FIG. 10 described in the Examples section of the application shows that the rate of collagen degradation in the presence of hyaluronic acid and a hyaluronic acid-binding synthetic peptidoglycan is significantly reduced upon addition of the synthetic peptidoglycan.

Figure 11:
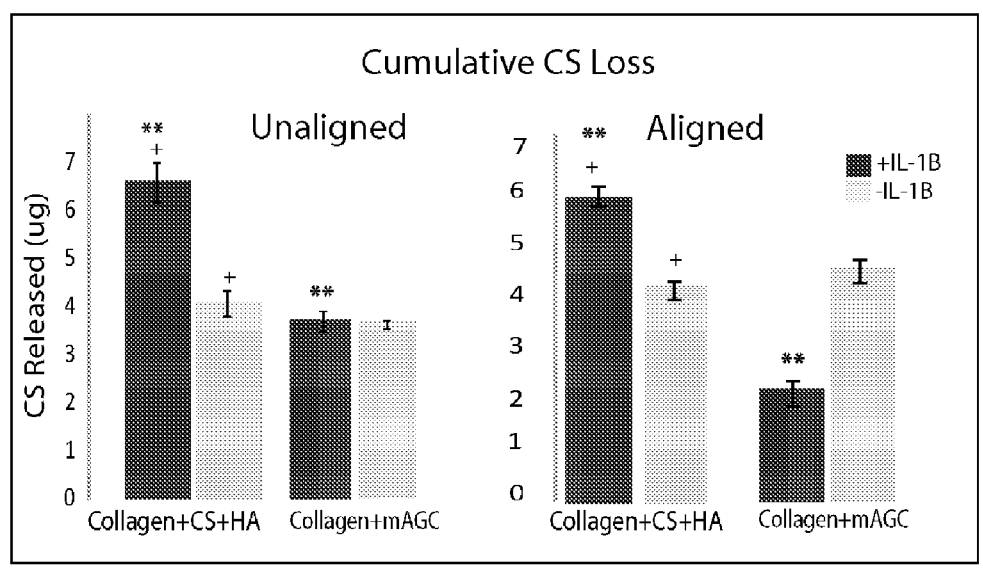
FIG. 11 shows the cumulative chondroitin sulfate (CS) loss over an eight-day culture period in media stimulated with and without IL-1β. CS loss was measured by a DMMB assay. The addition of mAGC had a significant effect on loss of CS from the scaffolds (p<0.001). ** denotes statistical significance between scaffold prepared without aggrecan mimic and those prepared with mAGC. + denotes statistical significance between scaffold treated with and without IL-1β (p<0.05). Bars represent average ±SEM (n=3).
Figure 12:
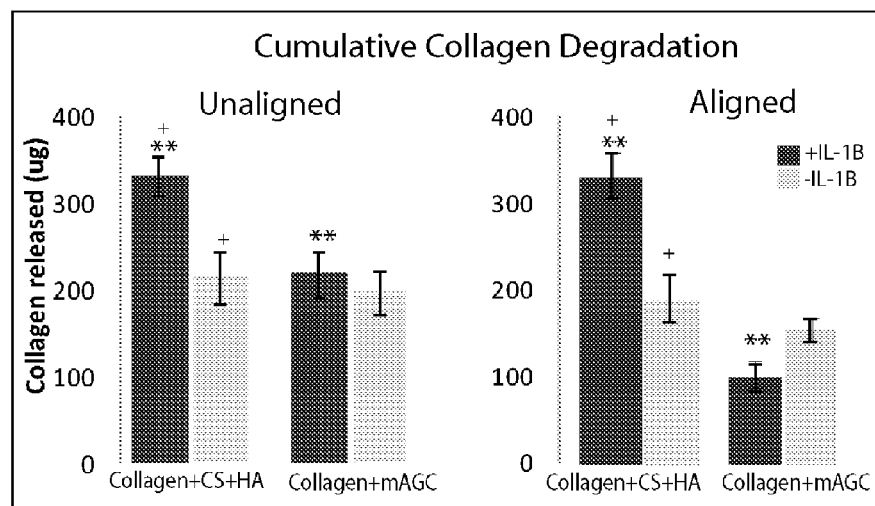
FIG. 12 shows the cumulative collagen breakdown over an eight-day culture period in media stimulated with and without IL-1β. Collagen breakdown was measured by a Sircol assay. The addition of aggrecan mimic had a significant effect on loss of collagen from the scaffolds (p<0.02). ** denotes statistical significance between scaffold prepared without aggrecan mimic and those prepared with mAGC. + denotes statistical significance between scaffold treated with and without IL-1β (p<0.05). Bars represent average ±SEM (n=3).

In one embodiment, reducing chondroitin sulfate degradation means reducing the rate of chondroitin sulfate degradation. For example, FIG. 11 described in the Examples section of the application shows that the rate of chondroitin sulfate degradation in the presence of a hyaluronic acid-binding synthetic peptidoglycan is significantly reduced upon addition of the synthetic peptidoglycan.

In one embodiment described herein, a method for correcting or modifying a tissue defect in a patient is provided. The method comprises administering into the tissue defect hyaluronic acid and a hyaluronic acid-binding synthetic peptidoglycan wherein the defect is corrected or modified. The previously described embodiments of the hyaluronic acid-binding synthetic peptidoglycan are applicable to the method described herein. In one embodiment, the tissue defect is a cosmetic defect.

The following embodiments are applicable to methods described herein where the hyaluronic acid-binding synthetic peptidoglycan is administered to a patient. In various embodiments, the hyaluronic acid-binding synthetic peptidoglycan can be injected or implanted (e.g., incorporated in a cartilage repair composition or device). In some embodiments described herein, the injection is an intraarticular injection. In another embodiment described herein, the injection is into a joint capsule of the patient. In other embodiments, the injection is a subcutaneous injection, as in the case of dermal fillers. Suitable means for injection include a needle (including microneedle) injector or a device for infusion.

In an illustrative embodiment, pharmaceutical formulations for use with hyaluronic acid-binding synthetic peptidoglycans for administration to a patient comprise: a) a pharmaceutically active amount of the hyaluronic acid-binding synthetic peptidoglycan; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any individual component a), b), c), or d) or any combinations of a), b), c) and d).

In various embodiments described herein, the pH buffering agents are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In various embodiments described herein, the ionic strength modifying agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and non-ionic water soluble polymers; crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or basic agent are employed in order to facilitate achieving the desired pH of the formulation.

In various embodiments described herein, formulations for injection may be suitably formulated as a sterile non-aqueous solution or as a dried form (e.g., lyophilized) to be used in conjunction with a suitable vehicle such as sterile, pyrogen-free water. The preparation of formulations for injection under sterile conditions, for example, by lyophilisation, may readily be accomplished using standard pharmaceutical techniques well-known to those skilled in the art. In one embodiment, the viscosity of a solution containing hyaluronic acid is increased by addition of a hyaluronic acid-binding synthetic peptidoglycan.

In various embodiments described herein, the solubility of a hyaluronic acid-binding synthetic peptidoglycan used in the preparation of formulations for administration via injection may be increased by the use of appropriate formulation techniques, such as the incorporation of solubility-enhancing compositions such as mannitol, ethanol, glycerin, polyethylene glycols, propylene glycol, poloxomers, and others known to those of skill in the art.

In various embodiments described herein, formulations for administration via injection may be formulated to be for immediate and/or modified release. Modified release formulations include delayed, sustained, pulsed, controlled, targeted and programmed release formulations. Thus, a hyaluronic acid-binding synthetic peptidoglycan may be formulated as a solid, semi-solid, or thixotropic liquid for administration as an implanted depot providing modified release of the active compound. Illustrative examples of such formulations include drug-coated stents and copolymeric(dl-lactic, glycolic)acid (PGLA) microspheres. In another embodiment, hyaluronic acid-binding synthetic peptidoglycans or compositions comprising hyaluronic acid-binding synthetic peptidoglycan may be continuously administered, where appropriate.

In any of the embodiments described herein, the hyaluronic acid-binding synthetic peptidoglycan can be administered alone or in combination with suitable pharmaceutical carriers or diluents. Diluent or carrier ingredients used in the hyaluronic acid-binding synthetic peptidoglycan formulation can be selected so that they do not diminish the desired effects of the hyaluronic acid-binding synthetic peptidoglycan. The hyaluronic acid-binding synthetic peptidoglycan formulation may be in any suitable form. Examples of suitable dosage forms include aqueous solutions of the hyaluronic acid-binding synthetic peptidoglycan, for example, a solution in isotonic saline, 5% glucose or other well-known pharmaceutically acceptable liquid carriers such as alcohols, glycols, esters and amides.

Suitable dosages of the hyaluronic acid-binding synthetic peptidoglycan can be determined by standard methods, for example by establishing dose-response curves in laboratory animal models or in clinical trials. In various embodiments described herein, the dosage of the hyaluronic acid-binding synthetic peptidoglycan, can vary significantly depending on the patient condition, the disease state being treated, the route of administration and tissue distribution, and the possibility of co-usage of other therapeutic treatments. Illustratively, suitable dosages of hyaluronic acid-binding synthetic peptidoglycan (administered in a single bolus or over time) include from about 1 ng/kg to about 10 mg/kg, from about 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses can range from about 0.01 µg to about 1000 mg per dose, from about 1 µg to about 100 mg per dose, or from about 100 µg to about 50 mg per dose, or from about 500 µg to about 10 mg per dose, or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In one embodiment, suitable dosages of a hyaluronic acid-binding synthetic peptidoglycan include concentrations ranging from about 0.01 uM to about 100 uM, about 0.05 to about 100 uM, about 0.1 uM to about 100 uM, about 0.1 uM to about 50 uM, about 0.1 uM to about 20 uM, about 0.1 uM to about 10 uM, about 0.5 uM to about 10 uM, about 0.5 uM to about 50 uM, and about 0.5 uM to about 100 uM. In another embodiment, suitable dosages of a hyaluronic acid-binding synthetic peptidoglycan include concentrations of about 0.01 uM, 0.1 uM, 0.2 uM, 0.5 uM, 1 uM, 2 uM, 5 uM, 10 uM, 20 uM, 50 uM, and 100 uM.

The hyaluronic acid-binding synthetic peptidoglycan can be formulated in an excipient. In any of the embodiments described herein, the excipient can have a concentration ranging from about 0.4 mg/ml to about 6 mg/ml. In various embodiments, the concentration of the excipient may range from about 0.5 mg/ml to about 10 mg/ml, from about 0.1 mg/ml to about 6 mg/ml, from about 0.5 mg/ml to about 3 mg/ml, from about 1 mg/ml to about 3 mg/ml, from about 0.01 mg/ml to about 10 mg/ml, and from about 2 mg/ml to about 4 mg/ml.

In embodiments where the hyaluronic acid-binding synthetic peptidoglycan is implanted as part of a cartilage repair composition or device (e.g., a gel for implantation), any suitable formulation described above may be used.

Any effective regimen for administering the hyaluronic acid-binding synthetic peptidoglycan can be used. For example, the hyaluronic acid-binding synthetic peptidoglycan can be administered as a single dose, or as a multiple-dose daily regimen. Further, a staggered regimen, for example, one to five days per week can be used as an alternative to daily treatment.

In various embodiments described herein, the patient is treated with multiple injections of the hyaluronic acid-binding synthetic peptidoglycan. In one embodiment, the patient is injected multiple times (e.g., about 2 up to about 50 times) with the hyaluronic acid-binding synthetic peptidoglycan, for example, at 12-72 hour intervals or at 48-72 hour intervals. Additional injections of the hyaluronic acid-binding synthetic peptidoglycan can be administered to the patient at an interval of days or months after the initial injections(s).

In any of the embodiments herein described, it is to be understood that a combination of two or more hyaluronic acid-binding synthetic peptidoglycans, differing in the peptide portion, the glycan portion, or both, can be used in place of a single hyaluronic acid-binding synthetic peptidoglycan.

It is also appreciated that in the foregoing embodiments, certain aspects of the compounds, compositions and methods are presented in the alternative in lists, such as, illustratively, selections for any one or more of G and P. It is therefore to be understood that various alternate embodiments of the invention include individual members of those lists, as well as the various subsets of those lists. Each of those combinations is to be understood to be described herein by way of the lists.

In the following illustrative examples, the terms "aggrecan mimetic" and "mimetic" are used synonymously with the term "hyaluronic acid-binding synthetic peptidoglycan."

EXAMPLE 1

Peptide Synthesis

All peptides were synthesized using a Symphony peptide synthesizer (Protein Technologies, Tucson, Ariz.), utilizing an FMOC protocol on a Knorr resin. The crude peptide was released from the resin with TFA and purified by reverse phase chromatography on an AKTAexplorer (GE Healthcare, Piscataway, N.J.) utilizing a Grace-Vydac 218TP C-18 reverse phase column and a gradient of water/acetonitrile 0.1% TFA. Dansyl-modified peptides were prepared by adding an additional coupling step with dansyl-Gly (Sigma) before release from the resin. Peptide structures were confirmed by mass spectrometry. The following peptides were prepared as described above: GAHWQFNALTVRGGGC (SEQ ID NO: 35), KQKIKHVVKLKGC (SEQ ID NO: 56), and KLKSQLVKRKGC (SEQ ID NO: 57).

EXAMPLE 2

Chondroitin Sulfate Functionalization and Synthetic Peptidoglycan Formation

The reaction schematic for the creation of the aggrecan mimic (i.e., GAH) can be seen in FIG. 1. Functionalization of the chondroitin sulfate (CS) (Sigma, St. Louis, Mo.) was accomplished using sodium periodate (Thermo Scientific, Waltham, Mass.) to oxidize the CS. By varying the reaction duration and sodium periodate concentration, the number of aldehyde groups produced by the oxidation reaction was controlled, values presented in Table 2. Table 2 details the sodium periodate concentration and the reaction duration needed to obtain the desired number of aldehydes per CS chain. Through progressive chemical reactions, schematic shown in FIG. 1, the number of BMPH attached per CS chain is assumed to equal the number of aldehydes produced and the number of hyaluronic acid (HA) binding peptides attached.

Based on the reaction duration and the concentration of sodium periodate, the number of peptides (average) per CS chain is shown in Table 2.

TABLE 2

| Sodium Periodate Concentration (mM) | Reaction Duration (hr) | # Aldehydes/ CS Chain |
| --- | --- | --- |
| 10 | 24 | 3 |
| 20 | 24 | 7.2 |
| 30 | 24 | 8.5 |
| 20 | 48 | 9 |
| 30 | 48 | 10.5 |

The concentration of CS was kept constant at 20 mg per mL for all oxidation reactions. The measured amounts of CS and sodium periodate were reacted and protected from light in 0.1 M sodium acetate buffer (pH 5.5) for the durations specified. Completion of the reaction was obtained by removing sodium periodate by performing gel filtration chromatography with a Bio-Scale Mini Bio-Gel column packed with polyacrylamide beads (Bio-Rad Laboratories, Hercules, Calif.) using an ÄKTA Purifier FPLC (GE Healthcare, Piscataway, N.J.). The running buffer used for the desalting process was 1× Phosphate Buffered Saline (PBS, pH 7.4, Invitrogen, Carlsbad, Calif.).

Figure 2:
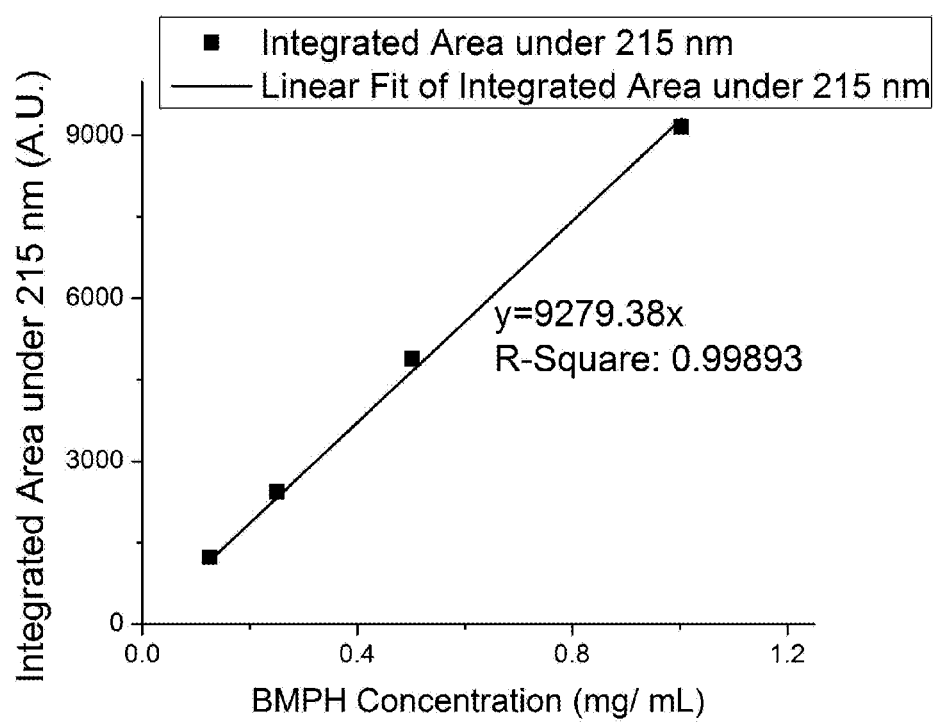
FIG. 2 shows a standard curve of N-[β-Maleimidopropionic acid]hydrazide, trifluoroacetic acid salt (hereinafter "BMPH") absorbance (215 nm) based on amount (mg) of BMPH injected. The standard curve was used to determine the amount of BMPH consumed during the coupling reaction.

N-[β-Maleimidopropionic acid]hydrazide, trifluoroacetic acid salt (BMPH, Pierce, Rockford, Ill.) was reacted in a 50 M excess with the desalted, oxidized CS in 1×PBS. The hydrazide end of BMPH reacts to covalently attach to the functionalized CS, via the newly created aldehydes, to form a Schiff base intermediate. Sodium cyanoborohydride (5 M, Pierce) was added to the reaction to reduce the Schiff base intermediate imine to a more stable amine. Excess BMPH was removed from the solution by FPLC desalting in deionized water. Due to the absorbance detection capabilities on the ÄKTA Purifier FPLC, the amount of excess BMPH was measured. The small size and low molecular weight of BMPH (297.19 g/mol) resulted in its elution from the column at a separate, much later timepoint. With the presence of its numerous single bonds and occasional double bonds, BMPH produced a strong absorbance spectrum at both the 215 nm wavelength (characteristic of single bonds) and 254 nm wavelength (characteristic of double bonds). Therefore, a standard curve was produced, correlating known BMPH masses to the integrated area of the 215 nm absorbance spectra, FIG. 2. With this standard curve, the mass of excess BMPH was determined. Subtracting the excess BMPH mass from the original reaction mass allows the determination of the mass of BMPH consumed in the reaction. Using the consumed mass, the number of BMPH bound to the oxidized CS was calculated. The collected CS-BMPH product was frozen, lyophilized, and stored at −80° Celsius.

The HA binding peptide sequence was identified by Mummert. Slight modifications to the identified sequence produced the specific HA binding sequence, GAHWQFNAL-TVRGGGC (noted as GAH), that was used in this research. The peptide was produced by and purchased from Genscript (Piscataway, N.J.). The cysteine amino acid was included to allow coupling, by way of thioether bond formation, to the maleimide group of BMPH. This reaction occurs at a 1:1 ratio, allowing the assumption that the number of BMPH bound to the functionalized CS will equal the number of GAH peptides attached. GAH peptide, at one molar excess to the number of BMPH coupled per chain, was dissolved in dimethyl sulfoxide (DMSO, Sigma) and was added to the CS-BMPH solution in 15 minute intervals, a quarter of the volume at a time. After the last addition of GAH peptide, the reaction was allowed to progress for two hours. During this time, the excess GAH peptide formed particulates. Before purifying the solution to obtain GAH functionalized CS, the solution was passed through an Acrodisc 0.8 μm pore diameter filter (Pall, Port Washington, N.Y.) to remove the excess peptide particulates. The solution was then passed, with deionized water, through the ÄKTA Purifier FPLC to purify the GAH−CS compound. The collected compounds were then frozen at −80° Celsius and lyophilized to produce the desired aggrecan-mimics. By laboratory convention, the aggrecan mimic was named by (# of peptides attached) (first three letters of peptide sequence)−(GAG abbreviation that was functionalized) i.e. for the aggrecan mimic, 3GAH−CS for 3 GAH HA binding peptides functionalized to a chondroitin sulfate GAG backbone.

EXAMPLE 3

Binding of Synthetic Peptidoglycan to Hyaluronic Acid

Synthetic Peptidoglycan Binding to Immobilized Hyaluronic Acid

Hyaluronic Acid (HA, from *Streptococcus equi*, Sigma) at a concentration of 4 mg per mL, was immobilized to a 96-well plate (Costar, blk/clr, Corning, Coming, New York) overnight at 4° Celsius. Biotin labeled GAH peptides were bound, by way of BMPH, to functionalized CS at a concentration of 1 biotin-GAH per CS chain. Unlabeled GAH peptides bound to the remaining unreacted aldehydes of CS. Standard biotin-streptavidin detection methods were utilized to determine the degree of aggrecan mimic binding to the immobilized HA. Blocking of the HA surface was done for one hour with 1% Bovine Serum Album (BSA, Sera Care Life Sciences, Milford, Mass.) in 1×PBS solution. After washing with 1×PBS, the biotin-labeled aggrecan mimic was incubated in the well for 30 minutes and then washed with 1×PBS. Streptavidin-horseradish peroxidase (R&D Systems, Minneapolis, Minn.) solution was added to each well, and allowed to react for 20 minutes. After reaction completion and washing, chromogen solution was added (Substrate Reagent Pack, R&D Systems) and developed for 15 min. At 15 min, sulfuric acid (Sigma) was added directly to each well to stop the reaction. The well plate was then read on the M5 SpectraMax Plate Reader (Molecular Devices, Sunnyvale, Calif.) at 450 and 540 nm wavelengths. By subtracting the two absorbance readings produced, the absorbance due to the bound biotin-labeled aggrecan-mimic was determined.

One GAH peptide per aggrecan mimic was replaced by a biotin-labeled GAH peptide and the now-labeled aggrecan mimic was incubated with immobilized HA. Commercially available biotin detection products (through streptavidin and HRP) demonstrated the degree of mimic binding to the immobilized HA (see FIG. 3). Starting at a concentration of 1 μM, the aggrecan mimic had a dose dependent increase in presence on the immobilized HA, proving that the mimic was binding to the HA. However, the determination of the mimic's binding affinity was not pursued due to the uncertainty of the amount of HA immobilized.

Rheometer Derived Synthetic Peptidoglycan Binding to Hyaluronic Acid

HA solutions were created to test the aggrecan-mimic's ability to bind to HA in a more physiologically relevant situation. The ability of the aggrecan-mimic to bind to HA was deduced by the improvement in storage modulus of the solution, indicating HA crosslinking by the mimic. Multiple treatments were created in 1×PBS pH 7.4 to test the aggrecan mimic's ability to bind HA: 2.5 wt % HA control, HA+CS at a 25:1 molar ratio of CS:HA, HA+3GAH−CS at 25:1, HA+7.2GAH−CS at 25:1, HA+10.5GAH−CS at 25:1.

Using the AR-G2 Rheometer (TA Instruments, New Castle, Del.), frequency (0.1-100 Hz, 2.512 Pa) and stress (0.1-100 Pa, 1.0 Hz) sweeps were conducted to measure the storage modulus of each solution.

Rheology studies the flow of a substance in response to applied forces and is often used when measuring viscoelastic materials. In particular, the rheometer determines the storage modulus and the loss modulus based on the substance feedback to the applied force. The storage modulus is a measure of the amount of energy that is elastically absorbed by the substance and the loss modulus depicts the amount of energy lost through heat. A large storage modulus is indicative of a gel-like substance with a more rigid, elastic structure; whereas, a small storage modulus and a large loss modulus indicate a viscous material that does not elastically retain the applied load. The high molecular weight HA (~1.5MDa) is a very viscous material which elastically retains a portion of the applied load due to a pseudo-gel formed by HA chain entanglement. The created aggrecan mimic contains multiple HA binding peptides which can act as a type of HA chain crosslinker assuming adequate mimic binding to the HA. In solution with the high molecular weight HA, it is hypothesized that the aggrecan mimic could increase the rigidity of the solution, creating a larger storage modulus. A larger storage modulus would be indicative of extensive HA crosslinking, proving a strong binding affinity between the aggrecan mimic and the HA chains present in the mixture. Multiple versions of the aggrecan mimic were tested, differentiated by the number of GAH peptides (on average either 3, 7.2, or 10.5) attached per functionalized CS chain.

Figure 3:
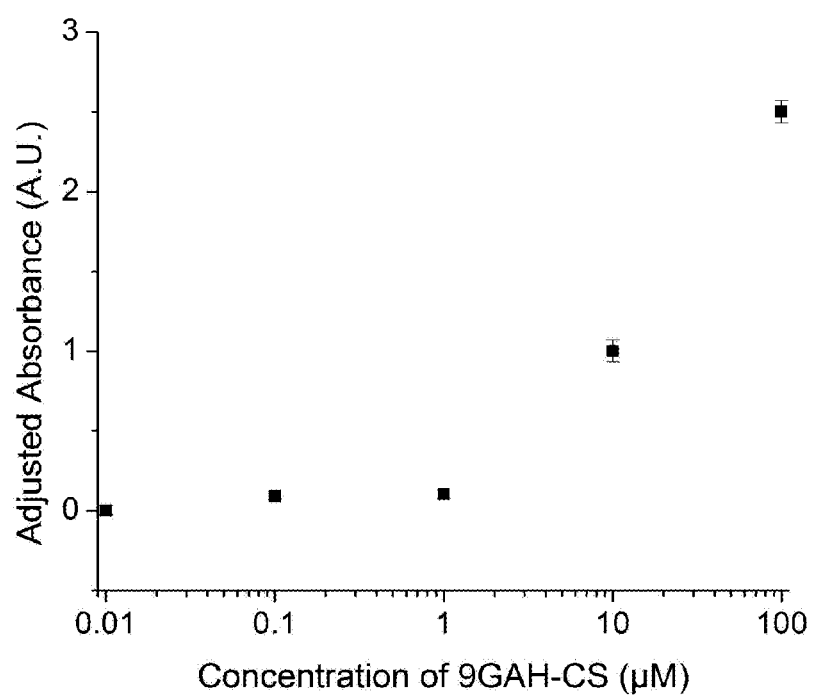
FIG. 3 shows binding of the hyaluronic acid-binding synthetic peptidoglycan to the immobilized hyaluronic acid (HA). Nine HA-binding peptides (e.g., GAHWQFNALTVRGGGC (SEQ ID NO: 35); hereinafter "GAH" or "mAGC") were attached to the functionalized glycosaminoglycan (e.g., chondroitin sulfate, hereinafter "CS") backbone. Concentrations of synthetic peptidoglycans were increased from 0.01 μM to 100 μM.
Figure 4:
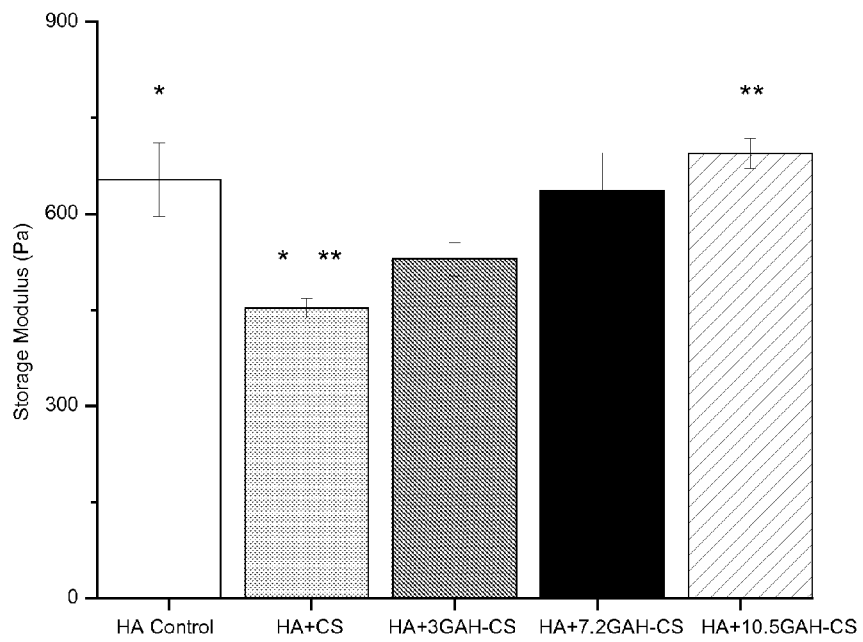
FIG. 4 shows HA binding of the synthetic peptidoglycan as determined by rheological frequency sweep (Panel A). The storage modulus of the HA mixtures was analyzed at an oscillatory frequency of 5.012 Hz. At this frequency, a noticeable load was provided while the integrity of the HA chains was maintained. Statistical analysis ($\alpha=0.05$) showed that HA+CS and HA were significantly different (denoted *), and that HA+10.5GAH–CS and HA+CS were significantly different (denoted **). Panel B is an alternative representation of the same data shown in Panel A.
Figure 4:
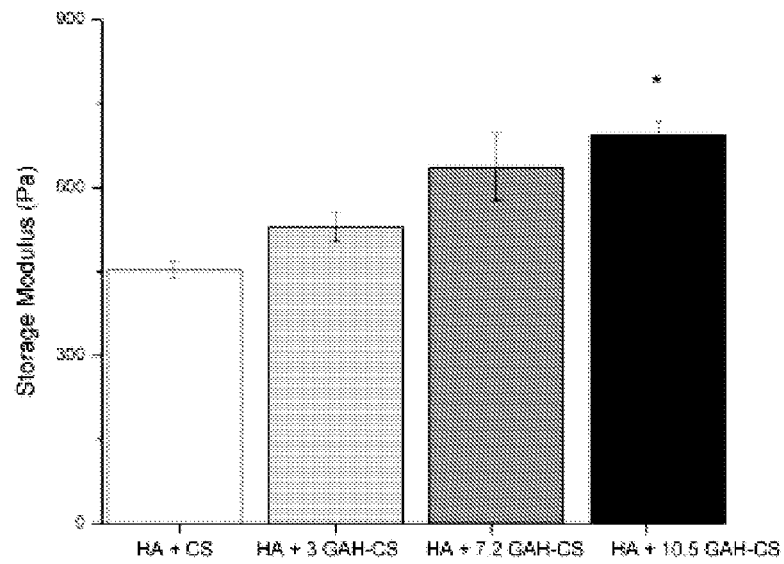

The results of the experiment, shown in FIG. 4, showed that the addition of CS significantly ($\alpha$=0.05) lowered the storage modulus of the HA solution. The addition of the dense negative charges associated with the CS helped spread the HA chains, easing the degree of HA entanglement and removing the pseudo-gel that stored the applied energy. Confirming the hypothesis, as the number of GAH peptides per CS increased from 3 to 10.5, the storage modulus of the mixture increased as well. This increase can be attributed to two beneficial attributes of having a higher number of GAH peptides per aggrecan mimic. First, the more GAH peptides attached per CS, the higher the avidity of the mimic, resulting in a stronger mimic binding to the HA molecule. Second, the more GAH peptides attached per CS, the greater the likelihood of the mimic acting as a crosslinker between the HA molecules. Both effects contributed to a more gel-like mixture, resulting in a larger measured storage modulus. Weaker binding between the mimic and HA would not restore the pseudo-gel and would be unable to store the applied energy from the rheometer. The increase in storage modulus confirms the strong mimic binding to the immobilized HA shown in FIG. 3. Specifically at 10.5 GAH peptides per CS chain, the storage modulus was significantly ($\alpha$=0.05) higher than the HA+CS control, reaching an average storage modulus similar to the HA control.

EXAMPLE 4

Synthetic Peptidoglycan Compression Studies

Collagen Gel Formation and Turbidity

To mimic the native cartilage extracellular matrix, collagen was utilized to entrap the HA and aggrecan-mimic aggregates within a natural scaffold. Collagen type II (CII) was obtained from two different commercial sources (Affymetrix, Santa Clara, Calif. and Sigma). Mixtures of the cartilage ECM components were prepared in TES Buffer (60 mM TES, 20 mM $Na_2HPO_4$, 0.56 M NaCl, chemicals from Sigma) pH 7.6 according to the native component breakdown, where CII comprised 70 dry wt % and the combination of HA and the aggrecan mimic/CS control formed the remaining 30 dry wt % of the mixture. The final concentration of CII in the gel was 2 mg per ml. Samples consisted of a CII control, CII+HA+CS control, and CII+HA+aggrecan mimic (10.5GAH–CS). To prevent premature fibrillogenesis and gel formation, the solutions were kept on ice at an acidic pH. Solution mixtures of the components were placed in a 384 well plate (Greinier blk/clr, Monroe, N.C.), placed at 37° C. and physiological pH to initiate fibrillogenesis, and were monitored at 313 nm on the M5 SpectraMax to determine gel formation. CII was unable to form gels when included with the varying treatments (See Supplementary Information). Therefore, collagen type I (CI, High Concentration Rat Tail Collagen Type 1, BD Biosciences, Bedford, Mass.) was utilized for the gel formation. The same treatments and procedure were used with the CI, except that the component masses were shifted for a CI final concentration of 4 mg per mL. CI was used for all following experiments.

Figure 5:
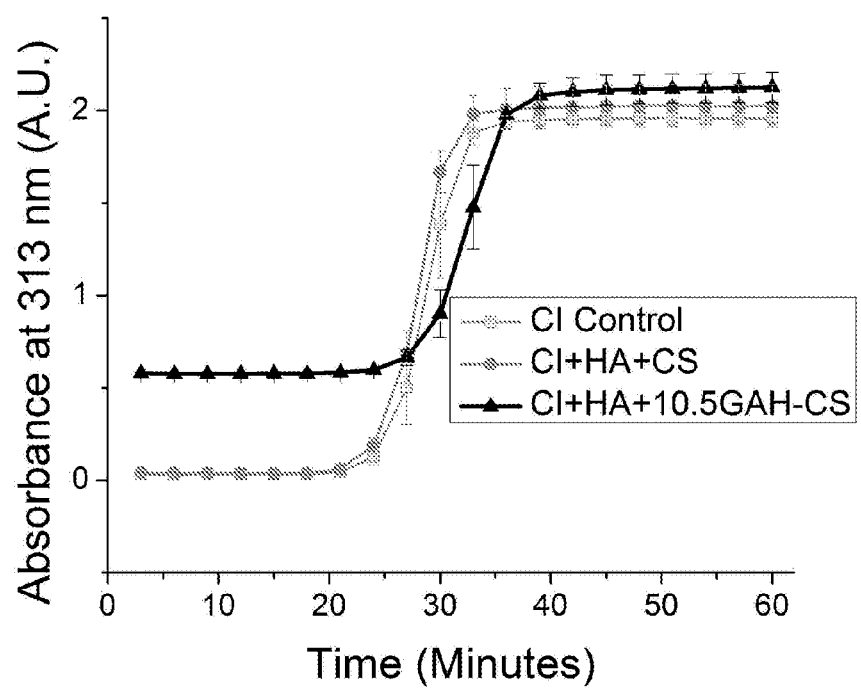
FIG. 5 shows quantification of the turbidity of the collagen type I plus treatment groups during collagen fibril formation. The absorbance at 313 nm was measured every 3 minutes. After one hour (i.e., timepoint number 20), all treatment groups had completely formed networks. No significant differences ($\alpha=0.05$) existed between treatment groups with respect to the maximum absorbance or the time to half maximum absorbance.

Turbidity with CI was performed to measure the formation of the cartilage replicate, results shown in FIG. 5. As demonstrated, the addition of HA+10.5GAH–CS did not affect the fibrillogenesis of the collagen fibers. All treatments followed a similar curve and reached similar absorbance peaks at about the same time. HA+10.5GAH–CS treatment had a higher initial absorbance due to the aggrecan mimics tendency to form self-aggregates in 1×PBS solution, not due to premature CI fibril formation. The aggregation of 10.5GAH–CS was recognized during the initial HA rheometer tests, but the aggregation did not inhibit the aggrecan mimic's ability to bind to HA.

Collagen Gel Property Testing

Collagen-based gel compression tests and frequency sweeps were conducted using an AR-G2 Rheometer using a 20-millimeter parallel plate geometry (TA Instruments). The 375 µL gel mixtures were prepared on ice and pipetted onto the rheometer base plate. The geometry was lowered to a gap distance of 1 mm and the solution was heated to 37° Celsius. A humidity trap was utilized to prevent gel dehydration while the mixture was allowed to gel over two hours. This two hour value was determined by the demonstrated time to gelation data from the turbidity data. After the two hour time period, the gels were compressed or oscillated depending on the test. Compression tests occurred at an engineering strain rate of 1% (10 µm) per second. The gap distance and the normal force on the geometry head were measured. The frequency sweeps measured the storage modulus of the created gels during a logarithmic base ten increase in frequency from 0.1 to 1 Hz.

Figure 6:
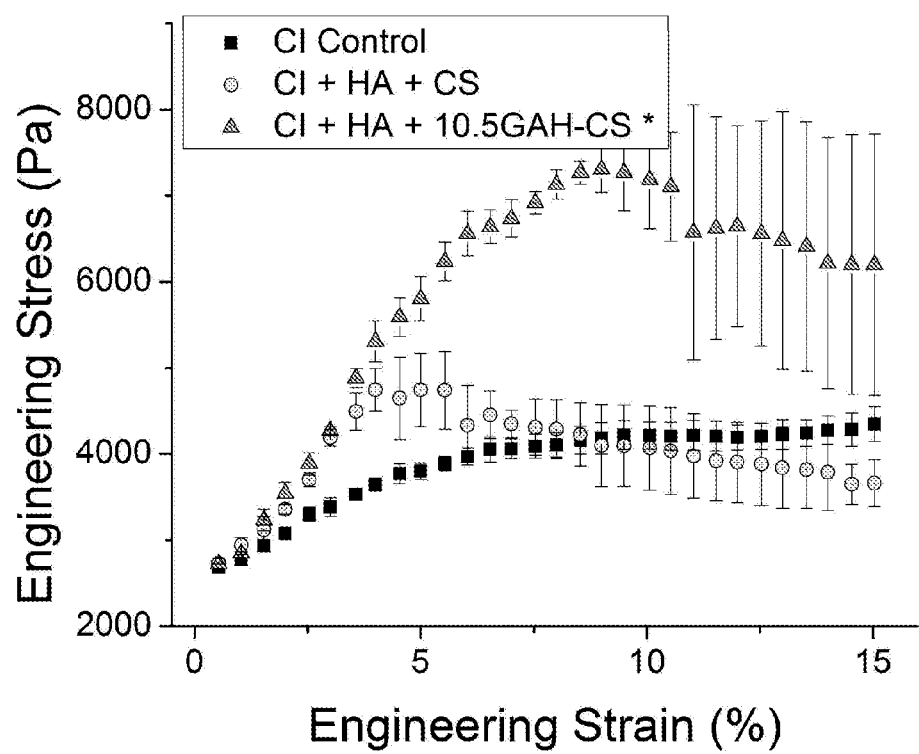
FIG. 6 shows the compressive engineering stress withstood by the collagen gels based on an applied engineering strain of 1% per second. Statistical analysis ($\alpha=0.05$) demonstrated that the addition of 10.5GAH–CS resulted in a significant difference in peak engineering stress, in addition to the engineering stress analyzed at engineering strains of 5%, 7.5%, and 10%.

The simultaneous normal force and displacement were measured, and the engineering stress and strain were calculated for the treatments. As shown in FIG. 6, the inclusion of the aggrecan mimic significantly ($\alpha$=0.05) increased the compressive strength of the gel complex. The peak engineering stress of the collagen+HA+AGG mimic reached 7.5 kPa at an engineering strain of 9%, whereas the collagen+HA+CS control reached a peak of 4.8 kPa at 4%, and the collagen control reached a peak of 4.2 kPa at 15% strain.

Two factors contributed to the increase in compressive strength of the CI+HA+10.5 gel, the first being the mimic's ability to attract water and the second being the HA crosslinking ability of the aggrecan mimic. In native cartilage, the predominance of the entrapped negative charges provided by the HA and CS attract water and retard its diffusion from the cartilage. When a compressive force is applied to the cartilage, the water is not able to diffuse out into the synovial capsule. Retaining this incompressible water increases the compressive strength of the structure. Similarly in the tested gel complexes, the inclusion of the negative charges associated with CS in the gel provides the same attraction. As can be seen in FIG. 6, both the CS and 10.5GAH–CS treatments have an increased compressive strength. The CS treatment is not fixed within the CI complex (it is not bound to HA) and therefore after a small compressive deformation, the CS and its attracted water diffuse out of the complex into the surrounding fluid. The diffusion of the CS and water from the complex diminishes the compressive strength of the complex, causing the resulting gel's compressive profile to resemble that of the collagen scaffold control. In contrast, 10.5GAH–CS is bound to the interwoven HA. Therefore, a much higher compressive stress is required to overcome the binding of the mimic to HA and cause the diffusion of CS and attracted water from the complex.

Figure 7:
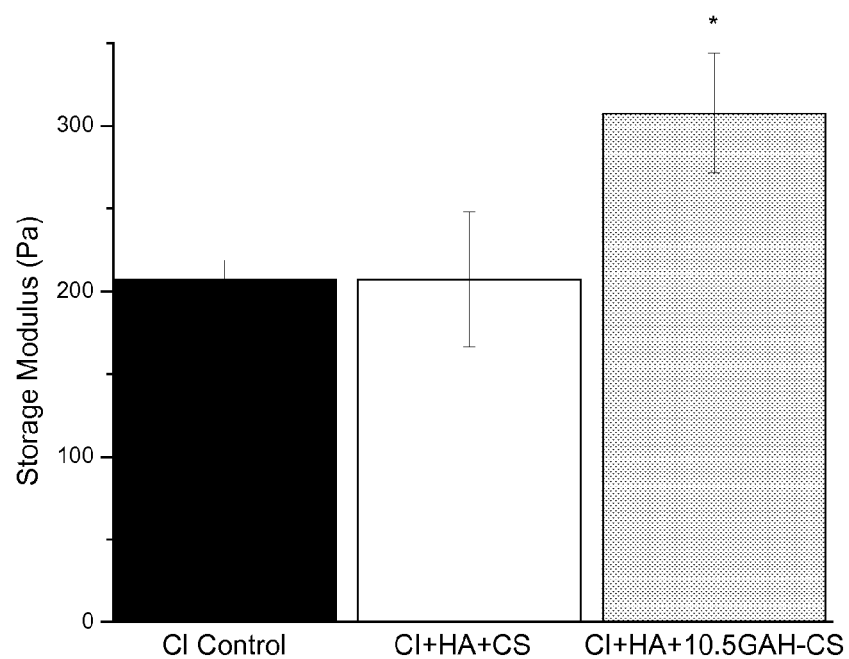
FIG. 7 shows the storage modulus of collagen mixtures measured at an oscillatory frequency of 0.5012 Hz. Statistical analysis ($\alpha=0.05$) demonstrated that the addition of 10.5GAH–CS resulted in a significant increase in the storage modulus of the collagen gel (denoted *).

Secondly, the ability of the aggrecan mimic to act as a HA crosslinker results in a higher degree of entrapment for the HA and mimic. Effectively, the HA crosslinking nature creates large aggregates within the collagen complex, similar to the native aggrecan/HA aggregates. The main difference between the aggrecan mimic and native aggrecan is the size of the molecule. The protein backbone of aggrecan alone weighs ~220 kDa, whereas the aggrecan mimic, in entirety, only weighs around 30 kDa. Therefore, the native aggregate complex, with over 100 aggrecan molecules bound to the HA, produces much larger aggregates than the aggrecan mimic could produce. However, by acting as a crosslinker between HA chains, the aggrecan mimic can produce its own form of an aggregate that also portrays the main characteristics of native aggregates; voluminous, negatively-charged structures. The role of the aggrecan mimic as an HA crosslinker was further investigated by applying shear loads through rheological tests on the CI gels described above. The results of these experiments can be seen in FIG. 7.

The inclusion of 10.5GAH–CS significantly ($\alpha$=0.05) increased the storage modulus of the formed gel. The network created by the binding of the mimic to the HA supplemented the existing rigidity of the CI matrix, allowing an increased elastic absorbance of the energy applied by shear loading. This study was important as it verified the crosslinking ability of the 10.5GAH–CS and the creation of an alternate aggregate form.

EXAMPLE 5

Synthetic Peptidoglycan Protection of Hyaluronic Acid Degradation

Dynamic viscosity values of HA solutions were determined using the AR-G2. High molecular weight HA solutions have a large viscosity due to the extensive chain entanglement caused by the long chain length. Hyaluronidase (Type II from Sheep Testes, Sigma) cleaves the HA chain, creating shorter chains with less entanglement. The shorter HA chains will have a measurably lower viscosity. HA solutions were incubated with 100 units/mL hyaluronidase. Dynamic viscosities were determined using a time sweep with constant angular frequency and oscillatory stress initially and at 2 and 4-hour timepoints. Samples (at 0.5 wt % HA) consisted of HA, HA+CS, and HA+10.5GAH–CS. The treatment values were added at a 75:1 treatment to HA molar ratio. The percent degradation was calculated for each measurement by dividing the initial viscosity from the difference of the measured viscosity minus the initial viscosity.

Work by Pratta et al. and Little et al. has shown the importance of aggrecan in preventing cartilage component degradation. The demolition of the cartilage matrix in osteoarthritis is started with the cleavage of the aggrecan proteoglycans. The removal of the GAG-rich region of the proteoglycan exposes the remaining components, CII and HA, to degrading enzymes. With the knowledge of the importance of aggrecan in preventing degradation, studies were conducted to determine the ability of the aggrecan-mimic in preventing HA degradation.

Figure 8:
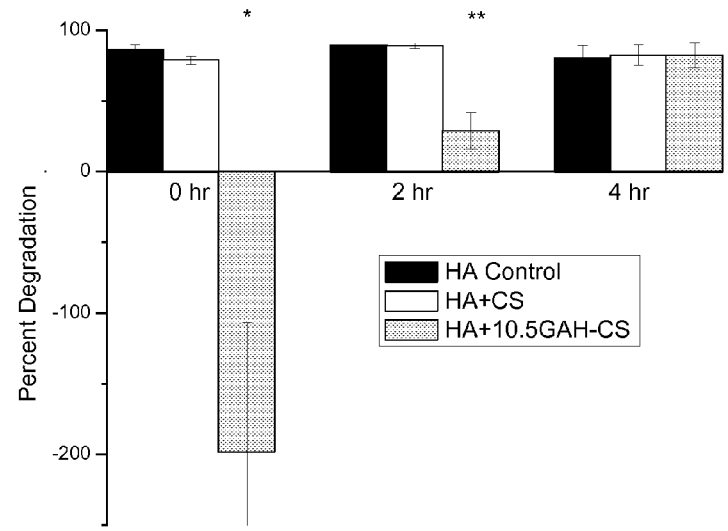
FIG. 8 shows the percent degradation of HA mixtures due to the addition of hyaluronidase to the mixtures (Panel A). The percent degradation was determined by the changes in the dynamic viscosity of the HA mixtures. Dynamic viscosity measurements were initially taken of the mixtures, and served as the baseline from which the percent degradations were calculated. The 0 hour timepoint was taken after the addition of hyaluronidase, the sufficient mixing of the samples, and the pipetting onto the rheometer stage, and approximately 2 minutes passed between the addition of the hyaluronidase and the measurement of the dynamic viscosity. Statistical analysis demonstrated significant differences ($\alpha=0.05$) in the percent degradation for the 10.5GAH–CS sample at both the 0 hour and 2 hour timepoints. Panel B shows the same data represented as normalized dynamic viscosity (mean±SE, n=3) of HA mixtures due to the addition of hyaluronidase. Dynamic viscosity measurements were initially taken of the mixtures before hyaluronidase was added, and these values served as the baseline from which the normalized dynamic viscosities were calculated. The normalized dynamic viscosities were determined by taking each measured dynamic viscosity after the addition of hyaluronidase and dividing this value by the initial dynamic viscosity of that sample. Statistical analysis ($\alpha=0.05$) was conducted, and significant differences were seen in the normalized degradation for the 10.5GAH–CS sample at both the 0 hr and 2 hr timepoints.
Figure 8:
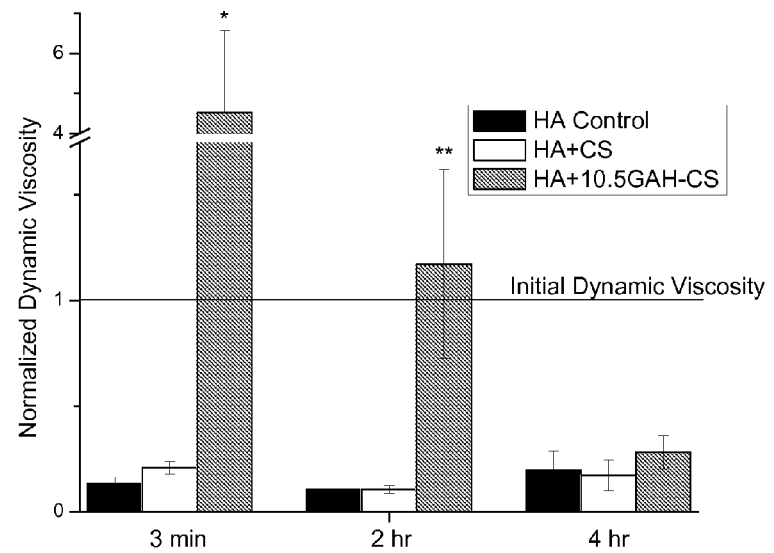

The viscosity of a HA solution is dependent on the size of the HA chains. Due to entanglement, larger HA chains will produce a higher viscosity. When exposed to hyaluronidase, the HA chain is cleaved into smaller units. Therefore, the size of the HA and the amount of HA entanglement decreases. This decrease prompts a similar decrease in the measured viscosity. The percent change in viscosity of HA solutions in the presence of hyaluronidase will provide key information into the amount of degradation the HA has undergone. FIG. 8 presents the percent degradation of HA control versus the associated treatments. As can be seen, the AGG mimic, GAH, significantly reduced the rate of degradation of HA, indicating that it behaves similarly to native AGG in its protection of ECM components.

Viscosities of each treatment without hyaluronidase (TES Buffer replaced the hyaluronidase volume) were initially measured and served as the baseline for the percent degradation calculations. The 0 hr timepoint involved the addition of the hyaluronidase, mixing of the solution, pipetting onto the rheometer, and the beginning equilibration operation of the machine. Therefore, the 0 hr timepoint occurred approximately two minutes after the addition of hyaluronidase. A high concentration of hyaluronidase (25 units per mL) was utilized to replicate the worst possible scenario. In addition, the HA molecules were dispersed in solution, rather than tightly interwoven into a collagen network. As can be seen from FIG. 8, both the HA Control and the HA+CS treatment had almost complete degradation of the HA solution at the 0 hr timepoint. In contrast, the addition of 10.5GAH–CS significantly ($\alpha$=0.05) reduced the amount of HA degradation. In fact, the presence of 10.5GAH–CS increased the viscosity above the baseline values. It is believed that the addition of hyaluronidase cleaves some of the excess HA. This allows 10.5GAH–CS to better crosslink the remaining, intact chains, creating a denser gel which produced the larger viscosity.

At the 2 hr timepoint, both the HA control and HA+CS had completely degraded with percent degradations above 90%, but the HA solution with 10.5GAH–CS had a significantly ($\alpha$=0.05) lower percent degradation. Lastly, at the 4 hr timepoint, all treatments had been degraded, with their percent degradations all above 90%. Amongst the three timepoints, 10.5GAH–CS was not able to completely prevent HA degradation, but it drastically reduced the rate of degradation compared to the degradations of the HA Control and HA+CS. This reduced rate demonstrates that the 10.5GAH–CS prevents the degradation of the HA chains. It is believed that this prevention is being accomplished through competitive inhibition of the hyaluronidase cleavage point on the HA chain. The non-covalent binding of the mimic to the HA chain coupled with the gradual degradation rate of the HA chains appear to validate this belief. In addition, the degradation rate of the 10.5GAH–CS solution is still believed to be artificially high. Upon incubation of the mimic within the HA solution, HA+10.5GAH–CS aggregates were formed. However, these aggregates did not spread uniformly throughout the solution volume. Therefore, the solutions were mixed, similarly to the other samples, before a measurement was taken. The mixing of the solution disrupted the aggregates, dislodging 10.5GAH–CS and exposing the hyaluronidase cleavage point. Even after the 4 hr timepoint, when supposedly complete degradation had occurred, substantial aggregation of HA+10.5GAH-CS still occurred. In a compact matrix like the ECM of cartilage, it is possible that 10.5GAH–CS could not only significantly reduce the degradation rate, but suppress HA degradation.

EXAMPLE 6

CryoScanning Electron Microscopy (SEM)

The ECM-based constructs, as described for turbidity measurements, were formed on an SEM plate at 37° C. overnight. The SEM plates were secured into a holder, and were plunged into a liquid nitrogen slush. A vacuum was pulled on the sample as it was transferred to the Gatan Alto 2500 prechamber. Within the chamber, cooled to –170° C., a cooled scalpel was used to create a free break surface on the sample. The sample was subjugated to sublimation at –85° C. for 15 minutes followed by a sputter-coating of platinum for 120 seconds. After sputter-coating, the sample was transferred to the microscope stage and images were taken at –130° C.

Figure 9:
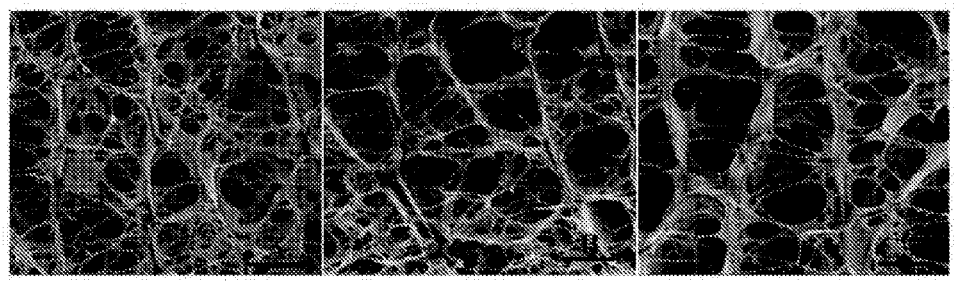
FIG. 9 shows representative cryo-SEM images (10,000× magnification with 5 μm scale bar) of the CI scaffold associated with each cartilage ECM replicate. Panel A represents the CI control. Panel B represents CI+HA+CS. Panel C represents CI+HA+10.5GAH–CS.

Representative images were obtained at a magnification of 10,000x, as shown in FIG. 9. Panel A shows the CI control, and is characterized by extensive crosslinking between major fibrils, and relatively small matrix pore size. Panel B shows CI+HA+CS, and contains extensive crosslinking, but larger pore size, due to the presence of the large HA chains. Panel C shows CI+HA+10.5GAH–CS and illustrates a noticeably smaller degree of crosslinks in addition to a very large pore size. The AGG mimic can bind to the HA creating a relatively large, cumbersome complex that hinders the CI crosslinking.

As can be qualified in the representative images, the addition of HA+CS did not have an effect on the variation of collagen fibril diameters, but the HA+CS sample did have a larger representative void space. In comparison to the control groups, the addition of the AGG mimic with the HA resulted in a smaller variation of collagen fibril diameters due to the limited number of small fibril diameters, and an overall increase in the void space of the sample. The binding of the AGG mimic to the HA molecule created an aggregate complex that was trapped within the collagen scaffold and excluded smaller fibril formation between the larger fibrils due to steric hindrance.

EXAMPLE 7

Collagen Protection

ECM-based constructs containing collagen alone, collagen+HA+CS, or collagen+HA+10.5GAH–CS were created in 8-well chambered slides as described previously. The final sample volume was 200 µL consisting of 0.8 mg of collagen type I. Matrix metalloprotease-I (MMP-I, R&D Systems, Minneapolis, Minn.) at a concentration of 0.133 mg/mL, was activated following the protocol detailed in the manufacturer's instructions. Briefly, MMP-1, already dissolved in manufacturer's buffer (50 mM Tris, 10 mM $CaCl_2$, 150 mM NaCl, 0.05% Brij-35, pH 7.5), was combined with an equal volume of 25 mM APMA (Sigma) in DMSO at 37° C. for 2 hrs to activate the enzyme. Upon activation, the MMP-1 solution was diluted two fold in water and was added to the sample as a 100 µL supernatant. The samples were incubated at 37° C. with gentle shaking Twenty-five hrs after the addition of the initial enzyme solution, the supernatant was removed and replaced with a fresh batch of enzyme. After 50 total hr of incubation with the enzyme, the remaining gels were removed from the chambered slides, washed with deionized water to remove any enzyme solution or degradation products, and resolubilized in 12 M HCl. The samples were diluted in water to reach a final concentration of 6 M HCl, and were hydrolyzed overnight at 110° C. Following hydrolysis, the amount of hydroxyproline (hyp) was analyzed according to the protocol developed by Reddy, et al. (*Clin Biochem,* 1996, 29: 225-9). Briefly, the hydrolyzed samples were incubated with Cholramine T solution (0.56 M) for 25 minutes at room temperature before the addition of Elrich's reagent and subsequent chlorphore development for 20 minutes at 65° C. After the development of the chlorophore, the samples were read on a spectrophotometer at a wavelength of 550 nm. Absorbance readings were compared to those obtained from known concentrations of collagen to determine the amount of collagen remaining in each sample.

Figure 10:
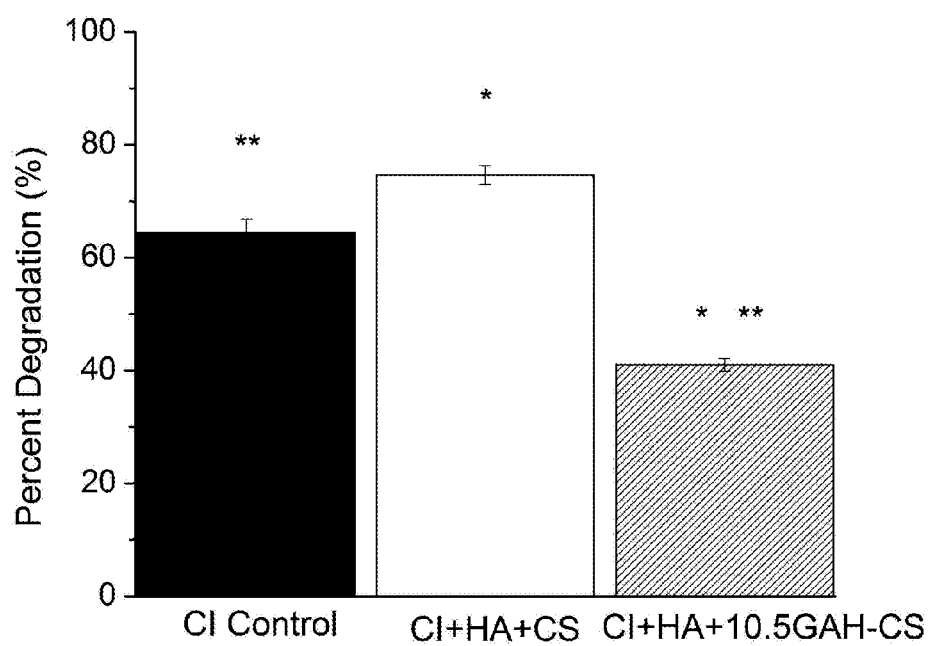
FIG. 10 shows the percent degradation (mean±SE, n=3) of CI in ECM replicates exposed to MMP-I throughout a 50 hr duration. Statistical analysis (p<0.05) of the different treatments revealed that all three treatments (CI control, CI+HA+CS, and CI+HA+10.5GAH–CS) were significantly different from each other.

Each replicate sample was constructed with 0.8 mg of CI, and after degradation, the remaining CI amount was determined by the protocol developed by Reddy et al. and converting that to CI amount by a set of CI standards. The percent degradation was determined by subtracting the remaining CI from the initial CI, dividing by the initial CI, and multiplying by 100. The percent degradation of the three treatments is shown in FIG. 10. All the treatments were significantly different from each other (p<0.05). In particular, the percent degradation of the AGG mimic sample (CI+HA+10.5GAH–CS=41.0%) was significantly less (p<0.05) than the other two treatments (CI=64.5% and CI+HA+CS=74.7%). The presence of the AGG mimic significantly reduced the CI degradation. The presence of the AGG mimic can act as a hindrance to the cleavage sites of the degrading enzymes. By creating the large aggregates with HA that are tightly trapped within the collagen scaffold, the AGG mimic can occupy the space proximal to the collagen, preventing enzyme access to degradation locations.

EXAMPLE 8

Diffusion of Peptidoglycans Through Cartilage Matrix

Figure 13:
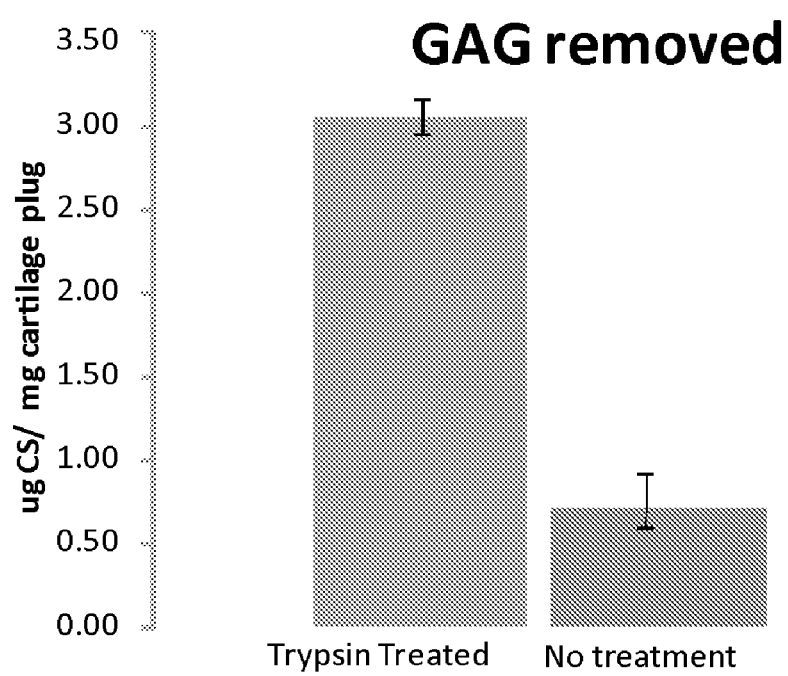
FIG. 13 represents a platform to study the efficacy of the peptidoglycan ex vivo. 0.5% trypsin was used to remove native aggrecan from bovine cartilage explants. Removal of aggrecan was confirmed by DMMB assay. Graphs represent the amount of aggrecan removed compared to positive control.
Figure 14:
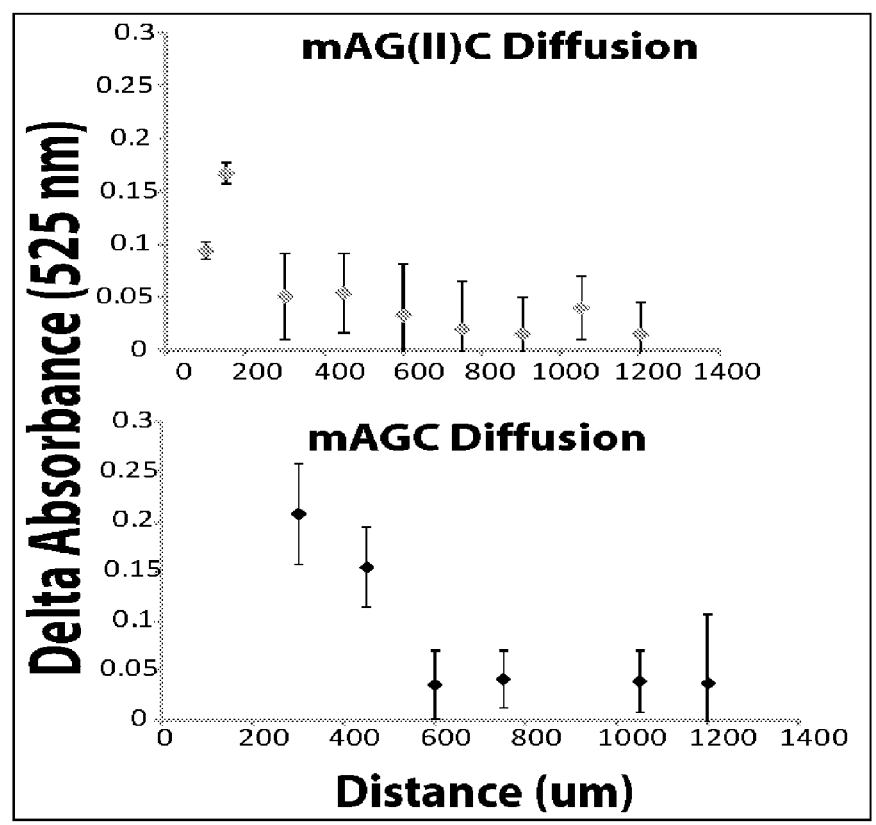
FIG. 14 shows an assay to monitor peptidoglycan diffusion through the cartilage matrix. The Y-axis represents the difference in DMMB assay absorbance values read from aggrecan-depleted cartilage plugs treated with/without peptidoglycan. The X-axis represents the distance from the articular surface of cartilage to subchondral bone. Bars represent average difference ±SEM (n=3).
Figure 15:
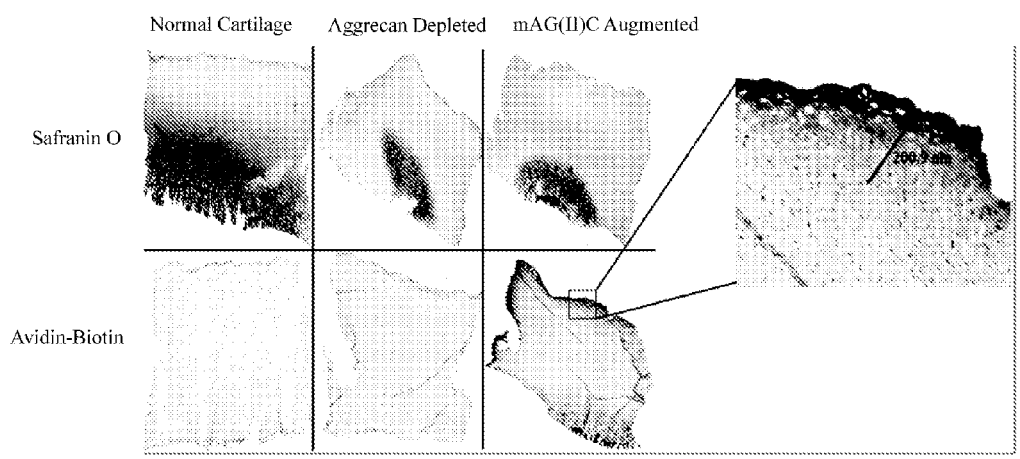
FIG. 15 shows Safranin O and Avidin-Biotin stains of bovine cartilage explants. A midsagittal cut was made through the matrix and probed for residual aggrecan (top panel, dark staining) and biotin (bottom panel, dark staining) respectively. Collagen type II binding peptidoglycan [WYR-GRLGC (SEQ ID NO: 36); "mAG(II)C"] was diffused through the explant. Higher magnification (20×) of this tissue slice indicated that mAG(II)C penetrates approximately 200 um into tissue.
Figure 16:
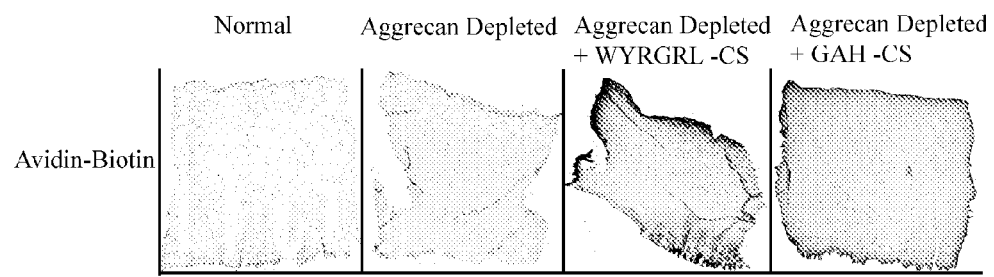
FIG. 16 shows Avidin-Biotin stains of cartilage explants. Peptidoglycans (mAG(II)C and mAGC) were diffused through the cartilage explant. Images indicate depth of penetration of each (dark staining).

Cartilage explants were obtained from the load bearing region of three month old bovine knee joints. Native aggrecan was removed from harvested cartilage explants leaving a matrix consisting primarily of type II collagen and residual GAG. This was achieved by treating explants with 0.5% (w/v) trypsin in HBSS for 3 hours at 37° C. (FIG. 13). After trypsin treatment explants were washed three times in HBSS and incubated with 20% FBS to inactivate residual trypsin activity. Peptidoglycan was dissolved in distilled water at 10 µM concentration and diffused through the articular surface of cartilage explants by placing 10 µL of the solution on the surface every ten minutes for one hour at room temperature (FIG. 14). Normal cartilage and aggrecan depleted cartilage were treated with 1×PBS as positive and negative controls respectively. After diffusion, explants were washed three times with 1×PBS and stored at –20° C. until further testing. Diffusion of peptidoglycan was confirmed by staining a midsagittal section of the tissue with streptavidin-horseradish peroxidase stain. The streptavidin stain binds to the biotin labeled molecule and is depicted as a brown color (FIGS. 15 and 16).

EXAMPLE 9

Bulk Compression Testing

Figure 17:
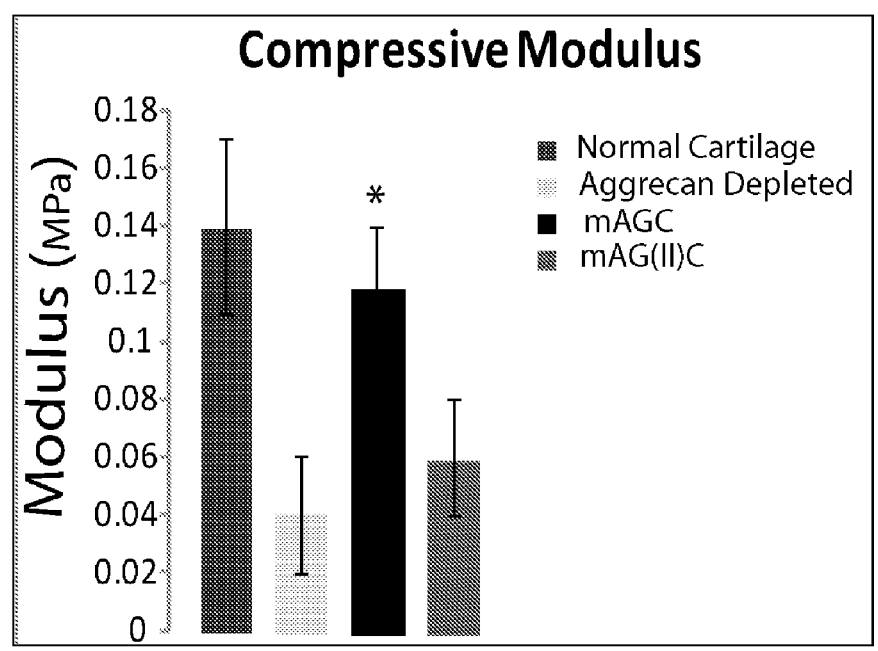
FIG. 17 shows that the addition of peptidoglycans in aggrecan depleted (AD) explants increased compressive stiffness. Addition of the HA binding peptidoglycan (mAGC) significantly restored stiffness of cartilage explants to a higher extent as compared to the collagen type II binding peptidoglycan (mAG(II)C). Significance, denoted as *, specified an increase in compressive stiffness between AD and AD+mACG augmented explants (p<0.005). Data is presented as mean±SEM (n=5).

Displacement-controlled unconfined compression was performed on an AR G2 rheometer with force transducers capable of detecting normal forces in the range of 0.01-50 N (TA Instruments). The explants were glued to the bottom of a hydrophobic printed slide (Tekdon) and covered in a 1×PBS bath. A 20 mm diameter stainless steel parallel plate geometry head was lowered until initial contact was made. Explant height was measured using a digital micrometer (Duratool). Compressive loads from 0-30% nominal strain (at 5% intervals) were applied to the explants through a stepwise loading that involved a ramp duration of 5 sec (i.e. a strain rate of 1.0%/sec) and hold time of 30 sec. Compressive stiffness values were obtained by using the slope of equilibrium stress values, computed during each hold section, versus respective strain values, based on a linear fit model. Scaffolds tested for bulk compression included: 1) Normal cartilage, 2) Aggrecan depleted cartilage (AD), and 3) AD+mAGC (FIG. 17). Addition of the HA binding peptidoglycan (mAGC) significantly restored stiffness of cartilage explants to a higher extent as compared to the collagen type II binding peptidoglycan (mAG(II)C).

EXAMPLE 10

Animal Model

Sprague-Dawley rats (250-300 g) were used for surgery. The patellar tendon, the anterior and posterior cruciate ligaments and the medial, lateral collateral ligaments were transected. The medial and lateral meniscuses were totally menisectomized. The knee joint capsule was repaired with an absorbable suture and the skin was closed with a 4-0 monofilament nylon. Starting at week 4, 10 µl of a 1 µm mAGC was administered weekly.

Figure 18A:
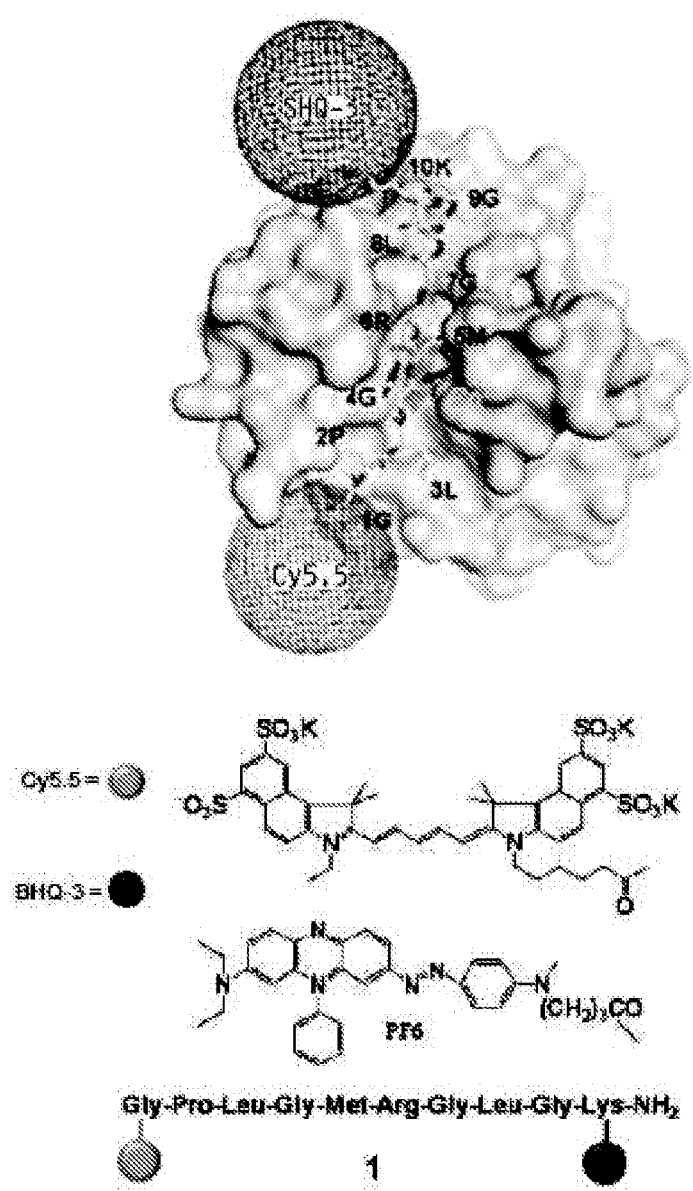
FIG. 18 (A) shows a schematic representation of probe bound to MMP-13. BHQ-3 black hole quencher 3 and CY5.5 absorbed and emitted at 695 nm respectively. Arrow and italics indicate the cleavage site. (B) shows the concentration profile of probe activity with and without MMP-13: Left, fluorescence imaging sections of 96-well microplate; Right, recovery of fluorescence emission intensity (695 nm).
Figure 18B:
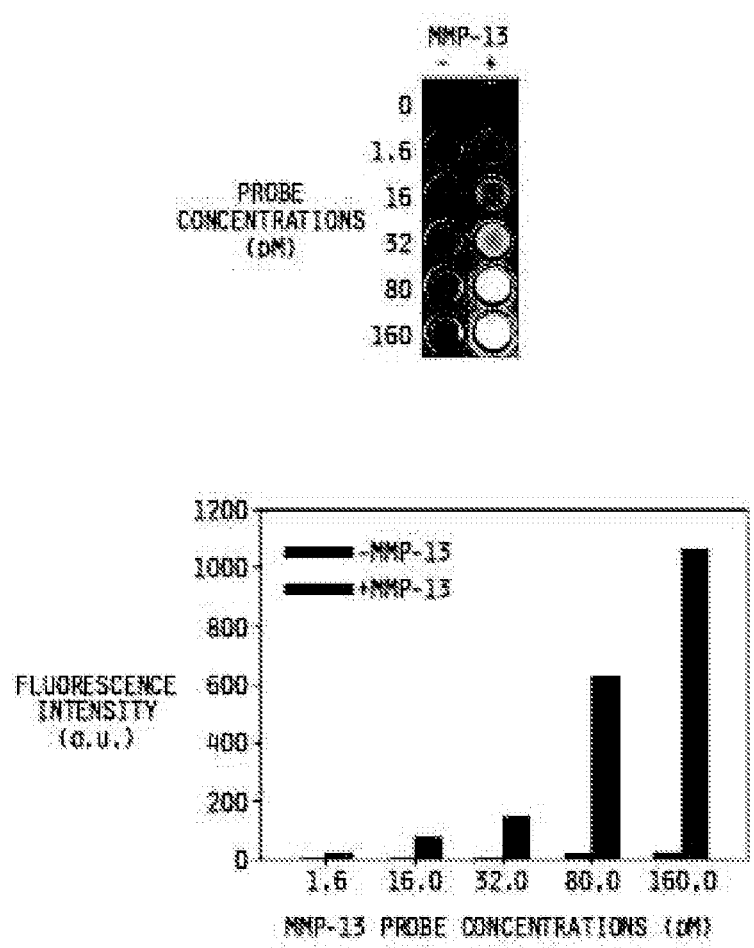
Figure 19:
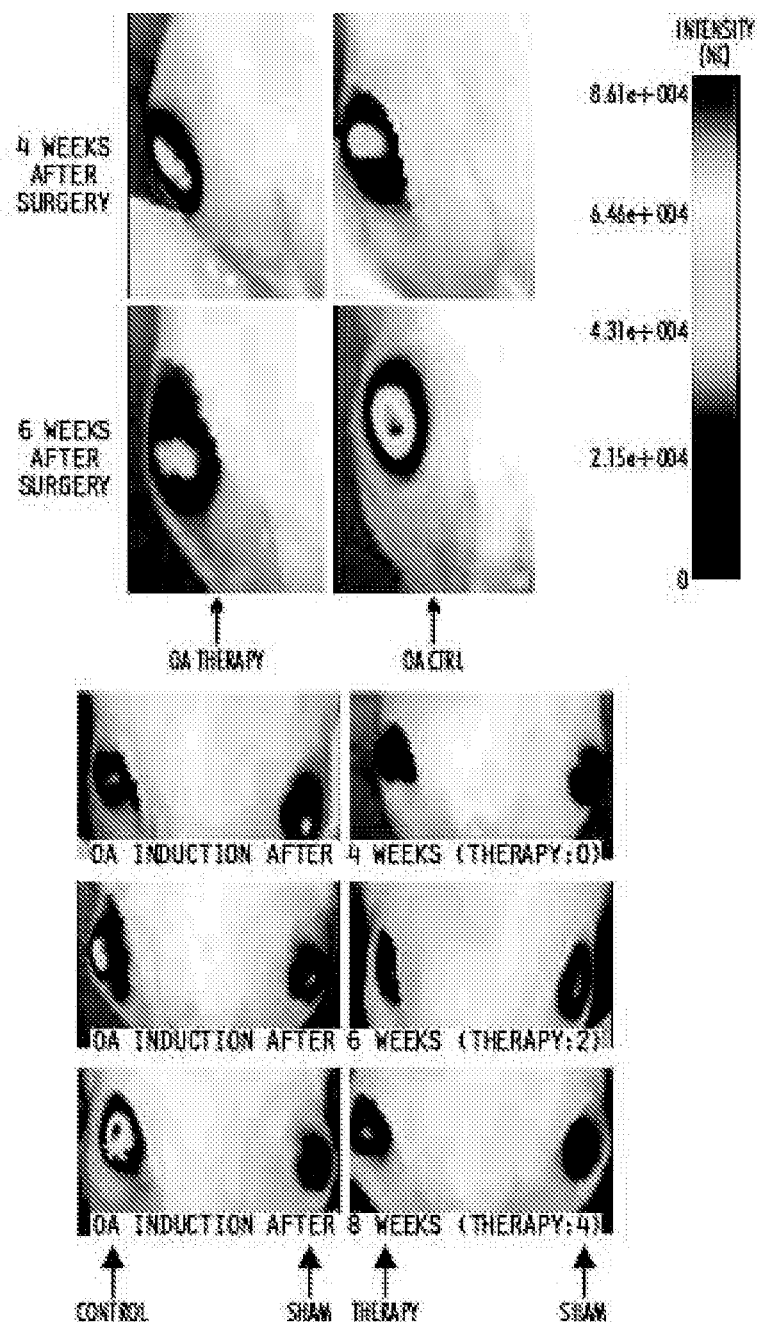
FIG. 19 shows the extent of inflammation indicated by the MMP-13 probe in Sprague-Dawley rats treated with and without peptidoglycan at four, six and eight weeks post surgery.
Figure 20:
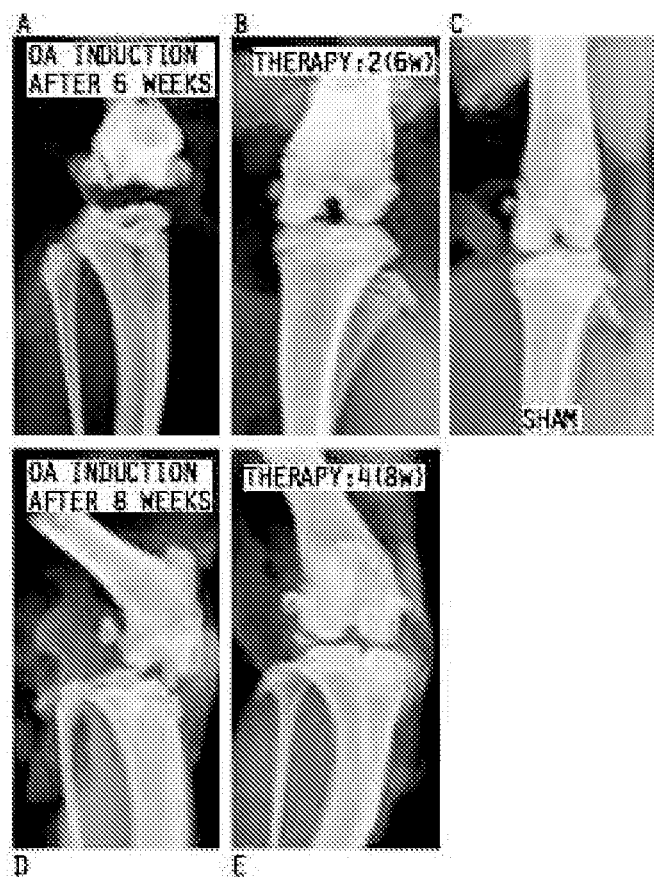
FIG. 20 shows a x-ray images of Sprague-Dawley rat knee joints showing injured knee 6 weeks and 8 weeks following QA induction (Panels A and D, respectively), injured knee with peptidoglycan treatment (Panels B and E, respectively), and normal knee (Panel C) six weeks after osteoarthritis induction surgery.
Figure 21:
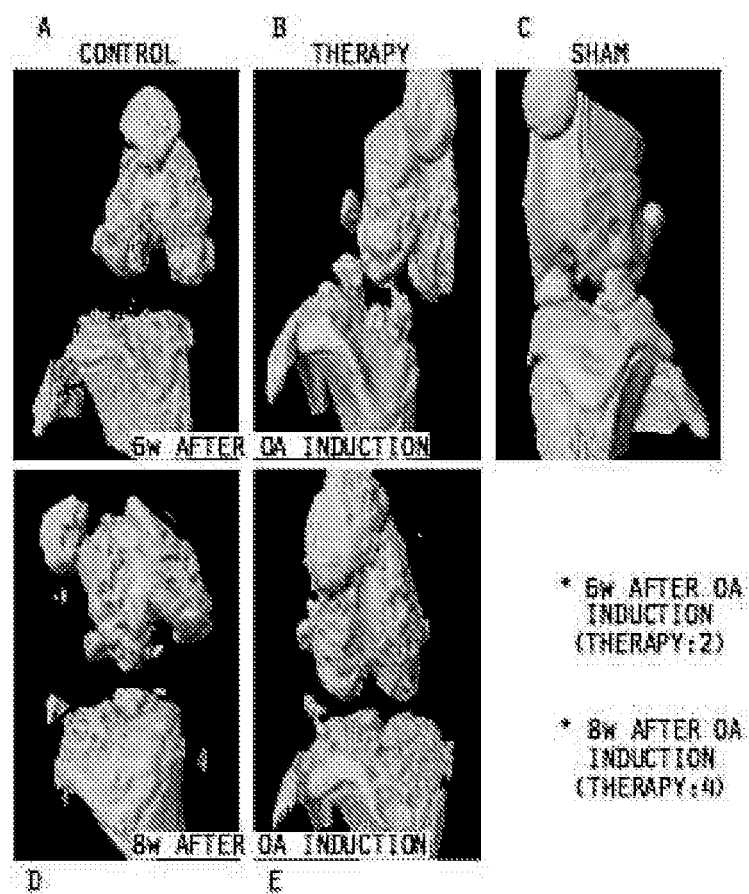
FIG. 21 shows microCT of Sprague-Dawley rats indicating re-growth of new cartilage six and eight weeks after QA induction surgery. Injured knees 6 weeks and 8 weeks following QA induction are shown in Panels A and D, respectively. Injured knees following peptidoglycan treatment are shown in Panels B and E, respectively. Normal knee is shown in panel C.

The extent of inflammation was indicated by the MMP-13 probe (FIG. 18) in Sprague-Dawley rats treated with and without peptidoglycan at four, six and eight weeks post surgery (FIG. 19). X-ray images of Sprague-Dawley rat knee joints showed injured knee 6 weeks and 8 weeks following OA induction (FIG. 20, Panels A and D, respectively), injured knee with peptidoglycan treatment (FIG. 20, Panels B and E, respectively), and normal knee (FIG. 20, Panel C) six weeks after osteoarthritis induction surgery. MicroCT of Sprague-Dawley rats indicated re-growth of new cartilage six and eight weeks after OA induction surgery. Injured knees 6 weeks and 8 weeks following OA induction, (FIG. 21, Panels A and D, respectively), injured knees following peptidoglycan treatment (FIG. 21, Panels B and E, respectively), and Normal knee (FIG. 21, Panel C), are shown.

EXAMPLE 11

Reagents

Peptide GAHWQFNALTVRGGGC (GAH) was purchased from Genscript (Piscataway, N.J.). N-[β-maleimidopropionic acid]hydrazide, trifluoroacetic acid salt (BMPH) was purchased from Pierce (Rockford, Ill.). Rat tail type I collagen was purchased from BD Biosciences (Bedford, Mass.). Human recombinant interlukin-1β was purchased from Peprotech (Rocky Hill, N.J.). All other supplies were purchased from VWR (West Chester, Pa.) or Sigma-Aldrich (St. Louis, Mo.) unless otherwise noted.

EXAMPLE 12

Collagen Scaffold Synthesis

Collagen scaffolds were prepared in TES buffer (60 mM TES, 20 mM $Na_2PO_4$, 0.56 M NaCl) at a pH of 7.6. Scaffold composition for mechanical testing and in vitro inflammatory model studies are described in their respective sections. All solutions were maintained on ice until fibrillogenesis was initiated at 37° C. Aligned collagen scaffolds were created by placing the collagen solution at the isocenter of a 9.4 Tesla magnet (Chemagnetics CMX400) at 37° C. for one hour, whereas unaligned gels were prepared similarly but without magnetic exposure. The slide containing the collagen solution was placed parallel to the magnetic field, orienting the collagen fibers in a direction perpendicular to the bottom of the slide. The gels were then maintained at 37° C. for 24 hours in a humidity-controlled chamber to prevent evaporation.

EXAMPLE 13

Rheological Mechanical Testing

Shear and compression testing was performed on a stress-controlled AR G2 rheometer (TA Instruments) using a 20 mm diameter stainless steel parallel plate geometry head. Collagen scaffolds were prepared on 20 mm diameter hydrophobic printed slides (Tekdon). For shear tests, the geometry head was lowered until contact was made at a gap height of 950 µm. Preliminary frequency and stress sweeps were performed to determine a linear and stress-independent storage modulus range. Frequency sweeps were then performed on all gels with an oscillatory stress of 0.2 Pa over a frequency range of 0.1 to 2 Hz. For compression tests, the geometry head was lowered until contact was made with the scaffold at a gap height of 1000 µm. Compressive loads from 0-30% nominal strain (at 5% intervals) were applied to the collagen scaffold through a stepwise loading that involved a ramp duration of 5 sec (i.e. a strain rate of 1.0%/sec) and hold time of 30 sec. Compressive stiffness values were obtained by using the slope of equilibrium stress values, computed during each hold section, versus respective strain values, based on a linear fit model. Collagen scaffold composition for mechanical tests were:

1) Unaligned collagen, 2) Aligned collagen, 3) Unaligned collagen+mAGC and 4) Aligned collagen+mAGC.

Figure 22:
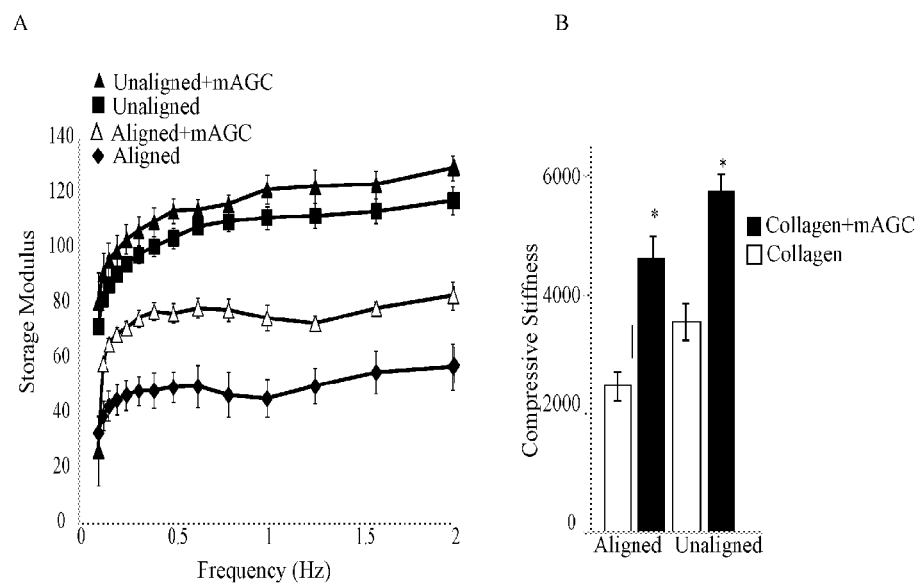
FIG. 22 shows that the addition of mAGC to collagen scaffolds increased the storage modulus and compressive stiffness. Frequency sweeps (A) on collagen scaffolds indicated an increase in storage modulus over a range of 0.1-2.0 Hz. Similarly, compressive stiffness (B) showed an increase in values when the scaffold was prepared with the addition of mAGC. Significance is denoted as * (p<0.0001). Data is presented as mean±SEM (n=5).
Figure 23:
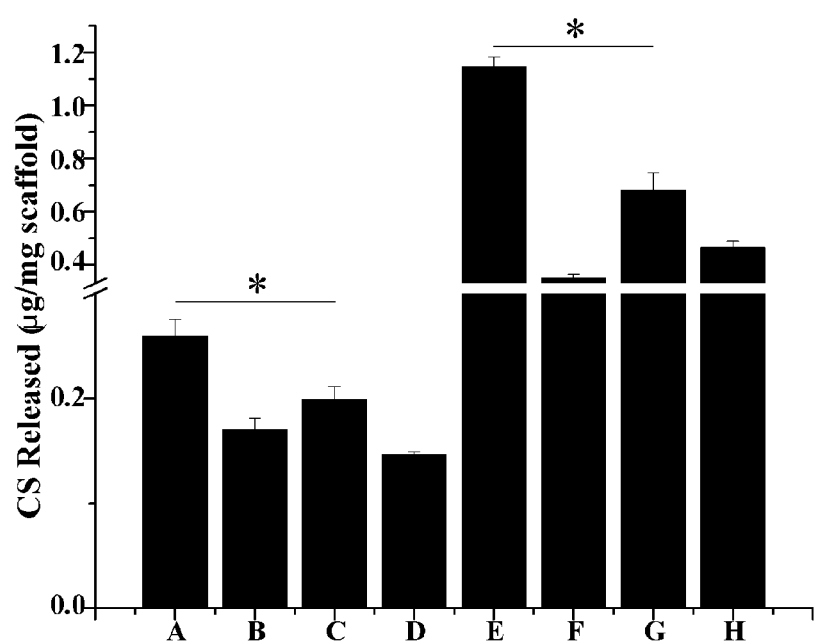
FIG. 23 shows cumulative chondroitin sulfate (CS) loss over an eight-day culture period in media stimulated with and without IL-43. CS loss was measured by a DMMB assay. Scaffold compositions (A-H) are described in Table 3. The addition of mAGC had a significant effect on loss of CS from the scaffolds (p<0.001). * denotes statistical significance between scaffold A and C, and scaffold E and G. (p<0.05). Bars represent average ±SEM (n=3).
Figure 24:
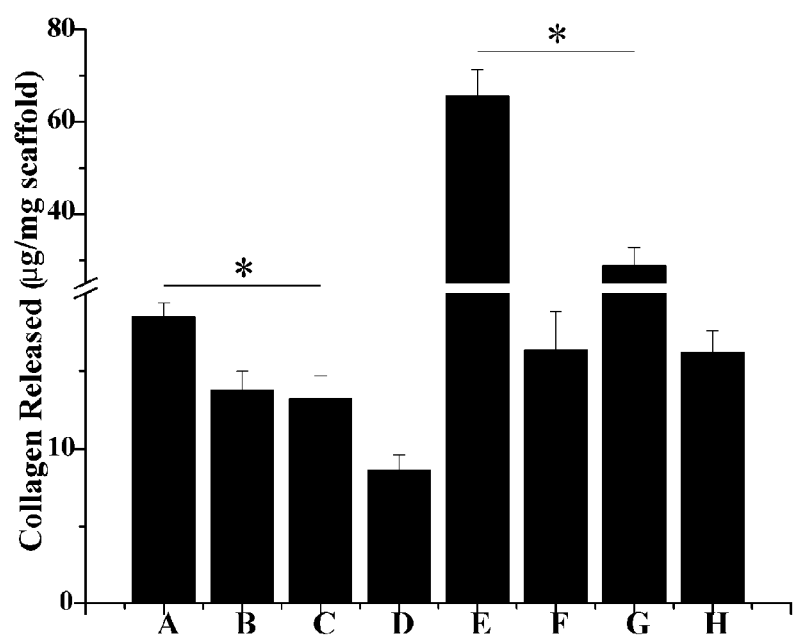
FIG. 24 shows cumulative collagen breakdown over an eight-day culture period in media stimulated with and without IL-1β. Collagen breakdown was measured by a Sircol assay. Scaffold compositions (A-H) are described in Table 3. The addition of aggrecan mimic had a significant effect on loss of collagen from the scaffolds (p<0.02). * denotes statistical significance between scaffold A and C, and scaffold E and G. (p<0.05). Bars represent average ±SEM (n=3).

Bulk Mechanical Analysis:

The aggrecan mimic, mAGC, enhanced bulk mechanical properties of scaffolds, irrespective of fiber alignment (FIG. 22). For shear testing, the storage moduli values at 0.5 Hz for unaligned and aligned collagen gels were 104.1±3.6 Pa and 49.9±5.4 Pa respectively. The addition of mAGC to the collagen scaffold showed a significant increase in the storage moduli of the unaligned and aligned gels to 113.9±4.6 Pa and 76.6±3.6 Pa respectively (p<0.001). Unaligned gels showed a higher storage modulus as compared to aligned gels (p<0.0001). For compression testing, the compressive stiffness for aligned scaffolds (2478±250 Pa) was lower than unaligned scaffolds (3564±315 Pa) (p<0.001). Addition of mAGC to these scaffold systems increased compressive stiffness of the aligned and unaligned scaffolds to 4626±385 Pa and 5747±306 Pa, respectively (p<0.0001).

EXAMPLE 14

In Vitro Inflammation Model

Collagen scaffolds seeded with chondrocytes were stimulated with IL-1β and assessed for degradation products.

Chondrocyte Isolation:

Primary chondrocytes were harvested from three-month-old bovine knee joints obtained from an abattoir within 24 hours of slaughter (Dutch Valley Veal). Cartilage slices, 150-200 µm thick, were shaved from the lateral femoral condyle and washed three times in serum-free DMEM/F-12 medium (50 µg/mL ascorbic acid 2-phosphate, 100 µg/mL sodium pyruvate, 0.1% bovine serum albumin, 100 units/mL penicillin, 100 µg/mL streptomycin and 25 mM HEPES) prior to digestion with 3% fetal bovine serum (FBS) and 0.2% collagenase-P (Roche Pharmaceuticals) at 37° C. for six hours. Released chondrocytes were filtered through 70 µm cell strainer and centrifuged at 1000 rpm three times for five minutes each in medium listed above supplemented with 10% FBS. The cell pellet was resuspended in 10% FBS supplemented media and plated on 10 cm dishes at 10,000 cells/mL in a 37° C., 5% $CO_2$ humidified incubator until confluent.

Scaffold Fabrication:

Upon reaching confluency, cells were trypsinized and encapsulated at 10,000 cells/mL within collagen scaffolds (Table 3) and allowed to equilibrate for 3 days prior to treatment.

TABLE 3

Scaffold composition for in vitro testing

Unaligned Collagen Experimental Setup

A: Collagen + CS + HA + IL-1β
B: Collagen + CS + HA
C: Collagen + mAGC + HA + IL-1β
D: Collagen + mAGC + HA Aligned Collagen Experimental Setup E: Collagen + CS + HA + IL-1β
F: Collagen + CS + HA
G: Collagen + mAGC + HA + IL-1β
H: Collagen + mAGC + HA Inflammation Model:

Constructs were incubated with or without 20 ng/mL IL-1β in chemically-defined media supplemented with 5% FBS and antibiotics (100 units/mL penicillin and 100 µg/mL streptomycin). Culture medium was replaced every two days. Removed media extracts were stored at −80° C. until further testing.

Degradation Assay:

GAG degradation was monitored by measuring CS released in cell culture media using the dimethylmethylene blue (DMMB) dye assay and computed with a chondroitin-6-sulfate standard curve. Similarly, type I collagen degradation in cell culture media was monitored using the Sircol Collagen Assay using manufacturer specified protocols (BioColor). GAG and collagen degradation were reported as cumulative release over an eight-day culture period.

Proteolytic Degradation Analysis:

The amount of CS and collagen released into cell culture media was significantly decreased when scaffolds that contained mAGC (FIGS. 11, 12, 23 and 24) ($p_{CS}<0.001$ and $p_{collagen}<0.02$, respectively). Aligned collagen gels showed a statistically higher CS and collagen release into the media as compared to unaligned collagen fibers ($p<0.001$).

As described herein, the hyaluronic-binding synthetic peptidoglycan is able to protect HA and the underlying collagen fibers in the scaffold from proteolytic cleavage. The synthesis of the hyaluronic-binding synthetic peptidoglycan utilized the chondroprotective benefits of CS. CS has been shown to down-regulate matrix metalloproteases production. Our synthetic peptidoglycan design herein described allowed CS chains to be attached to HA, preventing degradation of both molecules. By placing the synthetic peptidoglycan in an environment rich in proteolytic enzymes, its ability to prevent excessive loss of ECM components has been demonstrated.

EXAMPLE 15

Real-Time PCR

Figure 25:
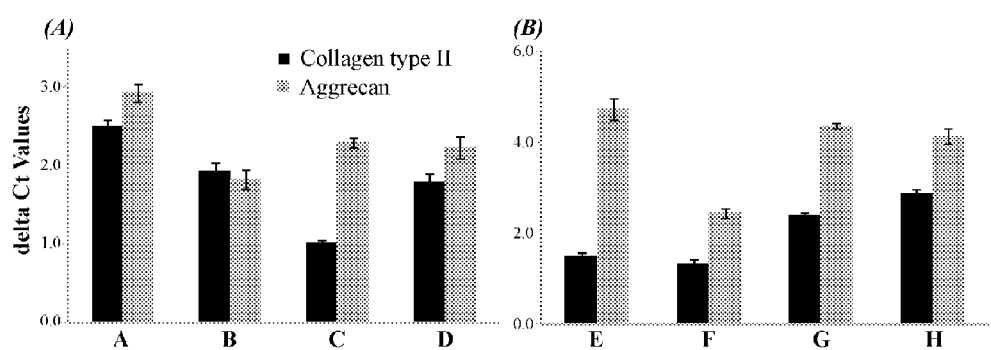
FIG. 25 shows real-time PCR analysis for aggrecan and collagen type II expressed by bovine chondrocytes cultured in unaligned (A) and aligned (B) collagen scaffolds. Values were normalized to endogenous GAPDH expression. Addition of mAGC statistically changed aggrecan and collagen type II expression ($p_{aggrecan}<0.02$ and $p_{collagen}<0.001$) respectively. There was also a statistical difference in aggrecan and collagen type II expression between unaligned and aligned scaffolds (p<0.001). Similarly, the aggrecan and collagen type II expression differed between scaffolds treated with and without IL-1β (p<0.01). Scaffold compositions (A-H) are described in Table 3. Bars represent average ±SEM (n=4).

Following the cell culture study, constructs were stored in RNAlater solution (Ambion) at 4° C. for less than one week. Total mRNA was extracted using Nucleospin RNA II (Clontech) according to manufacturer's protocols. Extracted mRNA from all samples was quantified using Nanodrop 2000 spectrophotometer (Thermo Scientific) and reverse transcribed into cDNA using High Capacity cDNA Reverse Transcriptase Kit (Applied Biosystems). Real-time PCR was performed using Taqman Gene Expression Assays (Applied Biosystems) with the following primers: GAPDH (Bt03210913_g1), aggrecan (Bt03212186_m1) and collagen type II (Bt03251861_m1). 60 ng of cDNA template was prepared per 20 µL reaction for the two genes of interest and the endogenous gene. Real-time PCR analysis was carried out using a Taqman PCR Master Mix and 7500 Real-Time PCR System (Applied Biosystems). Data reported was normalized to GAPDH gene expression.

mRNA Expression Analysis:

Collagen alignment, presence of aggrecan mimic and stimulation with IL-1β significantly effected aggrecan ($p_{alignment}<0.001$, $p_{peptidoglycan}<0.02$ and $p_{IL-1\beta}<0.001$) and collagen type II expression ($p_{alignment}<0.01$, $p_{peptidoglycan}<0.001$ and $p_{IL-1\beta}<0.015$). The presence of mAGC limited excessive loss of CS from the scaffold, which results in a lower aggrecan expression ($p<0.02$) (FIG. 25). The presence of mAGC also limited collagen degradation. However, collagen type II expression depended on the extent of collagen lost during degradation (FIG. 25). In unaligned scaffolds, the level of collagen type II expression was higher in scaffolds prepared without mAGC, whereas in aligned collagen scaffolds, the level of collagen type II was higher in scaffolds prepared with mAGC ($p<0.05$).

EXAMPLE 16

Statistical Analysis

Each experiment was repeated twice, with at least n=3 in each data set. Statistical significance for mechanical test data was analyzed with a two-way ANOVA with alignment and addition of peptidoglycan as factors. The cell culture data was analyzed using a three-way ANOVA with alignment, addition of peptidoglycan, and treatment with IL-1β as factors. A post-hoc Tukey pairwise comparison ($\alpha=0.05$) was used to directly compare scaffolds prepared with and without the aggrecan mimic in each system.

What is claimed is:

1. A synthetic peptidoglycan comprising a glycan and 1 to 20 synthetic peptides conjugated to the glycan, wherein each synthetic peptide is 5 to 40 amino acids in length and comprises a hyaluronic acid-binding amino acid sequence, and wherein the glycan is selected from the group consisting of dextran, chondroitin, chondroitin sulfate, dermatan, dermatan sulfate, heparan, heparin, keratin, and keratan sulfate.

2. The synthetic peptidoglycan of claim 1 wherein each synthetic peptide comprises an amino acid sequence of the formula B1-X1-X2-X3-X4-X5-X6-X7-X8-B2,
   wherein X8 is present or is not present,
   wherein B1 is a basic amino acid,
   wherein B2 is a basic amino acid, and
   wherein X1-X8 are non-acidic amino acids.

3. The synthetic peptidoglycan of claim 1 wherein each synthetic peptide comprises:
   (i) an amino acid sequence selected from the group consisting of:

| | |
|---|---|
| GAHWQFNALTVRGG; | (SEQ ID NO: 2) |
| GDRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |

-continued

| | |
|---|---|
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR, or | (SEQ ID NO: 34) |

(ii) an amino acid sequence having at least 90% sequence identity to an amino acid sequence of (i).

4. The synthetic peptidoglycan of claim 1, wherein at least a synthetic peptide comprises the amino acid sequence GAHWQFNALTVRGG (SEQ ID NO: 2), or an amino acid sequence having at least about 90% sequence identity to GAHWQFNALTVRGG (SEQ ID NO: 2).

5. The synthetic peptidoglycan of claim 4, wherein each glycan is conjugated to about 10 synthetic peptides.

6. A synthetic peptidoglycan comprising a glycan and 1 to 20 synthetic peptides covalently conjugated to the glycan, wherein each synthetic peptide is 5 to 40 amino acids in length and comprises a hyaluronic acid-binding amino acid sequence.

7. The synthetic peptidoglycan of claim 6, wherein the synthetic peptides are covalently conjugated to the glycan through a linker.

8. The synthetic peptidoglycan of claim 6, wherein the glycan is selected from the group consisting of dextran, chondroitin, chondroitin sulfate, dermatan, dermatan sulfate, heparan, heparin, keratin, keratan sulfate, and hyaluronic acid.

9. The synthetic peptidoglycan of claim 6 wherein each synthetic peptide comprises:

(i) an amino acid sequence selected from the group consisting of:

| | |
|---|---|
| GAHWQFNALTVRGG; | (SEQ ID NO: 2) |
| GDRRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPG | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR, or | (SEQ ID NO: 34) |

(ii) an amino acid sequence having at least 90% sequence identity to an amino acid sequence of (i).

10. A method for treating arthritis in a patient in need thereof, said method comprising administering to the patient a synthetic peptidoglycan of claim 6.

11. A method of treatment for arthritis in a patient, said method comprising administering to the patient a synthetic peptidoglycan comprising a glycan and 1 to 20 synthetic peptides conjugated to the glycan, wherein each synthetic peptide is 5 to 40 amino acids in length and comprises a hyaluronic acid-binding amino acid sequence, and wherein the glycan is selected from the group consisting of dextran, chondroitin, chondroitin sulfate, dermatan, dermatan sulfate, heparan, heparin, keratin, and keratan sulfate.

12. The method of claim 11 wherein each synthetic peptide comprises an amino acid sequence of the formula B1-X1-X2-X3-X4-X5-X6-X7-X8-B2,
wherein X8 is present or is not present,
wherein B1 is a basic amino acid,
wherein B2 is a basic amino acid, and
wherein X1-X8 are non-acidic amino acids.

13. The method of claim 11 wherein each synthetic peptide comprises:
(i) an amino acid sequence selected from the group consisting of:

| | |
|---|---|
| GAHWQFNALTVRGG; | (SEQ ID NO: 2) |
| GDRRRRMWHRQ; | (SEQ ID NO: 3) |
| GKHLGGKHRRSR; | (SEQ ID NO: 4) |
| RGTHHAQKRRS; | (SEQ ID NO: 5) |
| RRHKSGHIQGSK; | (SEQ ID NO: 6) |
| SRMHGRVRGRHE; | (SEQ ID NO: 7) |
| RRRAGLTAGRPR; | (SEQ ID NO: 8) |
| RYGGHRTSRKWV; | (SEQ ID NO: 9) |
| RSARYGHRRGVG; | (SEQ ID NO: 10) |
| GLRGNRRVFARP; | (SEQ ID NO: 11) |
| SRGQRGRLGKTR; | (SEQ ID NO: 12) |
| DRRGRSSLPKLAGPVEFPDRKIKGRR; | (SEQ ID NO: 13) |
| RMRRKGRVKHWG; | (SEQ ID NO: 14) |
| RGGARGRHKTGR; | (SEQ ID NO: 15) |
| TGARQRGLQGGWGPRHLRGKDQPPGR; | (SEQ ID NO: 16) |
| RQRRRDLTRVEG; | (SEQ ID NO: 17) |
| STKDHNRGRRNVGPVSRSTLRDPIRR; | (SEQ ID NO: 18) |
| RRIGHQVGGRRN; | (SEQ ID NO: 19) |
| RLESRAAGQRRA; | (SEQ ID NO: 20) |
| GGPRRHLGRRGH; | (SEQ ID NO: 21) |
| VSKRGHRRTAHE; | (SEQ ID NO: 22) |
| RGTRSGSTR; | (SEQ ID NO: 23) |
| RRRKKIQGRSKR; | (SEQ ID NO: 24) |
| RKSYGKYQGR; | (SEQ ID NO: 25) |
| KNGRYSISR; | (SEQ ID NO: 26) |
| RRRCGQKKK; | (SEQ ID NO: 27) |
| KQKIKHVVKLK; | (SEQ ID NO: 28) |
| KLKSQLVKRK; | (SEQ ID NO: 29) |
| RYPISRPRKR; | (SEQ ID NO: 30) |
| KVGKSPPVR; | (SEQ ID NO: 31) |
| KTFGKMKPR; | (SEQ ID NO: 32) |
| RIKWSRVSK; and | (SEQ ID NO: 33) |
| KRTMRPTRR, or | (SEQ ID NO: 34) |

(ii) an amino acid sequence having at least 90% sequence identity to an amino acid sequence of (i).

14. The method of claim 11, wherein the synthetic peptidoglycan is resistant to aggrecanase.

15. The method of claim 11, wherein the peptide component of the synthetic peptidoglycan has a glycine-cysteine attached to the C-terminus of the peptide.

16. The method of claim 11, wherein the arthritis is selected from the group consisting of osteoarthritis and rheumatoid arthritis.

17. The method of claim 11, wherein the synthetic peptidoglycan is in a concentration ranging from about 0.1 µM to about 10 µM.

* * * * *

SEQUENCE LISTING

<160> NUMBER OF SEQ ID NOS: 59

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(8)
<223> OTHER INFORMATION: Any non-acidic amino acid
<220> FEATURE:
<221> NAME/KEY: MOD_RES
<222> LOCATION: (9)..(9)
<223> OTHER INFORMATION: Any non-acidic amino acid or absent
<220> FEATURE:
<221> NAME/KEY: MOD_RES
<222> LOCATION: (10)..(10)
<223> OTHER INFORMATION: Any basic amino acid
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala His Trp Gln Phe Asn Ala Leu Thr Val Arg Gly Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asp Arg Arg Arg Arg Arg Met Trp His Arg Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Lys His Leu Gly Gly Lys His Arg Arg Ser Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Thr His His Ala Gln Lys Arg Arg Ser
1               5                   10

<210> SEQ ID NO 6
<211> LENGTH: 12
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 6

Arg Arg His Lys Ser Gly His Ile Gln Gly Ser Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Arg Met His Gly Arg Val Arg Gly Arg His Glu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Arg Ala Gly Leu Thr Ala Gly Arg Pro Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Tyr Gly Gly His Arg Thr Ser Arg Lys Trp Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ala Arg Tyr Gly His Arg Arg Gly Val Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Arg Gly Asn Arg Arg Val Phe Ala Arg Pro
1               5                   10

```
<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Arg Gly Gln Arg Gly Arg Leu Gly Lys Thr Arg
1               5                   10

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Arg Gly Arg Ser Ser Leu Pro Lys Leu Ala Gly Pro Val Glu
1               5                   10                  15

Phe Pro Asp Arg Lys Ile Lys Gly Arg Arg
            20                  25

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Met Arg Arg Lys Gly Arg Val Lys His Trp Gly
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Gly Ala Arg Gly Arg His Lys Thr Gly Arg
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Ala Arg Gln Arg Gly Leu Gln Gly Gly Trp Gly Pro Arg His
1               5                   10                  15

Leu Arg Gly Lys Asp Gln Pro Pro Gly Arg
            20                  25

<210> SEQ ID NO 17
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Gln Arg Arg Arg Asp Leu Thr Arg Val Glu Gly
1               5                   10

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Lys Asp His Asn Arg Gly Arg Arg Asn Val Gly Pro Val Ser
1               5                   10                  15

Arg Ser Thr Leu Arg Asp Pro Ile Arg Arg
            20                  25

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Ile Gly His Gln Val Gly Gly Arg Arg Asn
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Leu Glu Ser Arg Ala Ala Gly Gln Arg Arg Ala
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Pro Arg Arg His Leu Gly Arg Arg Gly His
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 22

Val Ser Lys Arg Gly His Arg Arg Thr Ala His Glu
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Gly Thr Arg Ser Gly Ser Thr Arg
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Arg Lys Lys Ile Gln Gly Arg Ser Lys Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Lys Ser Tyr Gly Lys Tyr Gln Gly Arg
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Asn Gly Arg Tyr Ser Ile Ser Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Arg Cys Gly Gln Lys Lys Lys
1               5

<210> SEQ ID NO 28
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Gln Lys Ile Lys His Val Val Lys Leu Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Leu Lys Ser Gln Leu Val Lys Arg Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Tyr Pro Ile Ser Arg Pro Arg Lys Arg
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Val Gly Lys Ser Pro Pro Val Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Thr Phe Gly Lys Met Lys Pro Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ile Lys Trp Ser Arg Val Ser Lys
```

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Arg Thr Met Arg Pro Thr Arg Arg
1               5

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ala His Trp Gln Phe Asn Ala Leu Thr Val Arg Gly Gly Gly Cys
1               5                   10                  15

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Tyr Arg Gly Arg Leu Gly Cys
1               5

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Arg Ala Ser Arg Ser Arg Gly Gln Val Gly Leu
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Arg Gly Thr His His Ala Gln Lys Arg Arg Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 39

Gln Pro Val Arg Arg Leu Gly Thr Pro Val Val Gly
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Arg Ala Glu Gly Lys Thr Arg Met Leu Gln
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Lys Val Arg Gly Arg Arg His Gln Ala Ser Gly
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Asp Arg His Arg Arg Arg Glu Ala Asp Gly
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Gln Arg Val Arg Arg Val Lys His Pro Pro Gly
1               5                   10

<210> SEQ ID NO 44
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Glu Arg Arg Glu Arg His Ala Val Ala Arg His Gly Pro Gly Leu
1               5                   10                  15

Glu Arg Asp Ala Arg Asn Leu Ala Arg Arg
            20                  25
```

<210> SEQ ID NO 45
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Val Arg Pro Gly Gly Lys Arg Gly Gly Gln Val Gly Pro Pro Ala
1               5                   10                  15

Gly Val Leu His Gly Arg Arg Ala Arg Ser
            20                  25

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Val Arg Ser Arg Arg Gly His Arg Met Asn Ser
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Arg Arg Arg Gly Arg Thr Arg Asn Ile Gly Asn
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Thr Ala Gly His Gly Arg Arg Trp Ser Arg Asn
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Lys Arg Gly Glu Gly Arg Arg Glu Trp Pro Arg
1               5                   10

<210> SEQ ID NO 50
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 50

Gly Gly Asp Arg Arg Lys Ala His Lys Leu Gln Ala
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Arg Gly Gly Arg Lys Trp Gly Ser Phe Glu Gly
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Asp Gly Thr Arg Tyr Val Gln Lys Gly Glu Tyr Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Arg Glu Ala Arg Ser Gly Lys Tyr Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Asp Lys Lys His Lys Leu Tyr Gly Val
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Asp Lys Glu Arg Ser Arg Tyr Asp Val
1               5                   10
```

```
<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Gln Lys Ile Lys His Val Val Lys Leu Lys Gly Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Leu Lys Ser Gln Leu Val Lys Arg Lys Gly Cys
1               5                   10

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Tyr Arg Gly Arg Leu
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Pro Leu Gly Met Arg Gly Leu Gly Lys
1               5                   10
```